(12) United States Patent
Gruzman et al.

(10) Patent No.: US 12,252,472 B1
(45) Date of Patent: *Mar. 18, 2025

(54) BARBITURIC ACID DERIVATIVES, THEIR PREPARATION AND USE THEREOF AS LEUKOCYTE TRANSMIGRATION INHIBITORS AND FOR TREATING INFLAMMATORY DISEASES, AUTOIMMUNE DISEASES AND CANCER

(71) Applicants: BAR-ILAN UNIVERSITY, Ramat Gan (IL); UNIVERSITY OF GENEVA, Geneva (CH); GENEVA UNIVERSITY HOSPITALS, Geneva (CH)

(72) Inventors: Arie Lev Gruzman, Tzur Hadassah (IL); Paul Bradfield, Geneva (CH); Tamar Getter, Ashkelon (IL); Beat Imhof, Conches (CH); Thomas Matthes, Onex (CH); Hanoch Senderowitz, Tel Aviv (IL)

(73) Assignees: BAR-ILAN UNIVERSITY, Ramat Gan (IL); UNIVERSITY OF GENEVA, Geneva (CH); GENEVA UNIVERSITY HOSPITALS, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/957,549

(22) Filed: Sep. 30, 2022

Related U.S. Application Data

(62) Division of application No. 16/642,496, filed as application No. PCT/IL2018/050961 on Aug. 30, 2018, now Pat. No. 11,492,333.

(60) Provisional application No. 62/552,491, filed on Aug. 31, 2017.

(51) Int. Cl.
C07D 239/62 (2006.01)

(52) U.S. Cl.
CPC .................... C07D 239/62 (2013.01)

(58) Field of Classification Search
CPC ................................... C07D 239/62
See application file for complete search history.

(56) References Cited

U.S. PATENT DOCUMENTS

| 11,492,333 B2 * | 11/2022 | Gruzman | ............ A61K 31/515 |
| 2020/0181094 A1 | 6/2020 | Gruzman et al. | |

FOREIGN PATENT DOCUMENTS

| WO | 00/13708 | 3/2000 |
| WO | 02/068057 | 9/2002 |
| WO | 2007/002587 | 1/2007 |
| WO | 2009/078588 | 6/2009 |
| WO | 2010/136804 | 12/2010 |
| WO | 2014/047232 | 3/2014 |

OTHER PUBLICATIONS

Pinedo et al.(2000).*
McMahon et al. 92000).*
International Search Report issued in PCT/IL2018/050961 dated Nov. 29, 2018.
Written Opinion of the International Searching Authority issued in PCT/IL2018/050961 dated Nov. 29, 2018.
CAS Registry No. 348579-85-1; (Jul. 26, 2001).
CAS Registry No. 426230-45-7 (Jun. 9, 2002).
CAS Registry No. 454188-06-8 (Sep. 23, 2002).
CAS Registry No. 455322-87-9 (Sep. 26, 2002).
Delisser et al., "Vascular endothelial platelet endothelial cell adhesion molecule 1 (PECAM-1) regulates advanced metastatic progression" *PNAS*, 107(43):18616-18621 (Oct. 26, 2010).
Harriman et al., "Selective cell adhesion inhibitors: Barbituric acid based α4β7—MAdCAM inhibitors" *Bioorganic & Medicinal Chemistry Letters*, vol. 18: 2509-2512 (2008).
Ingle et al., "Synthesis and biological activities of glycoconjugated spiro triones" *International Journal of PharmTech Research*, 1(3): 605-612 (Jul.-Sep. 2009).
Ma et al., "Synthesis and biological activity of novel barbituric and thiobarbituric acid derivatives against non-alcoholic fatty liver disease" *European Journal of Medicinal Chemistry*, 46 (6): 2003-2010 (2011).
Ma et al., "Synthesis and Biological Evaluation of 5-Benzylidenepyrimidine-2,4,6(1H,3H,5H)-trione Derivatives for the Treatment of Obesity-Related Nonalcoholic Fatty Liver Disease" *Journal of Medicinal Chemistry*, 55(22): 9958-9972 (2012).
Mamdouh et al., "Targeted recycling of PECAM from endothelial surface-connected compartments during diapedesis" Nature, 421: 748-753 (Feb. 13, 2003).
Qing et al., "Inhibition of Antigen-Specific T Cell Trafficking into the Central Nervous System via Blocking PECAM1/CD31 Molecule" *Journal of Neuropathology and Experimental Neurology*, 60(8):798-807 (Aug. 2001).
Shono et al., "Characterization of a c-Rel Inhibitor That Mediates Anticancer Properties in Hematologic Malignancies by Blocking NF-κB-Controlled Oxidative Stress Responses" *Therapeutics, Cancer Research*, 76(2): OF1-OF13 (Jan. 15, 2016).
Vassiliou et al., "A synthetic method for diversification of the P1' substituent in phosphinic dipeptides as a tool for exploration of the specificity of the S1' binding pockets of leucine aminopeptidases" *Bioorganic & Medicinal Chemistry*, 15(9): 3187-3200 (2007).
Xu et al., "Anti-inflammatory effects of novel barbituric acid derivatives in T lymphocytes" *International Immunopharmacology*, 38: 223-232 (2016).
Zheng et al., "A novel agonist of PPAR-γ based on barbituric acid alleviates the development of non-alcoholic fatty liver disease by regulating adipocytokine expression and preventing insulin resistance" *European Journal of Pharmacology*, 659 (2-3): 244-251 (2011).

(Continued)

*Primary Examiner* — Paul V Ward
(74) *Attorney, Agent, or Firm* — Nixon & Vanderhye PC

(57) ABSTRACT

Provided herein are novel barbituric acid derivatives, their synthesis and use thereof in blocking leukocyte transmigration. The novel barbituric acid derivatives are useful for the treatment of disorders associated with leukocyte transmigration, such as for example inflammatory diseases and disorders, autoimmune diseases and disorders, and cancers.

28 Claims, 27 Drawing Sheets

(56) References Cited

OTHER PUBLICATIONS

Zidar et al., "New 5-benzylidenethiazolidin-4-one inhibitors of bacterial MurD ligase: Design, synthesis, crystal structures, and biological evaluation" *European Journal of Medicinal Chemistry*, 46(11): 5512-5523 (2011).
Pinedo et al., "Translational Research: The Role of VEGF in Tumor Angiogenesis", The Oncologist, Apr. 2000, vol. Issue S1, pp. 1-2.
McMahon et al., "VEGF Receptor Signaling in Tumor Angiogenesis", The Oncologist, Apr. 2000, vol. 5, Issue S1, pp. 3-10.

* cited by examiner

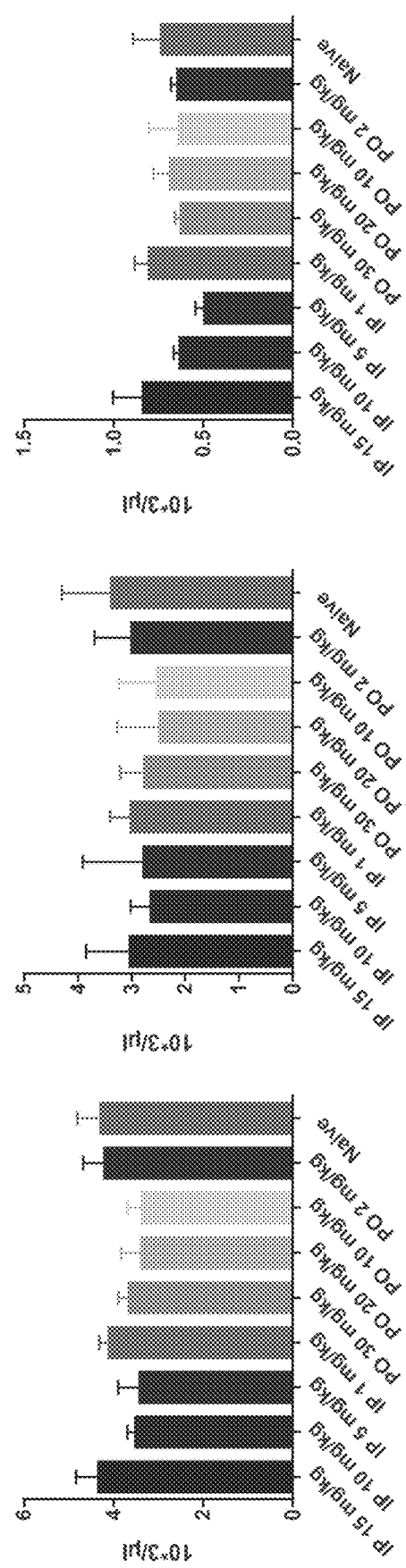
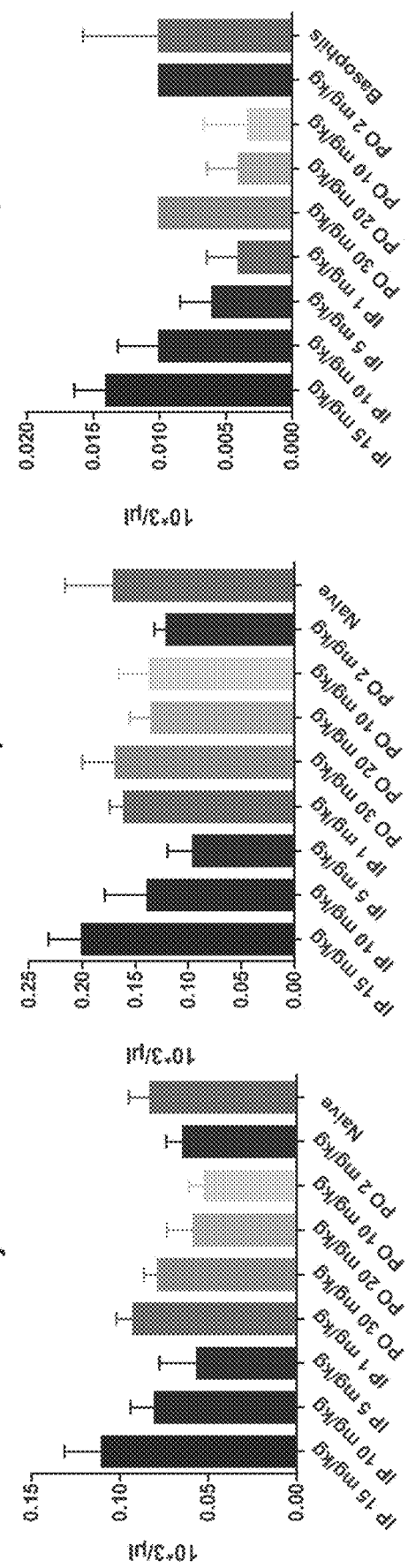

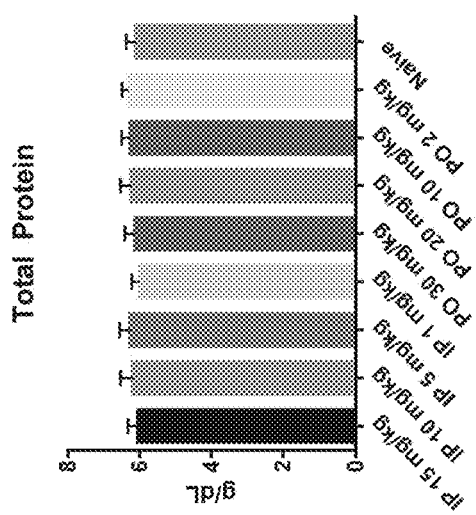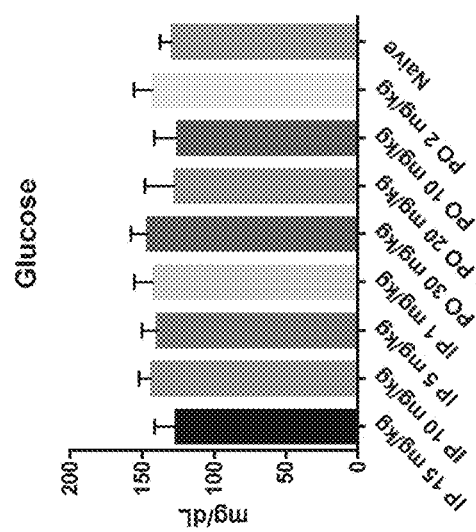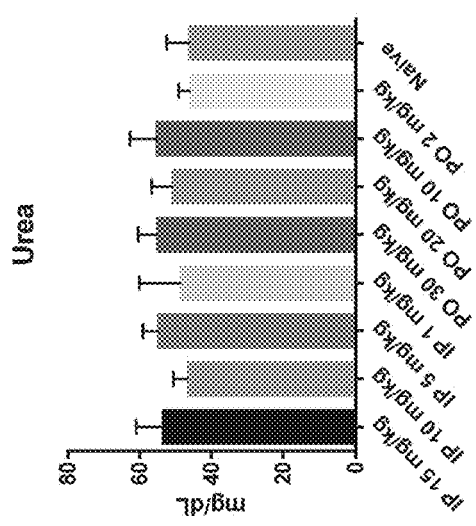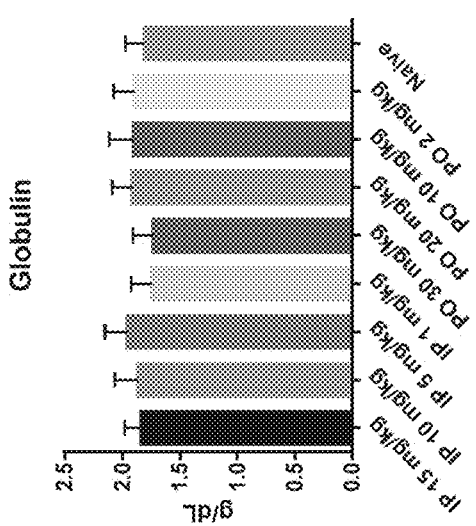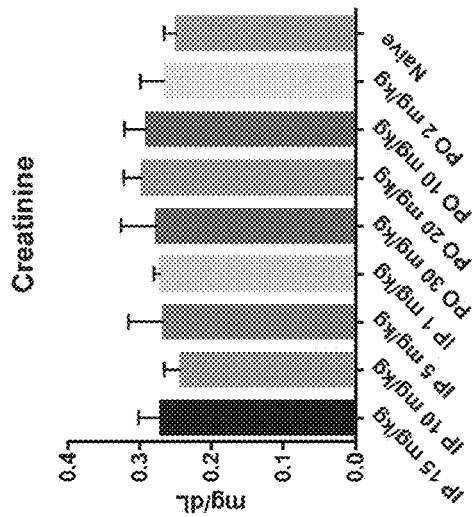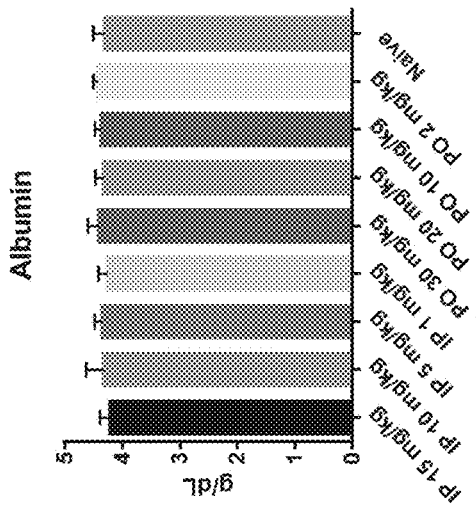

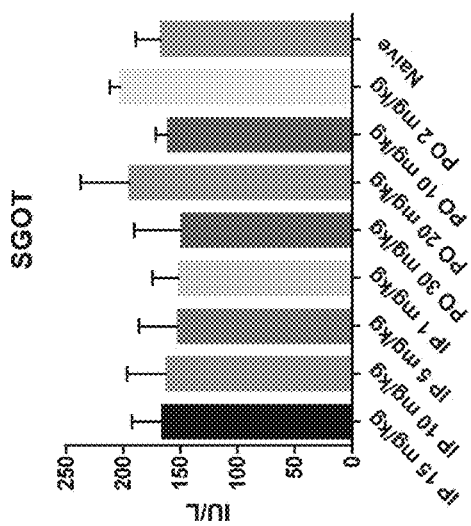
Figure 13A
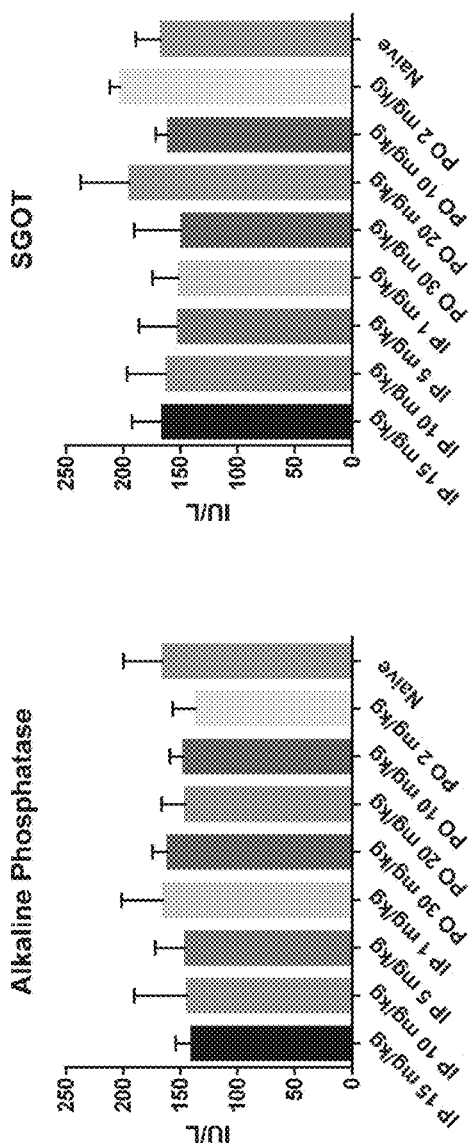
Figure 13B
Figure 13C
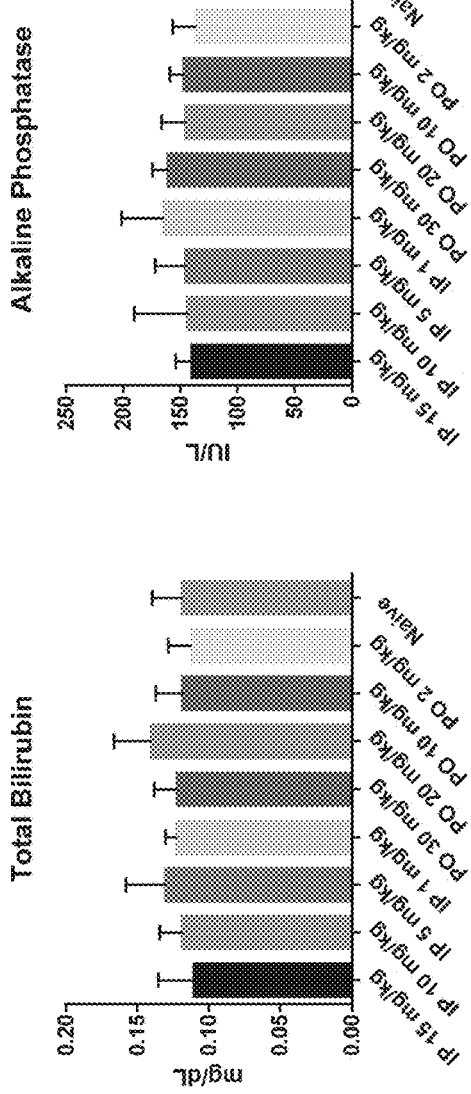
Figure 13D
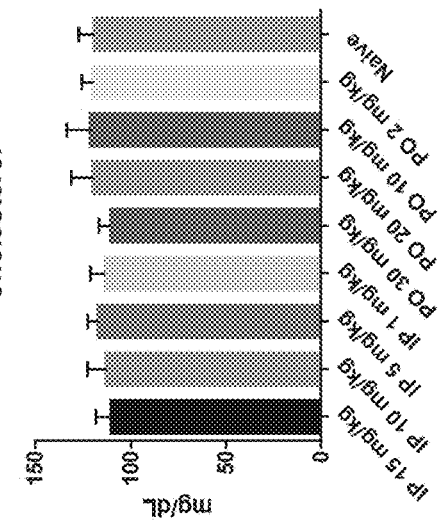
Figure 13E

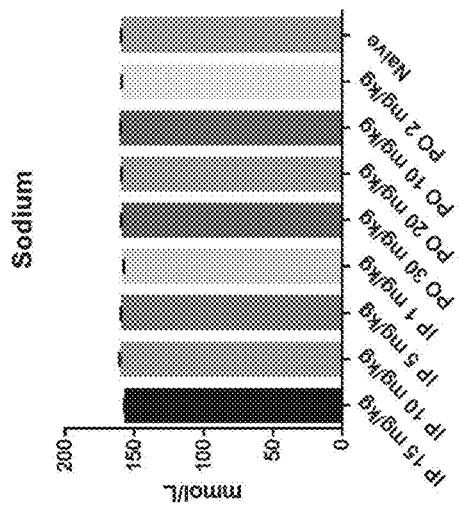
Figure 14A
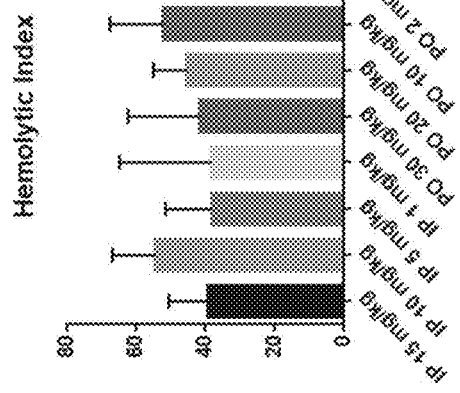
Figure 14B
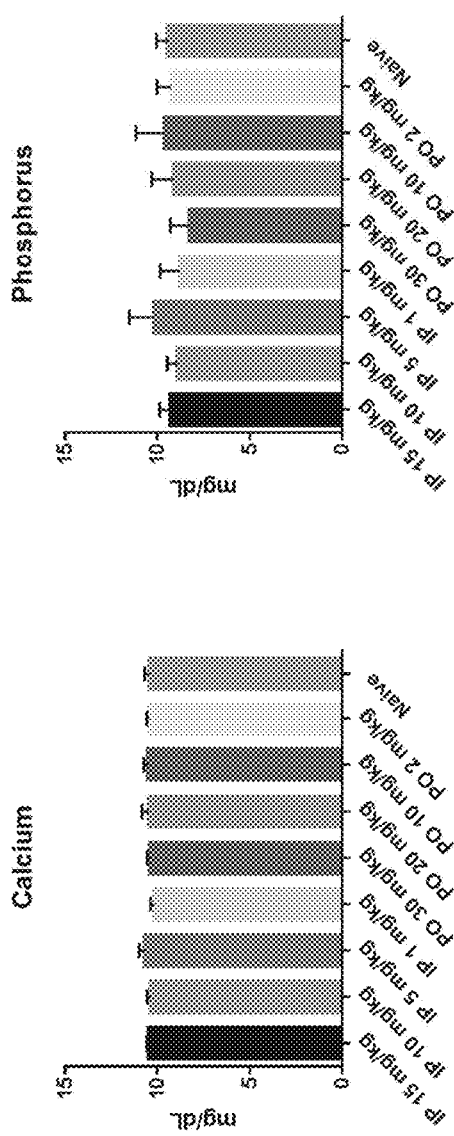
Figure 14C
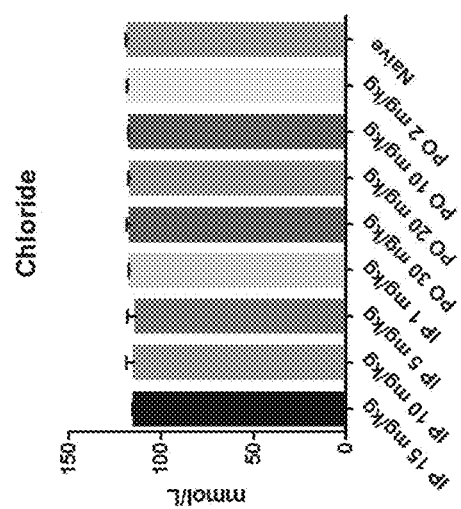
Figure 14D
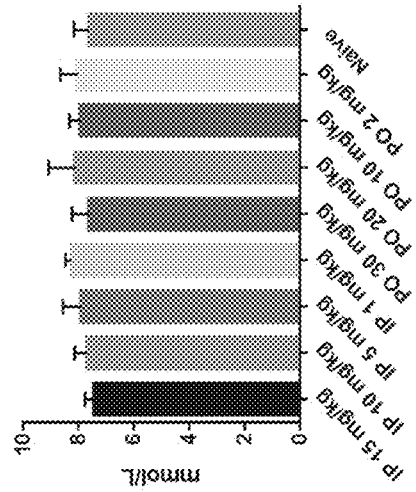
Figure 14E
Figure 14F

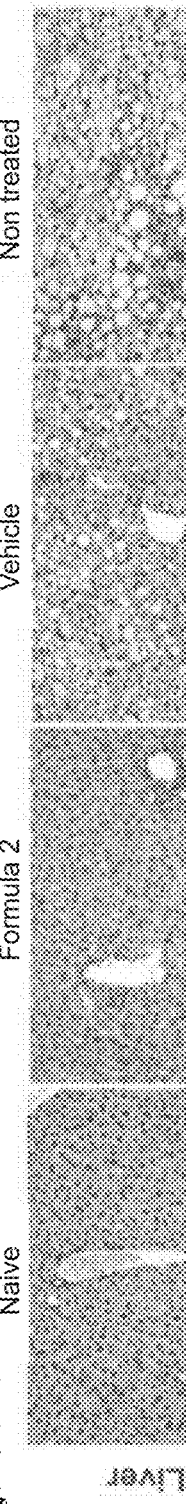
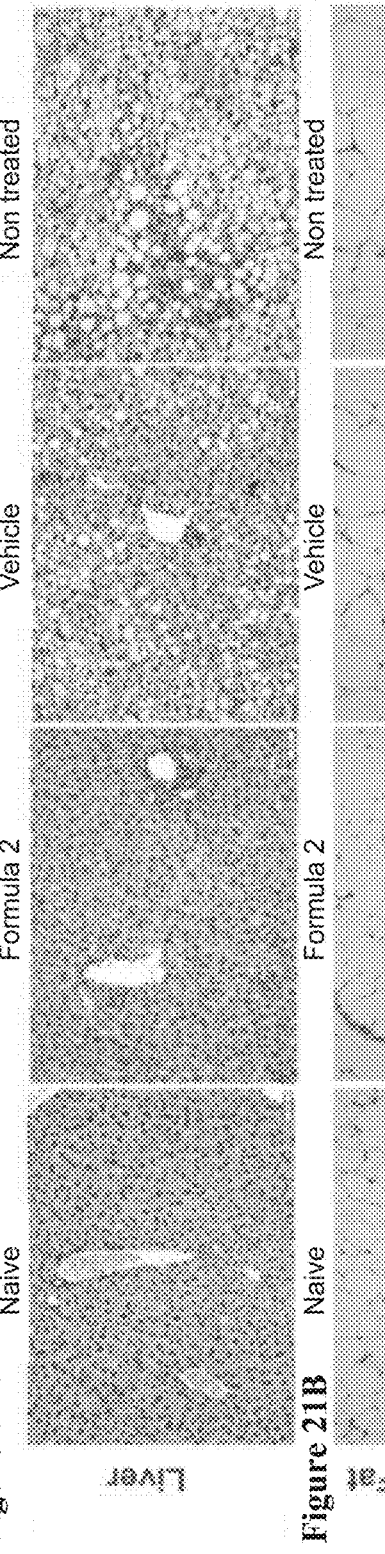
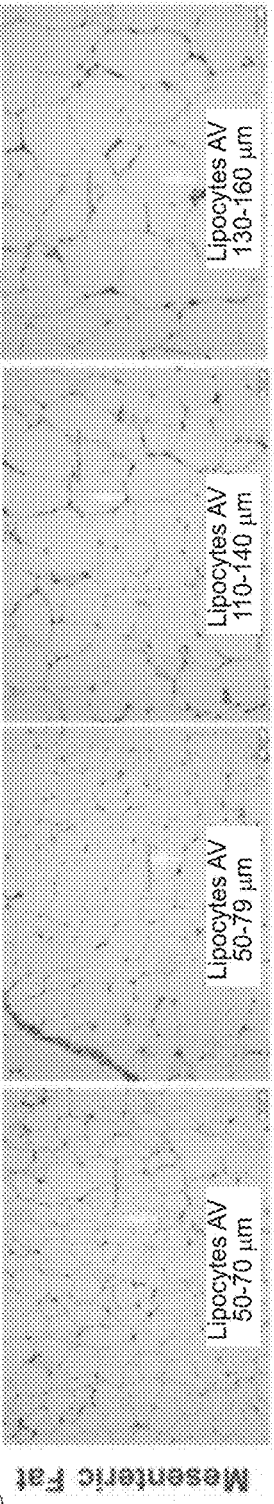
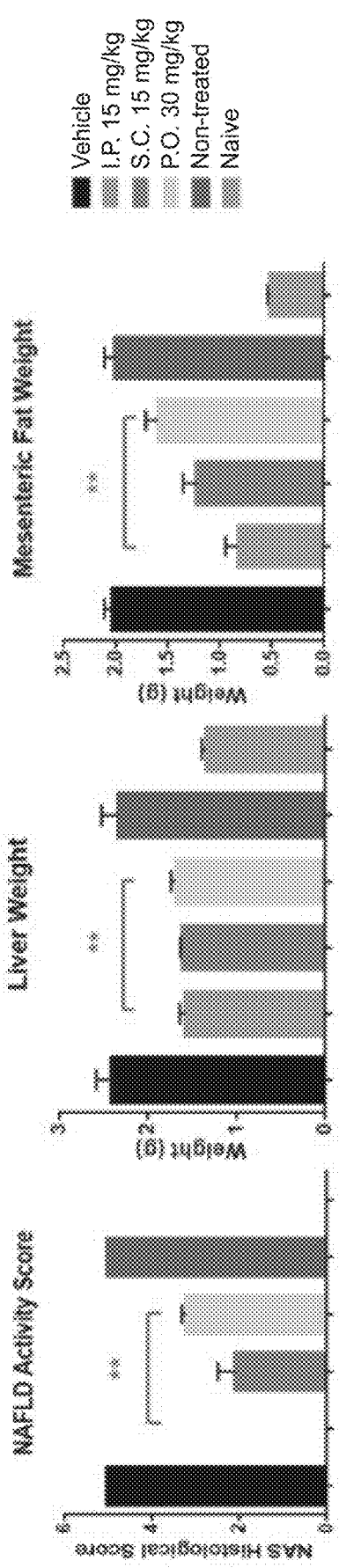
Figure 21A
Figure 21B
Figure 21C
Figure 21D
Figure 21E

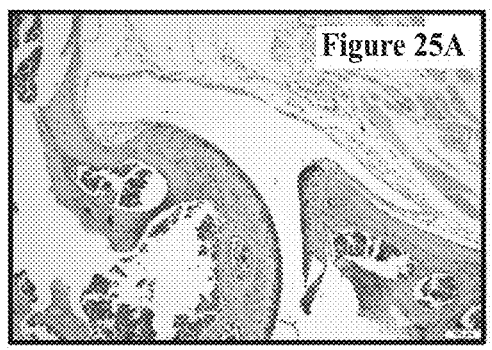
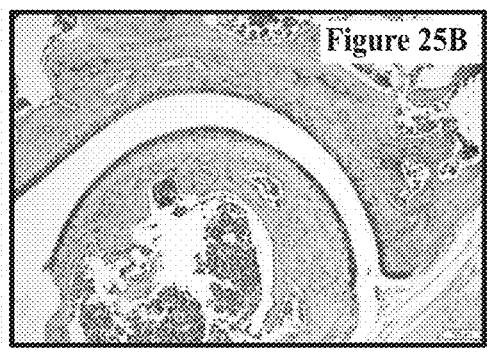
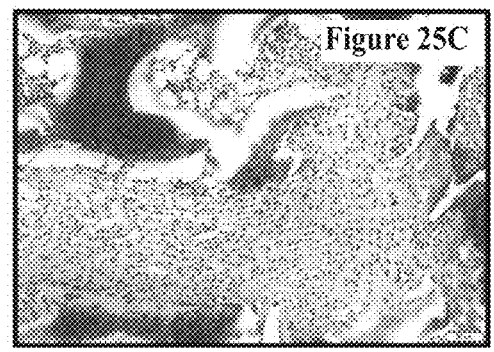
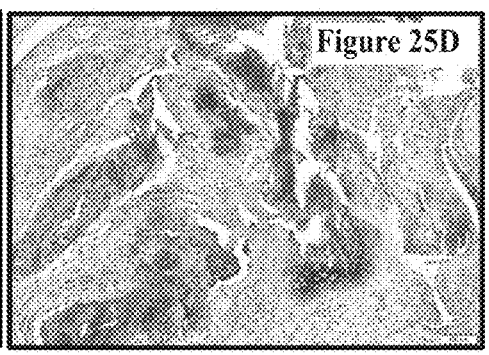
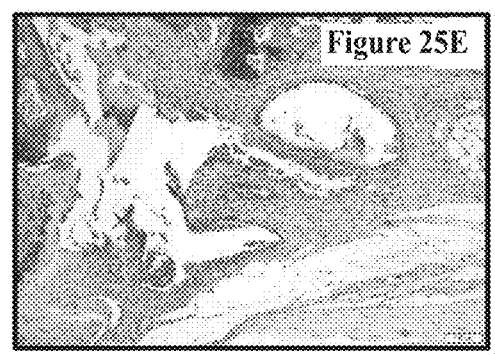
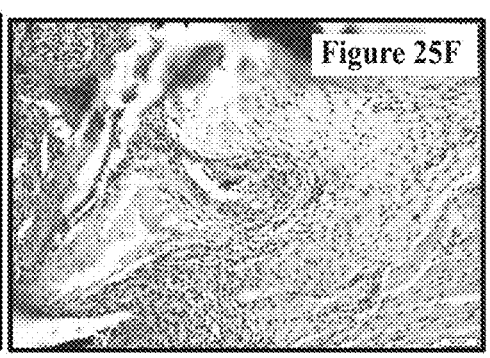
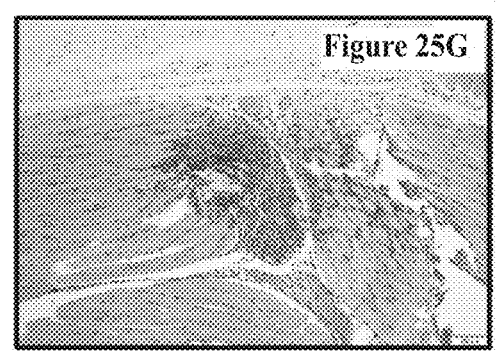
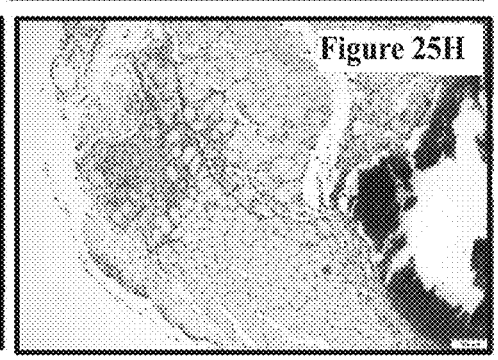
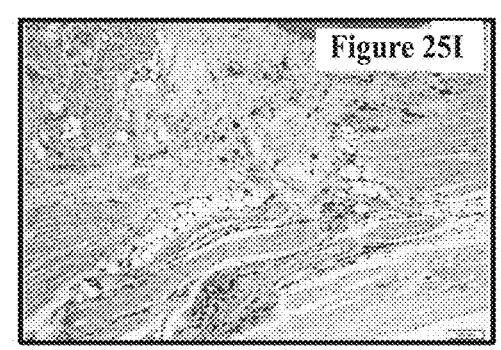
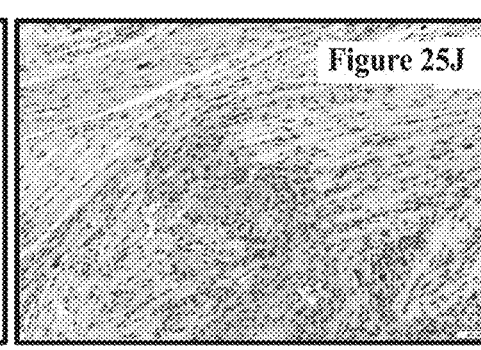

BARBITURIC ACID DERIVATIVES, THEIR PREPARATION AND USE THEREOF AS LEUKOCYTE TRANSMIGRATION INHIBITORS AND FOR TREATING INFLAMMATORY DISEASES, AUTOIMMUNE DISEASES AND CANCER

This application is a divisional of U.S. application Ser. No. 16/642,496 filed Feb. 27, 2020, which is a National Phase of International Application No. PCT/IL2018/050961 filed Aug. 30, 2018, which claims priority to U.S. Provisional Patent Application No. 62/552,491 filed Aug. 31, 2017, the entire contents of each of which are hereby incorporated by reference.

DESCRIPTION

The invention relates to the use of small organic compounds for blocking leukocyte transmigration for the treatment of diseases and disorders associated with autoimmune response inflammation. The invention further relates to the use of small organic compounds for blocking leukocyte transmigration for the treatment of lymphoma. The invention also relates to the use of small organic compounds for blocking leukocyte transmigration for the treatment of tumor formation. In particular, the present invention relates to the compounds of the general Formula (I) for the treatment of inflammatory diseases and disorders and autoimmune diseases and disorders. The present invention also relates to the compounds of the general Formula (I) for the treatment of diseases and disorders, where the transmigration of leukocytes from blood to tissues occurs, for example cancers, such as lymphomas. Surprisingly, the inventors have found that the compounds of the general Formula (I) are useful for the treatment of lymphoma cells trafficking through lymphatic sites; and the treatment of cancer where cell trafficking from the vasculature (including secondary metastatic events) leads to the expansion and/or vascularization of tumors. The present invention also embraces pharmaceutical compositions comprising these compounds, including the stereoisomers, enantiomers and tautomers thereof, mixtures thereof and pharmaceutically acceptable salts thereof, and methods of using the compounds and their pharmaceutical compositions.

Inflammatory, autoimmune and cancer diseases constitute a major part of the total burden of diseases that affect humans. Dozens of drugs are in use to treat these disorders. However, in many cases complete recovery is not achieved and the majority of the drugs have very serious side effects. Several autoimmune diseases, such as for example Crohn's disease, multiple sclerosis, arthritis, fatty liver disease (including Non-alcoholic fatty liver disease (NAFLD) and Non-alcoholic steatohepatitis (NASH)), ankylosing spondylitis, psoriasis, and lupus erythematosus, are fatal or not treatable, or have very poor treatment options.

Leukocytes are dominant cells in the management of broad spectra of immune reactions in both physiological and pathological conditions. In addition to their ability to regulate the immune response by humoral stimuli, their physical location in specific tissues is critical for a prominent immune response. Leukocytes are able to exit the blood and lymphoid compartments and reach peripheral tissues in a very short period of time due to their unique flexible cytoskeleton, the ability to exercise cell polarization, and vessel wall penetration through amoeboid-like movement.

The adhesion, rolling, transmigration and homing of leukocytes are mediated by various different molecules. The immune system also has an ability to activate leukocyte transmigration through regulated interactions between the systemic humoral response and specific cell immune machinery. Also cellular components of the immune system such as mast cells, macrophages, and dendritic cells are able to mediate leukocyte homing to injured or infected areas in peripheral tissues by the secretion of molecular mediators.

Leukocyte recruitment to these areas is rapid, expanding from low affinity interactions with activated endothelial cells associated with immunosurveillance and physical contact with distal post-capillary endothelial cells. These weak interactions with activated endothelial cells are able to accelerate a cascade of events that lead to leukocyte arrest and tight adhesion, followed by crawling on vascular luminal surfaces. This is proceeded by transendothelial migration across the vessel wall (transmigration) of the leukocyte into the adjacent tissue and migration towards the peripheral target tissue.

Targeting leukocyte transmigration was identified as a potential target for anti-inflammatory drug development already in the 1990's. Targeting the interactions between leukocytes and endothelium is considered until now an important axis in drug development, particularly for the treatment of inflammatory and autoimmune related diseases, and lymphoma (Rychly J. and Nebe B., Curr Pharm Des. 2006; 12(29):3799-806; Hua S. and Cabot P J. Trends Pharmacol Sci. 2010: 31(9):427-33).

Integrins have been the main focus for the design of these new therapeutic agents. Integrin blockers have shown significant benefits in the clinic with many patients, leading to continued medical interest in the further development of novel integrin inhibitors. Currently, almost all human integrins have been used as targets for the development of effective antagonists. Some of these molecules have become commercially available drugs; and some of them are under clinical trials.

Barbituric acid was first synthesized by the German chemist Adolf von Baeyer in 1864. Based on this scaffold several drugs were developed in the last century and were widely used as anticonvulsants, narcosis initiators, antianxiety agents and hypnotics. In modern medicine barbiturates were replaced by less toxic compounds. Presently barbiturates are in use only in very restricted medical areas such as migraine treatment and veterinary medicine.

Barbiturates as integrin antagonists, and their use for treating inflammatory diseases were disclosed in PCT patent application publication No. WO2002068057 and in Harriman G., et. al. (Bioorganic and Medicinal Chemistry Letters, 2008, 18: 2509-2512). Recently, Xu C. et al. (International Immunopharmacology, 2016, 38: 223-232) described barbituric acid derivatives as novel phosphodiesterase 7 (PDE7) inhibitors that exhibited unusually potent immunosuppressive and immunomodulatory actions on T lymphocyte function, including inhibition of T cell proliferation and IL-2 cytokine production. Barbiturates and their use for preventing or treating viral infections were disclosed in PCT patent application publication No. WO2000013708.

Barbituric acid derivatives reportedly useful against non-alcoholic fatty liver disease were described by Ma L. et al. (Synthesis and biological activity of novel barbituric and thiobarbituric acid derivatives against non-alcoholic fatty liver disease, 2011, European Journal of Medicinal Chemistry, Volume 46, Issue 6, June 2011, Pages 2003-2010) and by Zheng H. et al. (A novel agonist of PPAR-γ based on barbituric acid alleviates the development of non-alcoholic fatty liver disease by regulating adipocytokine expression and preventing insulin resistance, 2011, European Journal of Pharmacology, Volume 659, Issues 2-3, 1 Jun. 2011, Pages 244-251). Barbituric acid derivatives reportedly useful in the treatment of obesity-related nonalcoholic fatty liver disease were described by Ma L. et al. (Synthesis and Biological Evaluation of 5-Benzylidenepyrimidine2,4,6(1H,3H,5H)-trione Derivatives for the Treatment of Obesity-Related Nonalcoholic Fatty Liver Disease, 2012, Journal of Medicinal Chemistry, 2012 Nov. 26; 55(22):9958-72).

Every year in the U.S.A around 80,000 people are diagnosed with 23 different types of B lymphomas. These range from aggressive non-treatable types to classical Hodgkin lymphoma, which can be treated. The percentage survival rate per 5 years is around 70%. However, people with several very aggressive lymphomas, such as small B-cell lymphomas, mantle cell lymphoma or Burkitt's lymphoma typically have a very bad prognosis, despite intensive chemotherapy. Recently, a monoclonal antibody (Rituximab) was introduced as an anti-B cell lymphoma drug (Imhof B A, Matthes T. Swiss Med Wkly. 2017 Sep. 25; 147).

Targeting both leukocytes and the endothelial barrier through common receptor molecules in cancer has been the subject of a number of strategies. A therapeutic antibody that targets the molecule CLEVER-1 (Clevegen FP-1305, Faron Pharmaceuticals) has been shown to block this molecule on tumor endothelium and tumor associated macrophage (TAMs), and is currently undergoing clinical trials.

The role common receptors such as PECAM-1 play in both inflammation and cancer has highlighted a number of opportunities in drug development. This molecule has been shown to play a role in the late stage progression in cancer, highlighting a potential mechanism in disease stratification dependent on the stage of treatment (DeLisser H, Proc Natl Acad Sci USA. 2010, 107(43):18616-21). PECAM-1 is also known to regulate T cell trafficking into the CNS during critical pathologies, demonstrating that targeting this receptor may block multiple cell populations in both inflammation and cancer (Qing Z., et al. Inhibition of antigen-specific T cell trafficking into the central nervous system via blocking PECAM1/CD31 molecule. J Neuropathol Exp Neurol. 2001, 60(8):798-807). PECAM-1 not only resides at the junction, but it is a constituent of a recycling compartment on endothelial cells, termed the lateral border recycling compartment (LBRC) that modulates the transmigration of leukocytes through the endothelial cell-cell junction (Mamdouh et al, Nature, 2003; 421:748-753).

The present invention relates to the use of small organic compounds for blocking leukocyte transmigration for the treatment of diseases associated with leukocyte transmigration. In particular, the present invention provides the compounds of the general Formula (I)

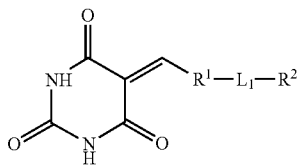

Formula (I)

wherein the groups $R^1$, $L_1$ and $R^2$ are as defined hereinafter, including the stereoisomers, enantiomers and tautomers thereof, mixtures thereof and pharmaceutically acceptable salts thereof.

The invention also relates to processes for preparing a compound of general Formula (I) according to the invention, and stereoisomers, enantiomers, and tautomers thereof, mixtures thereof and pharmaceutically acceptable salts thereof.

In a further aspect, the invention is directed to pharmaceutical compositions containing a compound of general Formula (I) according to the invention, including the stereoisomers, enantiomers and tautomers thereof, mixtures thereof and pharmaceutically acceptable salts thereof, and a pharmaceutically acceptable carrier or diluent. The pharmaceutical compositions according to the invention optionally further comprise at least one additional therapeutic agent including but not limited to, anti-inflammatory agents, antiseptics, antibiotics, antivirals, bactericides, antifungals, antineoplastics, anticancer compounds, and/or other bioactive or therapeutic agents that are suitable for human use.

In a further aspect, the invention is directed to the use of the compound of general Formula (I), including the stereoisomers, enantiomers and tautomers thereof, pharmaceutically acceptable salts thereof, and mixtures thereof, or the use of a pharmaceutical compositions thereof, for the treatment of diseases and disorders. Especially diseases and disorders where the transmigration of leukocytes from blood to tissues occurs, such as, without being limited to, inflammatory and autoimmune diseases and disorders, for example: Myocarditis, Postmyocardial infarction syndrome, Postpericardiotomy syndrome, Subacute bacterial endocarditis (SBE), Anti-Glomerular Basement Membrane nephritis, Interstitial cystitis, Primary sclerosing cholangitis, Antisynthetase syndrome, Alopecia Areata, Autoimmune Angioedema, Autoimmune progesterone dermatitis, Autoimmune urticarial, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease (LAD), Morphea, Pemphigus vulgaris, *Pityriasis lichenoides* et varioliformis acuta, Mucha-Habermann disease, Addison's disease, Autoimmune polyendocrine syndrome (APS) type 1, Autoimmune polyendocrine syndrome (APS) type 2, Autoimmune polyendocrine syndrome (APS) type 3, Autoimmune pancreatitis, Diabetes mellitus type 1, Autoimmune thyroiditis, Ord's thyroiditis, Graves' disease, Autoimmune Oophoritis, Endometriosis, Autoimmune enteropathy, Coeliac disease, Crohn's disease, Antiphospholipid syndrome (APS, APLS), Aplastic anemia, Autoimmune hemolytic anemia, Autoimmune lymphoproliferative syndrome, Cold agglutinin disease, Essential mixed cryoglobulinemia, Evans syndrome, Paroxysmal nocturnal hemoglobinuria, Pernicious anemia, Pure red cell aplasia, Thrombocytopenia, Adiposis dolorosa, Adult-onset Still's disease, Ankylosing Spondylitis, Eosinophilic fasciitis, Felty syndrome, IgG4-related disease, Juvenile Arthritis, Lyme disease (Chronic), Mixed connective tissue disease (MCTD), Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus (SLE), Undifferentiated connective tissue disease, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis (ADEM), Acute motor axonal neuropathy, Anti-N-Methyl-D-Aspartate (Anti-NMDA) Receptor Encephalitis, Balo concentric sclerosis, Bickerstaffs encephalitis, Chronic inflammatory demyelinating polyneuropathy, Guillain-Barré syndrome, Multiple sclerosis, Oshtoran Syndrome, Pediatric Autoimmune Neuropsychiatric Disorder Associated with Streptococcus (PANDAS), Progressive inflammatory neuropathy, Restless leg syndrome, Stiff person syndrome, Sydenham chorea, Transverse myelitis, Autoimmune retinopathy, Autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, Autoimmune inner ear disease (AIED), Mdniere's disease, Behget's disease, Eosinophilic granulomatosis with polyangiitis (EGPA), Giant cell arteritis, Granulomatosis with polyangiitis (GPA), IgA vasculitis (IgAV), Kawasaki's disease, leukocytoclastic vasculitis, Lupus vasculitis, Rheumatoid vasculitis, Microscopic polyangiitis (MPA), Polyarteritis nodosa (PAN), Polymyalgia rheumatic, Urticarial vasculitis, Vasculitis, Primary Immune Deficiency, Hashimoto's encephalopathy, Idiopathic inflammatory demyelinating diseases, Lambert-Eaton myasthenic syndrome, CREST syndrome, Drug-induced lupus, Enthesitis-related arthritis, Autoimmune neutropenia, Autoimmune thrombocytopenic purpura, Microscopic colitis, Ulcerative colitis, Autoimmune orchitis, Sjogren's syndrome, Psoriasis, Systemic scleroderma, Vitiligo, Lupus nephritis, Autoimmune hepatitis, Primary biliary cirrhosis (PBC), and cancers, such as lymphomas, especially types B cell lymphomas. Other aspects and embodiments of the present invention will become apparent to the skilled person from the following detailed description.

BRIEF DESCRIPTION OF THE FIGURES

FIGS. 11A-11F show no effect of the compound of Formula 2 administered with 3 doses by oral gavage (PO) or with 3 doses by intraperitoneal injection (IP) on different subtypes of white blood cells. Data shown mean±SEM, n=5.

FIGS. 12A-12F show no effect of the compound of Formula 2 administered with 3 doses by oral gavage (PO) or with 3 doses by intraperitoneal injection (IP) on blood levels of creatinine, urea, total protein, albumin, globulin, glucose. Data shown mean±SEM, n=5.

FIGS. 13A-13E show no effect of the compound of Formula 2 administered with 3 doses by oral gavage (PO) or with 3 doses by intraperitoneal injection (IP) on blood levels of total billirubin, alkaline phosphatase, serum glutamic oxaloacetic transaminase (SGOT), serum glutamic pyruvic transaminase (SGPT) and cholesterol. Data shown mean±SEM, n=5.

FIGS. 14A-14F show no effect of the compound of Formula 2 administered with 3 doses by oral gavage (PO) or with 3 doses by intraperitoneal injection (IP) on blood levels of calcium, phosphorus, sodium, potassium, chloride and on hemolytic index. Data shown mean±SEM, n=5.

FIGS. 21A-21E show the therapeutic effect of the compound of Formula 2 in High—Fat—Diet induced Fatty Liver Disease in C57BL/6 model in mice administered at 2 doses by oral gavage (PO), intraperitoneal injection (IP) or subcutaneous injection (SC) steatohepatitis and on fat accumulation (Example 10 below). Histology results are shown: liver (21A) and mesenteric fat (21B). The compound of Formula 2 exhibited therapeutic effect on steatohepatitis (NAFLD activity score) (21C). The compound of Formula 2 also decreased liver wet weight (21D) and mesenteric fat wet weight (21E). Data shown mean±SEM, n=8.

FIGS. 25A-25J show the therapeutic effect of the compound of Formula 2 in Collagen Induced Arthritis (CIA) model in DBA/1 mice (histological evaluation). Representative sections through the talus and calcaneum joint of naïve (25A) and treated (25B) mouse. Soft tissues surrounding the joints of the control mice appeared normal. Surfaces of the bones are covered with smooth hyaline cartilage of the uniform thickness. Representative sections through the talus and calcaneum joint of CIA non-treated (25C, 25E, 25G, 25I) and vehicle treated (25D, 25F, 25H, 25J) mouse. Data shown mean±SEM, n=8.

Figure 1:
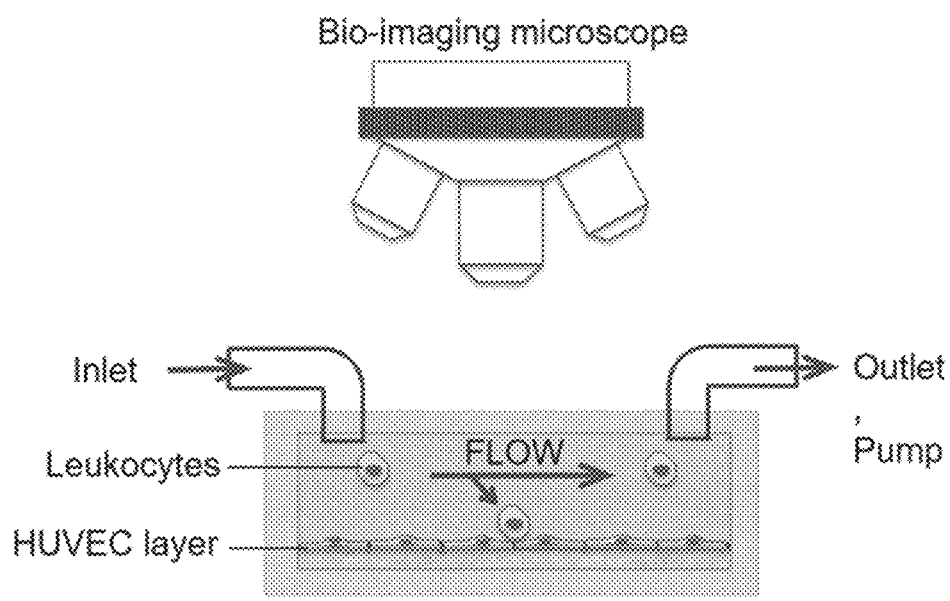
FIG. 1 shows the structure of a flow chamber that was used in the biological assay described in Example 4. Human umbilical vein endothelial cells (HUVECs) were seeded into the flow chamber and cultured for 48-72 hours. Leukocytes were then flowed over the cultured endothelial cells using a calibrated pump. Leukocyte capture, adhesion and migration events were recorded using microscopy and bio-imaging equipment.

According to one aspect of the invention a compound of the general Formula (I) is provided:

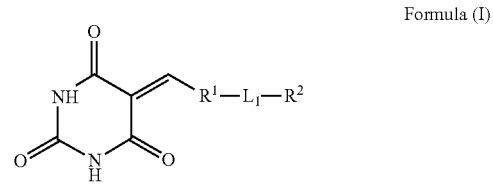

Formula (I)

wherein
$R^1$ is a cyclic or heterocyclic aromatic or non-aromatic moiety, selected from phenyl, naphthyl, anthracenyl, phenanthrenyl, tetracenyl, chrysene, phenanthrene, triphenylene, pyrene, tetrahydrofuran, furan, thiophene, pyrrole, 2H-pyrrole, 2,5-dihydro-1H-pyrrole, pyrrolidine, oxazole, thiazole, imidazole, 4,5-dihydro-1H-imidazole, imidazoline, pyrazole, 4,5-dihydro-1H-pyrazole, pyrazoline, isoxazole, isothiazole, 1,2,3-oxadiazole, 1,3,4-oxadiazole, 1,2,4-oxadiazole, 1,2,3-thiadiazole, 1,2,3-triazole, 1,2,4-triazole, tetrazole, 1,2,3,4-oxatriazole, 2H-Pyran, 3,4-dihydro-2H-pyran, 1,4-dioxane, morpholine, piperidine, piperazine, pyridine, pyrazine, pyrimidine, pyridazine, benzofuran, benzothiophene, benzoxazole, benzothiazole, indole, indolin, benzoimidazole indazole, benzotriazole, 1H-pyrrolo-[3,2-b]pyrazine, 1H-pyrrolo-[3,2-c]pyridine, 1,3,5-triazine, pyrrolo-[2,3-c]pyridine, pyrrolo-[2,3-b]pyridine, 7H-pyrrolo-[2,3-d]pyrimidine, 5H-pyrrolo-[3,2-d]pyrimidine, 7H-purine, indolizine, pyrrolo-[1,2-a]pyrimidine, pyrrolo-[1,2-a]pyrazine, pyrrolo-[1,2-c]pyrimidine, pyrrolo-[1,2-b]pyridazine, imidazol[4,5-b]pyridine, pyrazolo[1,5-a]pyridine, imidazo[1,5-a]pyridine, imidazo[1,5-b]pyridazine, imidazo[1,2-a]pyridine, imidazo[1,2-b]pyridazine, imidazo[1,2-c]pyrimidine, imidazo[1,2-a]pyrazine, imidazo[1,2-a]pyrimidine, [1,2,3]triazolo[4,3-a]pyridine, [1,2,3]triazolo[1,5-a]pyridine, quinoline, isoquinoline, cinnoline, quinazoline, quinoxaline, phthalazine, pyrido[2,3-b]pyrazine, pteridine, pyrido[3,4-d]pyridazine, 1,6-naphthyridine, 1,8-naphthyridine, 9H-carbazole, dibenzofuran and dibenzothiophene, and wherein $R^1$ is unsubstituted or $R^1$ is substituted with one or more of Z;

Z is independently one or more of functional groups selected from linear or branched: S-alkyl, N-alkyl, O-alkyl, alkyl, alkenyl, and aryl, each of which may be unsubstituted or substituted with one or more of halo, haloalkyl, cyano, nitro, hydroxyl, alkenyl, aryl, alkoxy, aryloxy, aralkoxy, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, carboxylic ester, alkoxycarbonyl, aryloxycarbonyl, sulfo, alkylsulfonylamido, alkylsulfonyl, arylsulfonyl, alkylsulfinyl, arylsulfinyl; wherein Z also represents direct substitutions in any aromatic positions of each of $R^1$ and/or $R^2$ by S-alkyl, N-alkyl, O-alkyl, alkyl, alkenyl, aryl, halo, haloalkyl, cyano, nitro, hydroxyl, alkoxy, aryloxy, aralkoxy, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, carboxylic ester, alkoxycarbonyl, aryloxycarbonyl, sulfo, alkylsulfonylamido, alkylsulfonyl, arylsulfonyl, alkylsulfinyl, arylsulfinyl, sulfonylimide, sulfone; and wherein each of Z is the same or different at each occurrence thereof on $R^1$ and/or $R^2$;

$L_1$ is a bivalent linking group, which may be absent or present, but if present is selected from alkoxy and alkyl, wherein each of the alkoxy and alkyl are unsubstituted or substituted with one or several hydroxyl, amino, cyano, thiol, oxo group, thioxo, linear thioether, amide, aryloxy, aralkoxy, alkylcarbamido, arylcarbamido, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl, alkene, or alkyne;

$R^2$ may be absent or present, but if present is phenyl substituted with a group selected from carboxyl group (—COOH) and carboxylic ester group (—CO(=O)$R^5$), wherein the carboxyl group or the carboxylic ester group is present at the para, ortho or meta position to $L_1$, and wherein $R^2$ is optionally further substituted with one or more of Z;

$R^5$ is hydrogen, linear alkyl, branched alkyl, linear alkenyl or branched alkenyl, wherein each of the alkyl and the alkenyl may be unsubstituted or substituted with one, two, or three substituents selected from the group consisting of halo, nitro, cyano and amino; and stereoisomers, enantiomers, and tautomers thereof, pharmaceutically acceptable salts thereof, and mixtures thereof.

In some embodiments of the compounds of general Formula (I) each of $R^1$, $L_1$ and $R^2$ is present; $R^1$ is unsubstituted phenyl or phenyl substituted with one or more of Z, and when $R^1$ is substituted at least one of Z is linear alkyl or branched alkyl; Z is the same or different at each occurrence thereof on $R^1$ and/or $R^2$; and $L_1$ is a bivalent alkoxy linking group.

According to another aspect of the invention a compound of the general Formula (Ia) is provided:

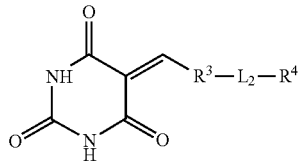

Formula (Ia)

wherein $R^3$ is cyclic aromatic group, selected from phenyl, naphthyl, anthracenyl, phenanthrenyl, tetracenyl, chrysene, phenanthrene, triphenylene, pyrene; wherein $R^3$ is unsubstituted or $R^3$ is substituted with one or more of Z; preferably $R^3$ is unsubstituted phenyl or phenyl substituted with one or more of Z;

Z is independently one or more of functional groups selected from linear or branched: S-alkyl, N-alkyl, O-alkyl, alkyl, alkenyl and aryl, each of which may be unsubstituted or substituted with one or more of halo, haloalkyl, cyano, nitro, hydroxyl, alkenyl, aryl, alkoxy, aryloxy, aralkoxy, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, carboxylic ester, alkoxycarbonyl, aryloxycarbonyl, sulfo, alkylsulfonylamido, alkylsulfonyl, arylsulfonyl, alkylsulfinyl, arylsulfinyl;

wherein Z also represents direct substitutions in any aromatic positions of each of $R^3$ and/or $R^4$ by S-alkyl, N-alkyl, O-alkyl, alkyl, alkenyl, aryl, halo, haloalkyl, cyano, nitro, hydroxyl, aryloxyl, aralkoxy, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, carboxylic ester, alkoxycarbonyl, aryloxycarbonyl, sulfo, alkylsulfonylamido, alkylsulfonyl, arylsulfonyl, alkylsulfinyl, arylsulfinyl, sulfonylimide and sulfone; and wherein each of Z is the same or different at each occurrence thereof on $R^3$ and/or $R^4$;

$L_2$ is a bivalent alkoxy linking group, which is unsubstituted or substituted with one or more of hydroxyl, amino, cyano, thiol, oxo or thioxo group, preferably $L_2$ is —O—$C_{1-4}$alkylene-, most preferably $L_2$ is —O—$CH_2$—;

$R^4$ is phenyl substituted with a group selected from carboxyl group (—COOH) and carboxylic ester group (—CO(=O)$R^5$), wherein the carboxyl group or the carboxylic ester group is present at the para, ortho or meta position to $L_2$, and wherein $R^4$ is optionally further substituted with one or more of Z;

$R^5$ is hydrogen, linear alkyl, branched alkyl, linear alkenyl or branched alkenyl, wherein each of the alkyl and the alkenyl may be unsubstituted or substituted with one, two, or three substituents selected from the group consisting of halo, nitro, cyano and amino; and stereoisomers, enantiomers, and tautomers thereof, pharmaceutically acceptable salts thereof, and mixtures thereof.

In some embodiments of the compound of general Formula (Ia), $R^3$ is unsubstituted phenyl or phenyl substituted with one or more of Z.

In some embodiments of the compound of general Formula (Ia), $R^3$ is unsubstituted phenyl or phenyl substituted with one or more of Z; $L_2$ is unsubstituted bivalent alkoxy linking group, preferably $L_2$ is —O—$C_{1-4}$alkylene-; each Z is the same or different at each occurrence thereof on $R^3$ and/or $R^4$; the bonds to the barbituric acid moiety and to $L_2$ on $R^3$ are located ortho to each other, and the bond to the carboxylic acid group or to the carboxylic acid ester group of $R^4$ is located para to the linking group ($L_2$).

In other embodiments of the compound of general Formula (Ia), $R^3$ is unsubstituted phenyl or phenyl substituted with one or more of Z; $L_2$ is unsubstituted bivalent alkoxy linking group, preferably $L_2$ is —O—$C_{1-4}$alkylene-; each Z is the same or different at each occurrence thereof on $R^3$ and/or $R^4$; the bonds to the barbituric acid moiety and to $L_2$ on $R^3$ are located meta to each other, and the bond to the carboxylic acid group or to the carboxylic acid ester group of $R^4$ is located para to the linking group ($L_2$).

In some embodiments of the compound of general Formula (Ia), $R^3$ is unsubstituted phenyl or phenyl substituted with one or more of Z; $L_2$ is unsubstituted bivalent alkoxy linking group, preferably $L_2$ is —O—$C_{1-4}$alkylene-; each Z is the same or different at each occurrence thereof on $R^3$ and/or $R^4$; the bonds to the barbituric moiety and to $L_2$ on $R^3$ are located para to each other, and the bond to the carboxylic acid group or to the carboxylic acid ester group of $R^4$ is located para to the linking group ($L_2$).

In some embodiments of the compound of general Formula (Ia), $R^3$ is unsubstituted phenyl or phenyl substituted with one or more of Z; $L_2$ is unsubstituted bivalent alkoxy linking group, preferably $L_2$ is —O—$C_{1-4}$alkylene-; each Z is the same or different at each occurrence thereof on $R^3$ and/or $R^4$; the bonds to the barbituric acid moiety and to $L_2$ on $R^3$ are located ortho to each other, and the bond to the carboxylic acid group or to the carboxylic acid ester group of $R^4$ is located meta to the linking group ($L_2$).

In some embodiments of the compound of general Formula (Ia), $R^3$ is unsubstituted phenyl or phenyl substituted with one or more of Z; $L_2$ is unsubstituted bivalent alkoxy linking group, preferably $L_2$ is —O—$C_{1-4}$alkylene-; each Z is the same or different at each occurrence thereof on $R^3$ and/or $R^4$; the bonds to the barbituric acid moiety and to $L_2$ on $R^3$ are located para to each other, and the bond to the carboxylic acid group or to the carboxylic acid ester group of $R^4$ is located meta to the linking group ($L_2$).

In some embodiments of the compound of general Formula (Ia), $R^3$ is unsubstituted phenyl or phenyl substituted with one or more of Z; $L_2$ is unsubstituted bivalent alkoxy linking group, preferably $L_2$ is —O—$C_{1-4}$alkylene-; each Z is the same or different at each occurrence thereof on $R^3$ and/or $R^4$; the bonds to the barbituric acid moiety and to $L_2$ on $R^3$ are located meta to each other, and the bond to the carboxylic acid group or to the carboxylic acid ester group of $R^4$ is located meta to the linking group ($L_2$).

According to another aspect of the invention a compound of the general Formula (Ib) is provided:

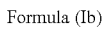

Formula (Ib)

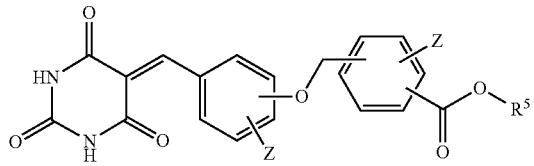

wherein

Z is present or absent, and when present is for each phenyl ring independently one or several, and if several preferably 2, functional groups; each Z is attached to any available carbon atom of the ring in which it is present; and at each occurrence Z is independently selected from linear alkyl or branched alkyl, wherein each of the linear alkyl or the branched alkyl may be unsubstituted or substituted with one or more of halo, haloalkyl, cyano, nitro, hydroxyl, alkenyl, aryl, alkoxy, aryloxy, aralkoxy, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, carboxylic ester, alkoxycarbonyl, aryloxycarbonyl, sulfo, alkylsulfonylamido, alkylsulfonyl, arylsulfonyl, alkylsulfinyl, arylsulfinyl;

$R^5$ is hydrogen, linear alkyl, branched alkyl, linear alkenyl or branched alkenyl, wherein each of the alkyl or the alkenyl may be unsubstituted or substituted with one, two, or three substituents selected from the group consisting of halo, nitro, cyano and amino; and stereoisomers, enantiomers, and tautomers thereof, pharmaceutically acceptable salts thereof and mixtures thereof.

In various embodiments of the compound of general Formula (Ib), each Z is attached to any available carbon atom of the ring in which it is present and at each occurrence Z is independently selected as defined immediately above.

In some embodiments of the compounds of general Formula (Ib), Z is absent.

In other embodiments of the compounds of general Formula (Ib), at least one Z is present.

In some preferred embodiments of the compounds of general Formula (Ib), one Z is present.

In some embodiments of the compound of general Formula (Ib), at least one Z is present, and is selected from unsubstituted linear alkyl or unsubstituted branched alkyl. In some embodiments of the compound of general Formula (Ib), one Z is present, and is selected from unsubstituted linear alkyl or unsubstituted branched alkyl.

In some embodiments of the compound of general Formula (Ib), one or several Z are present on one ring and Z is absent on the other ring. In some embodiments of the compound of general Formula (Ib), one or two Z are present on one ring and Z is absent on the other ring.

In some embodiments of the compound of general Formula (Ib), one or several Z are present on both rings. In some embodiments of the compound of general Formula (Ib) one or two Z are present on both rings.

In some embodiments of the compound of general Formula (Ib), one or several Z are present on the phenyl ring connected to the barbituric moiety and Z is absent on the other ring. In some embodiments of the compound of general Formula (Ib) one or two Z are present on the phenyl ring connected to the barbituric moiety and Z is absent on the other ring.

In some embodiments of the compound of general Formula (Ib), at least two Z are present and both are independently selected from unsubstituted linear alkyl or unsubstituted branched alkyl. In some embodiments of the compound of general Formula (Ib), two Z are present and both are independently selected from unsubstituted linear alkyl or unsubstituted branched alkyl.

In some embodiments of the compound of general Formula (Ib), at least two Z are present on the same phenyl ring and both are independently selected from unsubstituted linear alkyl or unsubstituted branched alkyl. In some embodiments of the compound of general Formula (Ib), two Z are present on the same phenyl ring and both are independently selected from unsubstituted linear alkyl or unsubstituted branched alkyl.

In various embodiments of the compound of general Formula (Ib), each Z is independently selected from unsubstituted linear alkyl or unsubstituted branched alkyl, having 1 to 6 carbon atoms ($C_{1-6}$alkyl), selected from methyl, ethyl, n-propyl, iso-propyl, butyl, iso-butyl, sec-butyl, tert-butyl, n-pentyl, iso-pentyl, neo-pentyl, tert-pentyl, n-hexyl, and iso-hexyl. In some preferred embodiments each Z is independently selected from unsubstituted linear alkyl or unsubstituted branched alkyl, having 1 to 4 carbon atoms ($C_{1-4}$alkyl), selected from methyl, ethyl, n-propyl, iso-propyl, butyl, iso-butyl, sec-butyl, tert-butyl.

In some embodiments of the compound of general Formula (Ib), one or several Z are present on the ring connected to the barbituric moiety and Z is absent on the other ring; and each Z is independently selected from unsubstituted linear alkyl or unsubstituted branched alkyl. Preferably each Z is independently selected from unsubstituted linear alkyl or unsubstituted branched alkyl, having 1 to 6 carbon atoms ($C_{1-6}$alkyl), selected from methyl, ethyl, n-propyl, iso-propyl, butyl, iso-butyl, sec-butyl, tert-butyl, n-pentyl, iso-pentyl, neo-pentyl, tert-pentyl, n-hexyl, and iso-hexyl. Most preferably each Z is independently selected from unsubstituted linear alkyl or unsubstituted branched alkyl, having 1 to 4 carbon atoms ($C_{1-4}$alkyl), selected from methyl, ethyl, n-propyl, iso-propyl, butyl, iso-butyl, sec-butyl, tert-butyl.

In some embodiments of the compound of general Formula (Ib), Z is absent on the ring connected to the barbituric moiety and one or several Z are present on the other ring; and each Z is independently selected from unsubstituted linear alkyl or unsubstituted branched alkyl. Preferably each Z is independently selected from unsubstituted linear alkyl or unsubstituted branched alkyl, having 1 to 6 carbon atoms ($C_{1-6}$alkyl), selected from methyl, ethyl, n-propyl, iso-propyl, butyl, iso-butyl, sec-butyl, tert-butyl, n-pentyl, iso-pentyl, neo-pentyl, tert-pentyl, n-hexyl, and iso-hexyl. Most preferably each Z is independently selected from unsubstituted linear alkyl or unsubstituted branched alkyl, having 1 to 4 carbon atoms ($C_{1-4}$alkyl), selected from methyl, ethyl, n-propyl, iso-propyl, butyl, iso-butyl, sec-butyl, tert-butyl.

In some embodiments of the compound of general Formula (Ib) $R^5$ is hydrogen.

In some embodiments of the compound of general Formula (Ib) $R^5$ is alkyl, selected from linear alkyl or branched alkyl, wherein the alkyl is unsubstituted or wherein the alkyl is substituted with one, two, or three substituents selected from the group consisting of halo, nitro, cyano and amino. In some preferred embodiments $R^5$ is selected from linear alkyl or branched alkyl, having 1 to 6 carbon atoms ($C_{1-6}$alkyl), such as methyl, ethyl, n-propyl, iso-propyl, butyl, iso-butyl, sec-butyl, tert-butyl, n-pentyl, iso-pentyl, neo-pentyl, tert-pentyl, n-hexyl, and iso-hexyl. In some preferred embodiments $R^5$ is selected from unsubstituted linear alkyl or unsubstituted branched alkyl, having 1 to 4 carbon atoms ($C_{1-4}$alkyl), selected from methyl, ethyl, n-propyl, iso-propyl, butyl, iso-butyl, sec-butyl, tert-butyl.

In various embodiments of the compound of general Formula (Ib) the carboxylic group —CO(=O)$R^5$ is present at the para, meta or ortho position to the linking group —O—$CH_2$—.

In various embodiments of the compound of general Formula (Ib) the bonds to the barbituric acid moiety and to the linking group —O—$CH_2$— are located para, meta or ortho to each other.

In some embodiments of the compound of general Formula (Ib), the bonds to the barbituric acid moiety and to the linking group —O—$CH_2$— are located ortho to each other, and the bond to the carboxylic group —CO(=O)$R^5$ is located para to the bond to the linking group —O—$CH_2$—.

In some embodiments of the compound of general Formula (Ib), the bonds to the barbituric acid moiety and to the linking group —O—$CH_2$— are located meta to each other, and the bond to the carboxylic group —CO(=O)$R^5$ is located para to the bond to the linking group —O—$CH_2$—.

In some embodiments of the compound of general Formula (Ib), the bonds to the barbituric acid moiety and to the linking group —O—$CH_2$— are located para to each other, and the bond to the carboxylic group —CO(=O)$R^5$ is located para to the bond to the linking group —O—$CH_2$—.

In some embodiments of the compound of general Formula (Ib), the bonds to the barbituric acid moiety and to the linking group —O—$CH_2$— are located ortho to each other, and the bond to the carboxylic group —CO(=O)$R^5$ is located meta to the bond to the linking group —O—$CH_2$—.

In some embodiments of the compound of general Formula (Ib), the bonds to the barbituric acid moiety and to the linking group —O—$CH_2$— are located para to each other, and the bond to the carboxylic group —CO(=O)$R^5$ is located meta to the bond to the linking group —O—$CH_2$—.

In some embodiments of the compound of general Formula (Ib), the bonds to the barbituric acid moiety and to the linking group —O—$CH_2$— are located meta to each other, and the bond to the carboxylic group —CO(=O)$R^5$ is located meta to the bond to the linking group —O—$CH_2$—.

Table 1 provides non-limiting examples of compounds of general Formula (Ib). It includes compounds as follows: Methyl 4-((3-((2,4,6-trioxo-tetrahydropyrimidin-5(2H)-ylidene) methyl)phenoxy)methyl) benzoate (Formula 1), methyl 4-((2-(tert-butyl)-6-((2,4,6-trioxotetrahydropyrimidin-5(2H)-ylidene)methyl)phenoxy)methyl) benzoate (Formula 2), methyl 4-((2-((2,4,6-trioxo-tetrahydropyrimidin-5 (6H)-ylidene)methyl)phenoxy)methyl)benzoate (Formula 3), Methyl 4-((2,6-dimethyl-4-((2,4,6-trioxotetrahydro-pyrimidin-5(2H)ylidene)methyl) phenoxy)methyl) benzoate (Formula 4), Methyl 3-((2-((2,4,6-trioxo-tetrahydropyrimidin-5(6H)-ylidene)methyl)phenoxy)methyl)benzoate (Formula 5), 3-((2-((2,4,6-trioxo-tetrahydropyrimidin-5(6H)-ylidene)methyl)phenoxy)methyl)benzoic acid (Formula 6), Methyl 3-((4-((2,4,6-trioxotetra-hydropyrimidin-5(2H)-ylidene)methyl)phenoxy) methyl)benzoate (Formula 7), 3-((4-((2,4,6-trioxotetrahydro-pyrimidin-5(2H)ylidene) methyl)phenoxy)methyl) benzoic acid (Formula 8), and Methyl 3-((3-((2,4,6-trioxo-tetrahydropyrimidin-5(2H)-ylidene)methyl)phenoxy)methyl) benzoate (Formula 9).

TABLE 1

| Formula # | Structure | Name |
| --- | --- | --- |
| 1 | 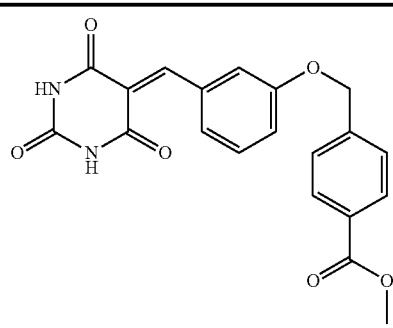 | Methyl 4-((3-((2,4,6-trioxo-tetrahydropyrimidin-5(2H)-ylidene)methyl) phenoxy)methyl) benzoate |

TABLE 1-continued

| Formula # | Structure | Name |
|---|---|---|
| 2 | 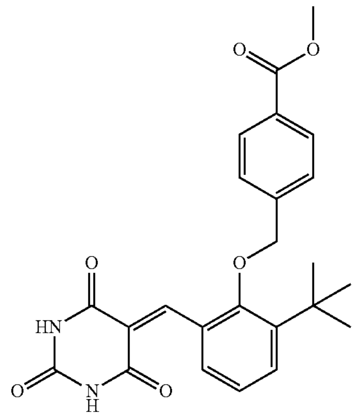 [SMILES: COC(=O)c1ccc(COc2c(C=C3C(=O)NC(=O)NC3=O)cccc2C(C)(C)C)cc1] | Methyl 4-((2-(tert-butyl)-6-((2,4,6-trioxotetrahydro-pyrimidin-5(2H)-ylidene)methyl) phenoxy)methyl) benzoate |
| 3 | 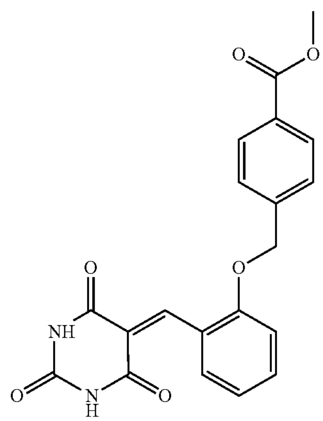 [SMILES: COC(=O)c1ccc(COc2ccccc2C=C2C(=O)NC(=O)NC2=O)cc1] | Methyl 4-((2-((2,4,6-trioxo-tetrahydropyrimidin-5(6H)-ylidene)methyl)phenoxy)methyl)benzoate |
| 4 | 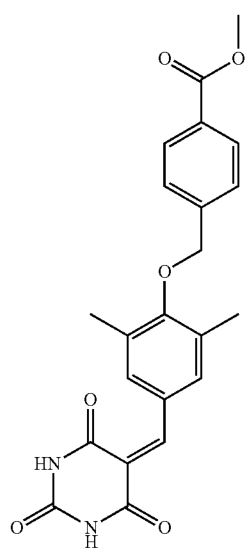 | Methyl 4-((2,6-dimethyl-4-((2,4,6-trioxotetrahydro-pyrimidin-5(2H)ylidene)methyl) phenoxy)methyl) benzoate |

TABLE 1-continued
| Formula # | Structure | Name |
|---|---|---|
| 5 | 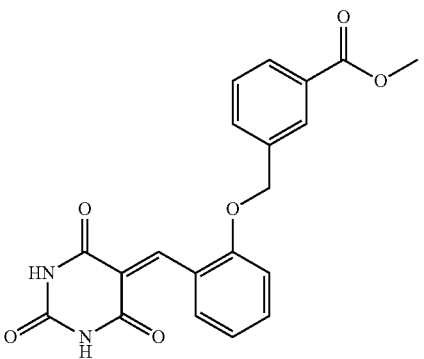 [SMILES: COC(=O)c1cccc(COc2ccccc2C=C2C(=O)NC(=O)NC2=O)c1] | Methyl 3-((2-((2,4,6-trioxo-tetrahydropyrimidin-5(6H)-ylidene)methyl)phenoxy)methyl)benzoate |
| 6 | 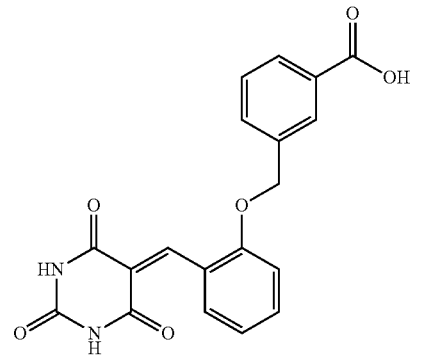 [SMILES: O=C1NC(=O)C(=Cc2ccccc2OCc2cccc(C(=O)O)c2)C(=O)N1] | 3-((2-((2,4,6-trioxo-tetrahydropyrimidin-5(6H)-ylidene)methyl)phenoxy)methyl)benzoic acid |
| 7 | 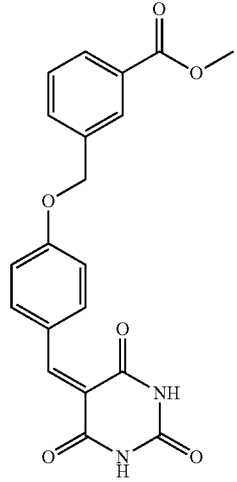 [SMILES: COC(=O)c1cccc(COc2ccc(C=C3C(=O)NC(=O)NC3=O)cc2)c1] | Methyl 3-((4-((2,4,6-trioxotetra-hydropyrimidin-5(2H)-ylidene) methyl) phenoxy) methyl) benzoate |

TABLE 1-continued

| Formula # | Structure | Name |
|---|---|---|
| 8 | 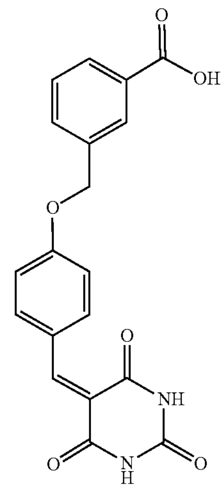 [SMILES: O=C1NC(=O)C(=Cc2ccc(OCc3cccc(C(=O)O)c3)cc2)C(=O)N1] | 3-((4-((2,4,6-trioxotetrahydro-pyrimidin-5(2H)ylidene)methyl) phenoxy) methyl) benzoic acid |
| 9 | 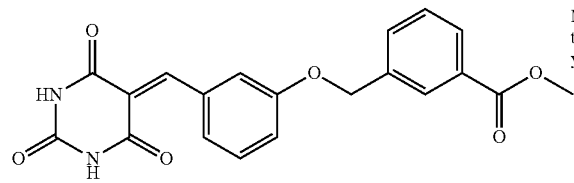 [SMILES: COC(=O)c1cccc(COc2cccc(C=C3C(=O)NC(=O)NC3=O)c2)c1] | Methyl 3-((3-((2,4,6-trioxo-tetrahydropyrimidin-5(2H)-ylidene)methyl)phenoxy)methyl) benzoate |

In another aspect provided herein is a compound of general Formula (I) in which $R^1$ is present and each of $L_1$ and $R^2$ are absent, having the general Formula (Ic):

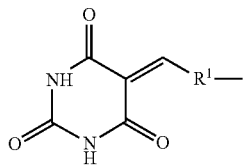

Formula (Ic)

wherein, $R^1$ is selected from naphthyl, phenanthrenyl, tetracenyl, chrysene, phenanthrene, triphenylene, pyrene, tetrahydrofuran, furan, thiophene, pyrrole, 2H-pyrrole, 2,5-dihydro-1H-pyrrole, pyrrolidine, oxazole, thiazole, imidazole, 4,5-dihydro-1H-imidazole, imidazoline, pyrazole, 4,5-dihydro-1H-pyrazole, pyrazoline, isoxazole, isothiazole, 1,2,3-oxadiazole, 1,3,4-oxadiazole, 1,2,4-oxadiazole, 1,2,3-thiadiazole, 1,2,3-triazole, 1,2,4-triazole, tetrazole, 1,2,3,4-oxatriazole, 2H-pyran, 3,4-dihydro-2H-pyran, 1,4-dioxane, morpholine, piperidine, piperazine, pyridine, pyrazine, pyrimidine, pyridazine, benzofuran, benzothiophene, benzoxazole, benzothiazole, indole, indolin, benzoimidazole indazole, benzotriazole, 1H-pyrrolo-[3,2-b]pyrazine, 1H-pyrrolo-[3,2-c]pyridine, 1,3,5-triazine, pyrrolo-[2,3-c]pyridine, pyrrolo-[2,3-b]pyridine, 7H-pyrrolo-[2,3-d]pyrimidine, 5H-pyrrolo-[3,2-d]pyrimidine, 7H-purine, indolizine, pyrrolo-[1,2-a]pyrimidine, pyrrolo-[1,2-a]pyrazine, pyrrolo-[1,2-c]pyrimidine, pyrrolo-[1,2-b]pyridazine, imidazol[4,5-b]pyridine, pyrazolo[1,5-a]pyridine, imidazo[1,5-a]pyridine, imidazo[1,5-b]pyridazine, imidazo[1,2-a]pyridine, imidazo[1,2-b]pyridazine, imidazo[1,2-c]pyrimidine, imidazo[1,2-a]pyrazine, imidazo[1,2-a]pyrimidine, [1,2,3]triazolo[4,3-a]pyridine, [1,2,3]triazolo[1,5-a]pyridine, quinoline, isoquinoline, cinnoline, quinazoline, quinoxaline, phthalazine, pyrido[2,3-b]pyrazine, pteridine, pyrido[3,4-d]pyridazine, 1,6-naphthyridine, 1,8-naphthyridine, 9H-carbazole, dibenzofuran and dibenzothiophene, and wherein $R^1$ is unsubstituted or substituted with one or more of Z; or wherein $R^1$ is anthracenyl substituted with one or more of Z; and wherein Z is independently one or more of functional groups selected from linear or branched: S-alkyl, N-alkyl, O-alkyl, alkyl, alkenyl and aryl, each of which may be unsubstituted or substituted with one or more of halo, haloalkyl, cyano, nitro, hydroxyl, alkenyl, aryl, alkoxy, aryloxy, aralkoxy, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, carboxylic ester, alkoxycarbonyl, aryloxycarbonyl, sulfo, alkylsulfonylamido, alkylsulfonyl, arylsulfonyl, alkylsulfinyl, arylsulfinyl; wherein Z also represents direct substitutions in any aromatic position of each of $R^1$ by S-alkyl, N-alkyl, O-alkyl, alkyl, alkenyl, aryl, halo, haloalkyl, cyano, nitro, hydroxyl, aryloxy, aralkoxy, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, carboxylic ester, alkoxycarbonyl, aryloxycarbonyl, sulfo, alkylsulfonylamido, alkylsulfonyl, arylsulfonyl, alkylsulfinyl, arylsulfinyl, sulfonylimide and sulfone; and stereoisomers, enantiomers, and tautomers thereof, pharmaceutically acceptable salts thereof and mixtures thereof.

The invention also relates to the stereoisomers, enantiomers, mixtures thereof, and salts, particularly the physiologically acceptable salts, of the specific embodiments of compounds of general Formulae (I), (Ia), (Ib) and (Ic) according to the invention, such as, for example, the compounds of structural Formulae 1, 2, 3, 4, 5, 6, 7, 8 and 9.

Some terms used herein to describe the compounds according to the invention are defined more specifically below.

The term "alkyl" refers to a saturated, branched or unbranched (straight chain) hydrocarbon group with 1 to 12 carbon (C) atoms ($C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, $C_{10}$-alkyl, $C_{11}$-alkyl or $C_{12}$-alkyl). Non-limiting examples of such groups include methyl ($C_1$-alkyl), ethyl ($C_2$-alkyl), n-propyl ($C_3$-alkyl), iso-propyl ($C_3$-alkyl), butyl ($C_4$-alkyl), iso-butyl ($C_4$-alkyl), sec-butyl ($C_4$-alkyl), tert-butyl ($C_4$-alkyl), n-pentyl ($C_5$-alkyl), iso-pentyl ($C_5$-alkyl), neo-pentyl ($C_5$-alkyl), tert-pentyl ($C_5$-alkyl), n-hexyl ($C_6$-alkyl), iso-hexyl ($C_6$-alkyl), and so forth.

Similarly, the terms "alkenyl" and "alkynyl", denote unsaturated, branched or unbranched hydrocarbon groups with 2 to 12 (2, 3, 4, 5, 6, 7, 8, 9, 10, 11 or 12) carbon (C) atoms that contain at least one carbon-carbon double bond and carbon-carbon triple bond, respectively. Alkenyl groups of 2 to 6 carbon atoms and having one double bond are most preferred. Alkynyl groups of 2 to 6 carbon atoms and having one triple bond are most preferred.

The term "alkoxy", refers to an alkyl or substituted alkyl group as defined hereinabove, having one, two or three oxygen atoms (—O—) in the alkyl chain. Alkoxy groups of 1 to 6 (1, 2, 3, 4, 5, or 6) carbon atoms and having one oxygen atom in the alkyl chain are most preferred.

The alkyl, alkene or alkoxy groups may be monovalent or bivalent, with valency denoting the ability to combine with another group. Thus, by "monovalent" it is meant that the group has a valency of one, and by "bivalent" it is meant that the group has a valency of two.

Non-limiting examples of a monovalent alkoxy groups include: —O—$C_1$alkyl, —O—$C_2$alkyl, —O—$C_3$alkyl, —O—$C_4$alkyl, —O—$C_5$alkyl, —O—$C_6$alkyl, —O—$C_7$alkyl, —O—$C_8$alkyl, —O—$C_9$alkyl, —O—$C_{10}$alkyl, —O—$C_{11}$alkyl or —O—$C_{12}$alkyl. Non-limiting examples of a bivalent alkoxy include groups such as —O—$C_1$alkylene- (e.g. —O—$CH_2$—), —O—$C_2$alkylene- (e.g. —O—$C_2H_4$—), —O—$C_3$alkylene-, —O—$C_4$alkylene-, —O—$C_5$alkylene-, —O—$C_6$alkylene-, —O—$C_7$alkylene-, —O—$C_8$alkylene-, —O—$C_9$alkylene-, —O—$C_{10}$alkylene-, —O—$C_{11}$alkylene-, or —O—$C_{12}$alkylene-.

The term "halo", as used herein refers to atom selected from among fluoro, chloro, bromo, and iodo (F, Cl, Br and I), preferably Cl and Br.

The term "haloalkyl" refers to a substituted alkyl having one or more halo substituents. For example, "haloalkyl" includes mono-, bi-, and trifluoromethyl.

According to another aspect of the invention, provided herein is a process for the preparation of a compounds of general Formulae (I), (Ia), (Ib) and (Ic). The compounds of general Formulae (I), (Ia), (Ib) and (Ic) according to the invention may be obtained using known methods of synthesis, as described in the literature, utilizing reaction conditions that are known and suitable for such reactions. Preferably the compounds of general Formula (I), (Ia), (Ib) and (Ic) can be obtained by methods of preparation that are described more fully hereinafter.

Certain compounds of general Formulae (I), (Ia), (Ib) and (Ic) can be prepared as shown in Scheme 1. For example, 4-bromomethylbenzoic acid may be reacted with methyl alcohol in the presence of a catalytic amount of $H_2SO_4$ to obtain the corresponding ester: methyl 4-(bromomethyl)benzoate (as described for example in Vassiliou, S., et al., A synthetic method for diversification of the P1' substituent in phosphinic dipeptides as a tool for exploration of the specificity of the S1' binding pockets of leucine aminopeptidases. Bioorganic & Medicinal Chemistry, 2007. 15(9): p. 3187-3200). The reaction is carried out in suitable solvent, such as a polar or an amphiphilic solvent, for example methanol (MeOH), in the presence of a strong acid, such as for example sulfuric acid ($H_2SO_4$), under reflux for several hours, preferably for about 5 hours.

The resulting benzoate can be purified by flash column chromatography using chloroform as an eluent. The purified benzoate can be reacted with commercial available aldehydes using the procedure described by Zidar, N. et al. (New 5-benzylidenethiazolidin-4-one inhibitors of bacterial MurD ligase: Design, synthesis, crystal structures, and biological evaluation. European Journal of Medicinal Chemistry, 2011. 46(11): p. 5512-5523). The reaction is carried out in the presence of $K_2CO_3$, KI and $CH_3CN$, while heating, preferably at about 70° C., for several hours, preferably for about 5 hours, to provide the intermediate compounds: methyl 4-((2-formylphenoxy)methyl)benzoate (B), methyl 4-(3-formylphenoxy)benzoate (C), methyl 4-((2-(tert-butyl)-6-formylphenoxy)methyl)benzoate (D), methyl 4-((4-formyl-2,6-dimethylphenoxy)methyl)benzoate (E).

The crude product (B-E) can be purified by flash column chromatography using petroleum ether-ethyl acetate (95:5) as an eluent. The purified intermediates are subsequently coupled with barbituric acid, e.g. using a Knoevenagel condensation method (Ma, L., et al., Synthesis and biological evaluation of 5-benzylidenepyrimidine-2,4,6(1H,3H,5H)-trione derivatives for the treatment of obesity-related nonalcoholic fatty liver disease. J Med Chem, 2012. 55(22): p. 9958-72) in the presence of EtOH/$H_2O$ 1:1, preferably under reflux, overnight, to obtain: methyl 4-((3-((2,4,6-trioxotetrahydropyrimidin-5(2H)-ylidene)methyl)phenoxy)methyl)benzoate (Formula 1), methyl 4-((2-(tert-butyl)-6-((2,4,6-trioxotetrahydropyrimidin-5(2H)-ylidene) methyl) phenoxy) methyl) benzoate (Formula 2), methyl 4-((2-((2,4,6-trioxotetrahydro-pyrimidin-5(6H)-ylidene)methyl) phenoxy)methyl)benzoate (Formula 3) and methyl 4-((2,6-dimethyl-4-((2,4,6-trioxotetrahydropyrimidin-5(2H)ylidene) methyl) phenoxy) methyl) benzoate (Formula 4), respectively. Barbituric acid can be synthesized by methods known per se, for example according to the procedure described by Ingle, V. N. et al. (Synthesis and biological activities of glycoconjugated spiro triones. Int. J. PharmTech Res., 2009. 1(3): p. 605-612) from urea and malonic acid in the presence of acetic acid and acetic anhydride.

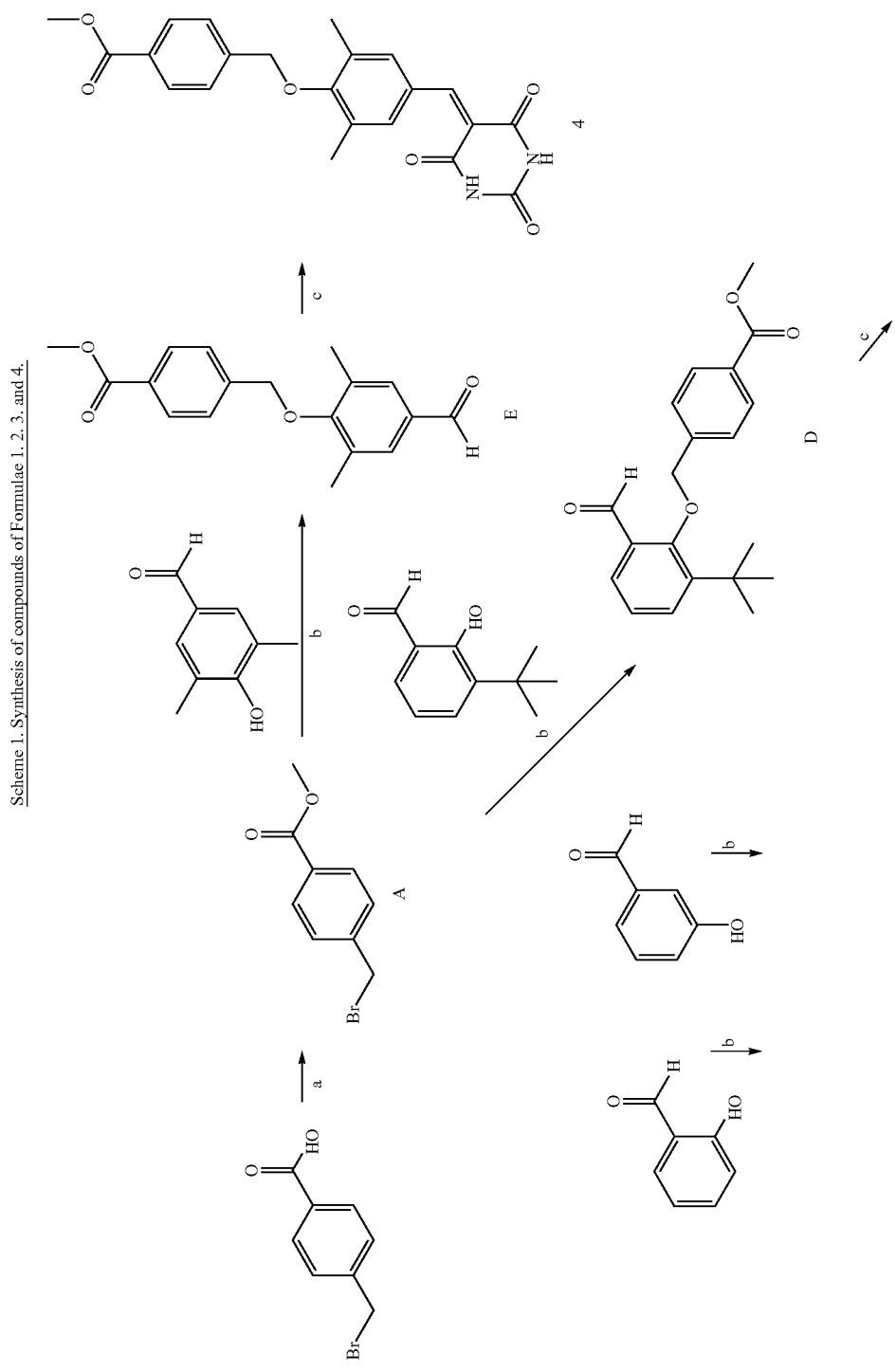
Scheme 1. Synthesis of compounds of Formulae 1, 2, 3, and 4.

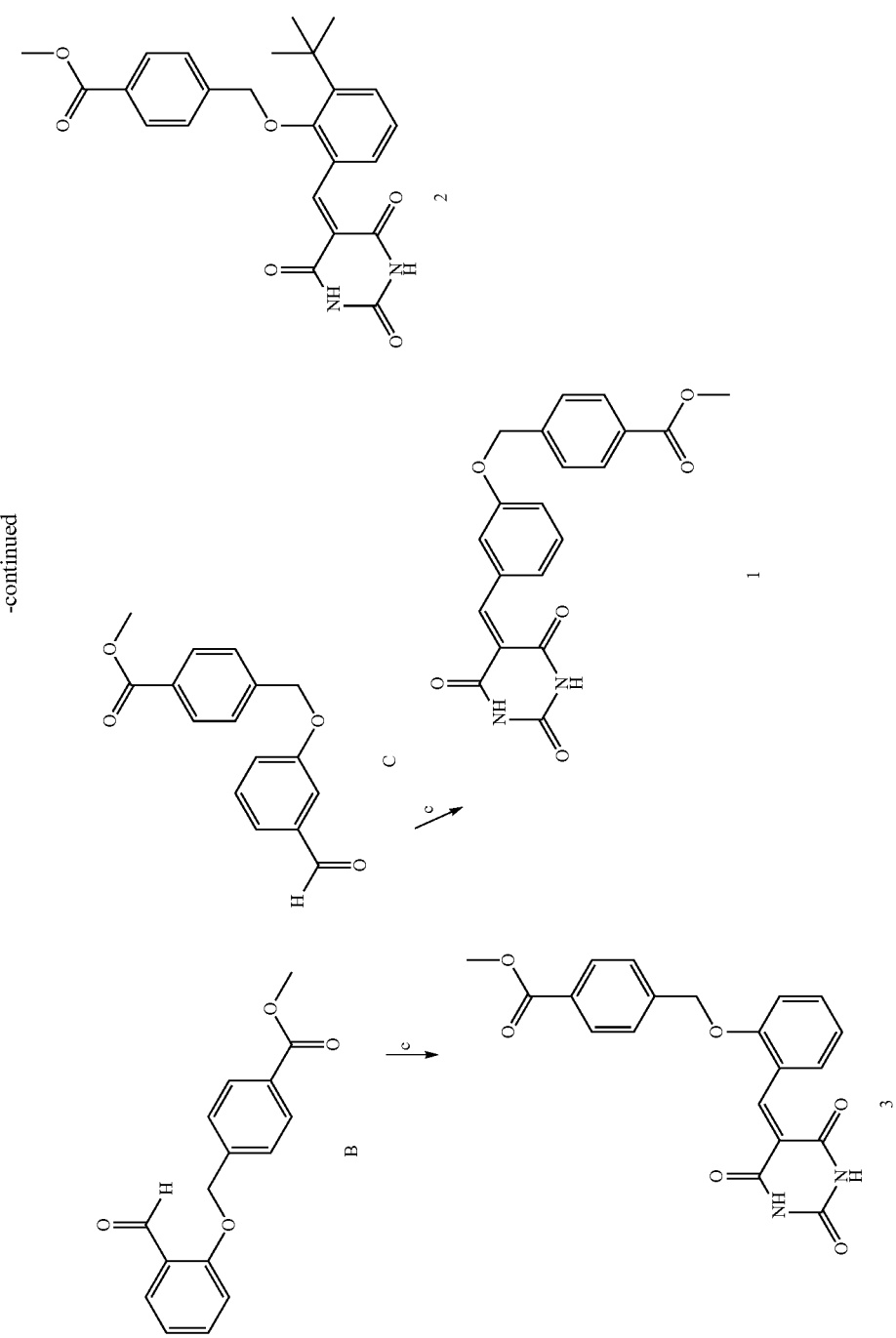

Scheme 1. Synthetic pathways of novel barbituric acid derivative compounds of Formulae 1, 2, 3 and 4: a) MeOH, $H_2SO_4$, reflux 5 hours. b) $K_2CO_3$, KI, $CH_3CN$, 70° C. 5 hours. c) $EtOH/H_2O$ 1:1, barbituric acid, reflux overnight.

Certain compounds of general Formulae (I), (Ia), (Ib) and (Ic) can be prepared as shown in Scheme 2. For example, using as a starting material a 3-(chloromethyl)-benzoic acid, an additional set of novel barbituric acid derivatives of general Formula (I) was synthesized.

Namely, methyl 3-((2-((2,4,6-trioxotetrahydropyrimidin-5(6H)-ylidene) methyl) phenoxy) methyl) benzoate (Formula 5), 3-((2-((2,4,6-trioxotetrahydropyrimidin-5(6H)-ylidene) methyl) phenoxy) methyl) benzoic acid (Formula 6), methyl 3-((4-((2,4,6-trioxotetrahydropyrimidin-5(2H)-ylidene) methyl) phenoxy) methyl) benzoate (Formula 7), 3-((4-((2,4,6-trioxotetrahydropyrimidin-5(2H) ylidene) methyl)phenoxy) methyl) benzoic acid (Formula 8), and methyl 3-((3-((2,4,6-trioxo-tetrahydropyrimidin-5(2H)-ylidene)methyl)phenoxy)methyl) benzoate (Formula 9).

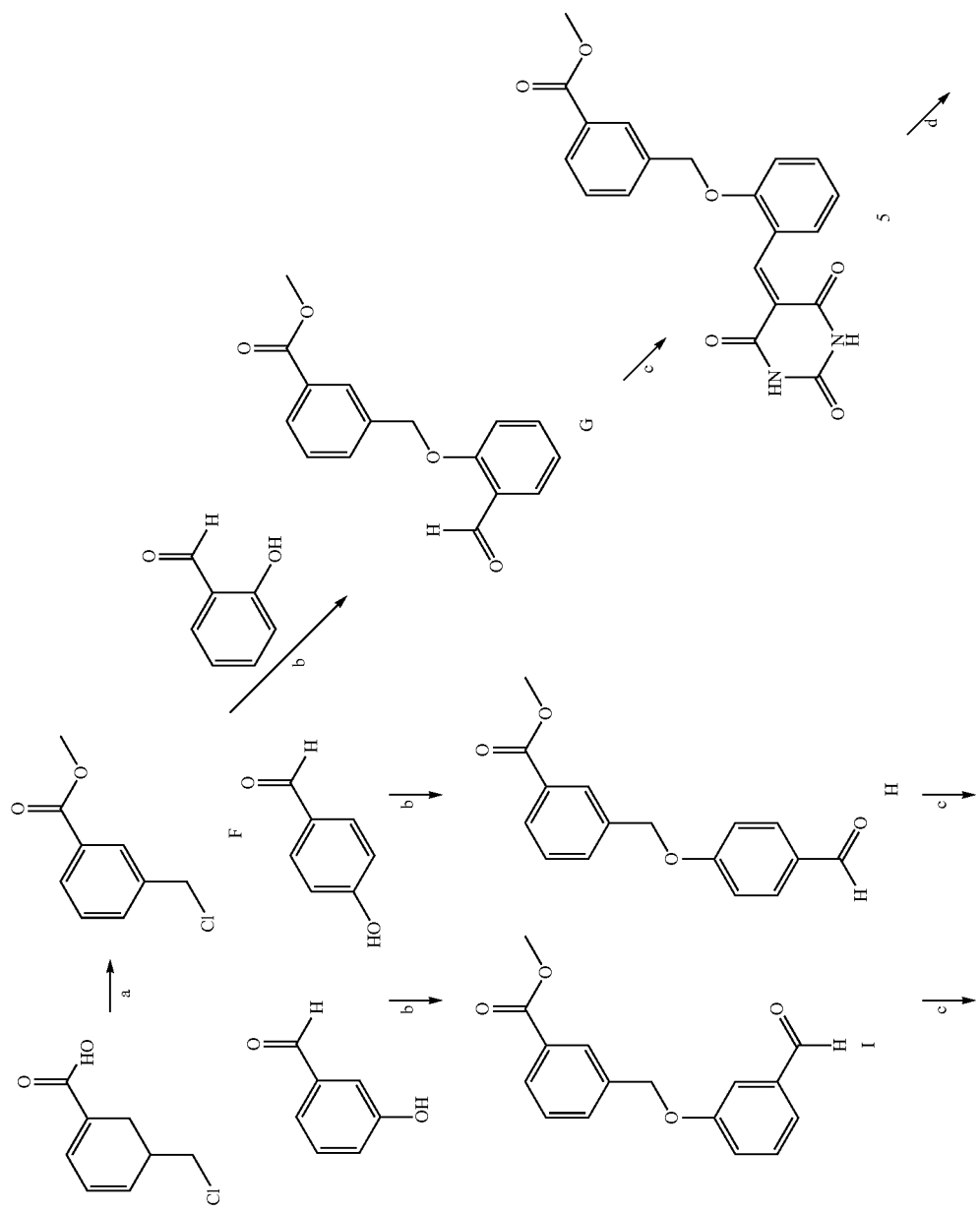
Scheme 2. Synthesis of the compounds of Formulae 5, 6, 7, 8 and 9.

-continued
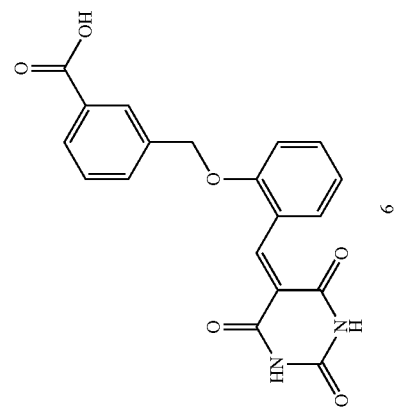
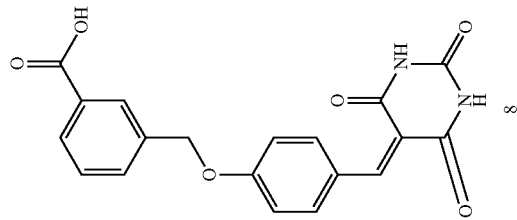
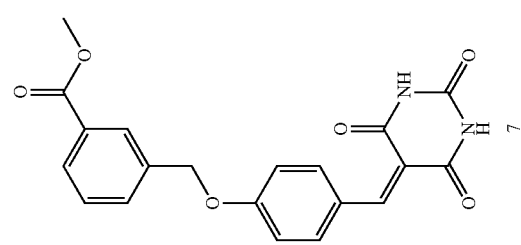
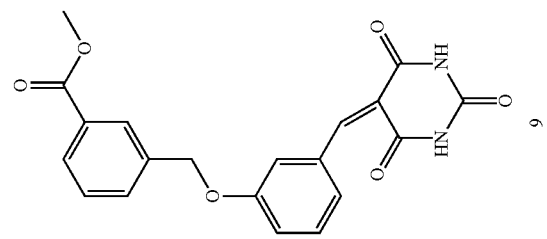

Scheme 2. Synthetic pathways of novel barbituric acid derivative compounds of Formulae 5, 6, 7, 8 and 9: a) MeOH, $H_2SO_4$, reflux 5 hours. b) $K_2CO_3$, KI, aldehyde, $CH_3CN$, 70° C. 5 hours. c) $EtOH/H_2O$ 1:1, barbituric acid, reflux overnight. d) 2M NaOH, 1,4-dixoan:MeOH:$H_2O$/1:1:1, reflux 5 hours.

The invention also relates to the stereoisomers, such as diastereomers and enantiomers, mixtures and salts, particularly the physiologically acceptable salts, of the compounds of general Formulae (I), (Ia), (Ib) and (Ic). The compounds of general Formulae (I), (Ia), (Ib) and (Ic), or intermediate products in the synthesis of compounds of general Formulae (I), (Ia), (Ib) and (Ic), may be resolved into their enantiomers and/or diastereomers on the basis of their physical-chemical differences using methods known in the art. For example, cis/trans mixtures may be resolved into their cis and trans isomers by chromatography. For example, enantiomers may be separated by chromatography on chiral phases or by recrystallization from an optically active solvent or by enantiomer-enriched seeding.

The compounds of general Formulae (I), (Ia), (Ib) and (Ic), and the compounds of structural Formulae 1, 2, 3, 4, 5, 6, 7, 8 and 9, can be used in their final non-salt form. Alternatively, the compounds according to the invention can be converted into the salts thereof, particularly physiologically acceptable salts for pharmaceutical use, which can be obtained from various organic and inorganic acids and bases by procedures known in the art. Suitable salts of the compounds of general Formulae (I), (Ia), (Ib) and (Ic), and of the compounds of structural formulae 1, 2, 3, 4, 5, 6, 7, 8 and 9, may be formed with organic or inorganic acids, such as, without being limited to hydrochloric acid, hydrobromic acid, sulphuric acid, phosphoric acid, lactic acid, acetic acid, succinic acid, citric acid, palmitic acid or maleic acid. Compounds of general Formulae (I), (Ia), (Ib) and (Ic), containing a carboxy group, may be converted into the salts thereof, particularly into physiologically acceptable salts for pharmaceutical use, with organic or inorganic bases. Suitable bases for this purpose include, for example, sodium hydroxide, potassium hydroxide, ammonium hydroxide, arginine or ethanolamine.

In a further aspect the invention provides new compounds of general Formulae (I), (Ia), (Ib) and (Ic), such as, without being limited to, the compounds of structural Formulae 1, 2, 3, 4, 5, 6, 7, 8 and 9, including pharmaceutically acceptable salts thereof, which inhibit leukocyte transmigration in vitro and/or in vivo and possess suitable pharmacological and pharmacokinetic properties for use in therapy, that is for use as medicaments.

According to another aspect provided herein are uses of the compounds of general Formulae (I), (Ia), (Ib) and (Ic), such as, without being limited to, the compounds of structural Formulae 1, 2, 3, 4, 5, 6, 7, 8 and 9, for example as leukocyte transmigration inhibitors.

According to another aspect there is provided use of a compound having the structural Formula 10:

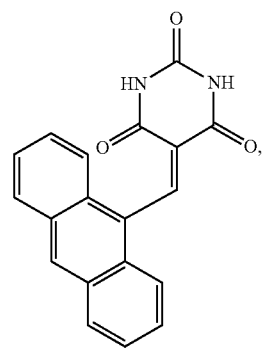

Formula 10 or pharmaceutically acceptable salt thereof, as a leukocyte transmigration inhibitor.

The compound of structural Formula 10 can be obtained by using known synthetic procedures (for example as described in Knoevenagel, E., Condensation von Malonsäure mit aromatischen Aldehyden durch Ammoniak und Amine. Berichte der deutschen chemischen Gesellschaft, 1898. 31(3): p. 2596-2619; and in Figueroa-Villar, J. D. and A. A. Vieira, Nuclear magnetic resonance and molecular modeling study of exocyclic carbon-carbon double bond polarization in benzylidene barbiturates. Journal of Molecular Structure, 2013. 1034: p. 310-317), for example as shown in Scheme 3 in Example 3 below, avoiding the formation of cis and trans isomers during the development of the double bond in the process of Knoevenagel condensation between a correspondent aldehyde and a stable carbanion in β-diketone position of the barbituric acid.

The compound of structural Formula 10, can be used in its final non-salt form or can be converted into the salts thereof, particularly physiologically acceptable salts for pharmaceutical use. Suitable salts of the compound of Formula 10, can be formed for example with organic or inorganic acids, such as, without being limited to hydrochloric acid, hydrobromic acid, sulphuric acid, phosphoric acid, lactic acid, acetic acid, succinic acid, citric acid, palmitic acid or maleic acid.

Another aspect of the invention relates to a pharmaceutical composition comprising one or more of compounds according to general Formulae (I), (Ia), (Ib) or (Ic), for example the compounds of structural Formulae 1, 2, 3, 4, 5, 6, 7, 8, 9 and 10, or stereoisomers, enantiomers, and tautomers thereof, pharmaceutically acceptable salts thereof and mixtures thereof; and a pharmaceutically acceptable carrier. The pharmaceutical compositions according to the invention optionally further comprise at least one additional therapeutic agent including but not limited to, anti-inflammatory agents, antiseptics, antibiotics, antivirals, bactericides, antifungals, antineoplastics, anticancer compounds, and/or or other bioactive or therapeutic agents that are suitable for human use.

Another aspect of the invention relates to the use of compound according to general Formulae (I), (Ia), (Ib) and (Ic), and of the compounds of structural Formulae 1, 2, 3, 4, 5, 6, 7, 8, 9 and 10, in the preparation of pharmaceutical composition for use as medicaments for treatment of diseases as described herein.

The compounds of general Formulae (I), (Ia), (Ib) and (Ic), especially the specific compounds of Formulae 1, 2, 3, 4, 5, 6, 7, 8 and 9, and the compound of Formula 10, are inhibitors of leukocyte transmigration. The effect of the compounds of the invention and of the specific compounds of Formulae 1, 2, 3, 4, 5, 6, 7, 8, 9 and 10 on leukocyte transmigration, i.e. their ability to inhibit leukocyte transmigration, is determined by flow assay. Flow assay screening may be carried out as described in the art (Butcher, E. C., Leukocyte-Endothelial Cell Recognition—3 (or More) Steps to Specificity and Diversity. Cell, 1991. 67(6): p. 1033-1036).

The compounds of general Formulae (I), (Ia), (Ib) and (Ic), and the compound of structural Formula 10, have $IC_{50}$ values for several activities in the range from 0.1 µM to 10 µM.

In view of the ability of the compounds of general Formulae (I), (Ia), (Ib) and (Ic), such as the specific compounds of Formulae 1, 2, 3, 4, 5, 6, 7, 8, 9, and the compound of Formula 10, and especially the specific compounds of Formulae 2, 9, and 10, to inhibit leukocyte transmigration, the compounds of general Formulae (I), (Ia), (Ib) and (Ic), especially the specific compounds of Formulae 2 and 9, and the compound of Formula 10, and the pharmaceutically acceptable salts thereof, may be suitable for treating and/or preventing all those conditions or diseases that can be influenced by inhibiting leukocyte transmigration or diseases and disorders associated with leukocyte transmigration. Therefore the compounds according to general Formulae (I), (Ia), (Ib) and (Ic), such as the specific compounds of Formulae 1, 2, 3, 4, 5, 6, 7, 8, 9, and the compound of Formula 10, and especially the specific compounds of Formulae 2, 9, and 10, and the pharmaceutically acceptable salts thereof, may be particularly suitable for the prevention or treatment of diseases or conditions, such as, without being limited to, inflammatory diseases and disorders, autoimmune diseases and disorders, and cancers.

The compounds of general Formulae (I), (Ia), (Ib) and (Ic), such as the specific compounds of Formulae 1, 2, 3, 4, 5, 6, 7, 8, 9, and the compound of Formula 10, and especially the specific compounds of Formulae 2, 9, and 10, and the pharmaceutically acceptable salts thereof, are also particularly suitable for the prevention or treatment of diseases or conditions such as lymphomas, in particular B cell lymphoma, such as, without being limited to small B-cell lymphoma (SLL), mantle cell lymphoma, hairy cell lymphoma marginal zone B cell lymphoma, diffuse large B cell lymphoma and Burkitt lymphoma. For example, it has been found that the treatment with a compound of Formula 2 significantly blocked the transmigration of the leukemic cancer cells to the spleen and liver in mice, as described in Example 7 below.

The compounds of general Formulae (I), (Ia), (Ib) and (Ic), such as the specific compounds of Formulae 1, 2, 3, 4, 5, 6, 7, 8, 9, and the compound of Formula 10, and especially the specific compounds of Formulae 2, 9, and 10, and the pharmaceutically acceptable salts thereof, can also be particularly suitable for the prevention or treatment of diseases or conditions such as for example: Myocarditis, Postmyocardial infarction syndrome, Postpericardiotomy syndrome, Subacute bacterial endocarditis (SBE), Anti-Glomerular Basement Membrane nephritis, Interstitial cystitis, Primary sclerosing cholangitis, Antisynthetase syndrome, Alopecia Areata, Autoimmune Angioedema, Autoimmune progesterone dermatitis, Autoimmune urticarial, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease (LAD), Morphea, Pemphigus vulgaris, Pityriasis lichenoides et varioliformis acuta, Mucha-Habermann disease, Addison's disease, Autoimmune polyendocrine syndrome (APS) type 1, Autoimmune polyendocrine syndrome (APS) type 2, Autoimmune polyendocrine syndrome (APS) type 3 Autoimmune pancreatitis, Diabetes mellitus type 1, Autoimmune thyroiditis, Ord's thyroiditis, Graves' disease, Autoimmune Oophoritis, Endometriosis, Autoimmune enteropathy, Coeliac disease, Crohn's disease, Antiphospholipid syndrome (APS, APLS), Aplastic anemia, Autoimmune hemolytic anemia, Autoimmune lymphoproliferative syndrome, Cold agglutinin disease, Essential mixed cryoglobulinemia, Evans syndrome, Paroxysmal nocturnal hemoglobinuria, Pernicious anemia, Pure red cell aplasia, Thrombocytopenia, Adiposis dolorosa, Adult-onset Still's disease, Ankylosing Spondylitis, Eosinophilic fasciitis, Felty syndrome, IgG4-related disease, Juvenile Arthritis, Lyme disease (Chronic), Mixed connective tissue disease (MCTD), Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus (SLE), Undifferentiated connective tissue disease, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis (ADEM), Acute motor axonal neuropathy, Anti-N-Methyl-D-Aspartate (Anti-NMDA) Receptor Encephalitis, Balo concentric sclerosis, Bickerstaffs encephalitis, Chronic inflammatory demyelinating polyneuropathy, Guillain-Barré syndrome, Multiple sclerosis, Oshtoran Syndrome, Pediatric Autoimmune Neuropsychiatric Disorder Associated with Streptococcus (PANDAS), Progressive inflammatory neuropathy, Restless leg syndrome Stiff person syndrome, Sydenham chorea, Transverse myelitis, Autoimmune retinopathy, Autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, Autoimmune inner ear disease (AIED), Mdniere's disease, Behget's disease, Eosinophilic granulomatosis with polyangiitis (EGPA), Giant cell arteritis, Granulomatosis with polyangiitis (GPA), IgA vasculitis (IgAV), Kawasaki's disease, leukocytoclastic vasculitis, Lupus vasculitis, Rheumatoid vasculitis, Microscopic polyangiitis (MPA), Polyarteritis nodosa (PAN), Polymyalgia rheumatic, Urticarial vasculitis, Vasculitis, Primary Immune Deficiency, Hashimoto's encephalopathy, Idiopathic inflammatory demyelinating diseases, Lambert-Eaton myasthenic syndrome, CREST syndrome, Drug-induced lupus, Enthesitis-related arthritis, Autoimmune neutropenia, Autoimmune thrombocytopenic purpura, Microscopic colitis, Ulcerative colitis, Autoimmune orchitis, Sjogren's syndrome, Psoriasis, Systemic scleroderma, Vitiligo, Lupus nephritis, Autoimmune hepatitis, Primary biliary cirrhosis (PBC).

The invention furthermore relates to medicaments comprising at least one compound of the general Formulae (I), (Ia), (Ib) and (Ic) and/or pharmaceutically acceptable derivatives, solvates and stereoisomers thereof, including mixtures thereof in all ratios, and optionally excipients and/or adjuvants. The compounds of general Formulae (I), (Ia), (Ib) and (Ic), such as, without being limited to, the compounds of structural Formulae 1, 2, 3, 4, 5, 6, 7, 8 and 9, and the compound of Formula 10, and the pharmaceutically acceptable salts thereof, may be formulated in a pharmaceutical composition, optionally comprising other active substances, and one or more of inert conventional excipients, as known to the skilled artisans. The pharmaceutical compositions may be prepared according to the general guidance provided in the art, e.g. by Remington, The Science and Practice of Pharmacy (formerly known as Remington's Pharmaceutical Sciences), ISBN 978-0-85711-062-6. Such pharmaceutical formulations can be adapted for administration via any desired suitable method known in the art, for example by oral (including buccal or sublingual), rectal, nasal, topical (including buccal, sublingual or transdermal), vaginal or parenteral (including subcutaneous, intramuscular, intravenous or intradermal) methods. Such pharmaceutical compositions, e.g. in the form solid dosage forms, topical dosage form, and/or parenteral dosage forms, e.g. tablets, capsules, creams, ointments, patches, injections, and others as known in the art constitute another aspect of the invention.

The dose of compounds of general Formulae (I), (Ia), (Ib) and (Ic), such as, without being limited to, the compounds of structural Formulae 1, 2, 3, 4, 5, 6, 7, 8 and 9, and the compound of Formula 10, and the pharmaceutically acceptable salts thereof, required to achieve treatment or prevention of a disease or a disorder or a condition usually depends on the pharmacokinetic and pharmacodynamic properties of the compound which is to be administered, the patient, the nature of the disease, disorder or condition and the method and frequency of administration.

Suitable dosage ranges for compounds of general Formulae (I), (Ia), (Ib) and (Ic), such as, without being limited to, the compounds of structural Formulae 1, 2, 3, 4, 5, 6, 7, 8 and 9, and the compound of Formula 10, and the pharmaceutically acceptable salts thereof, may be from 1.0 to 100 mg/kg body weight.

Accordingly, in another aspect there is provided a method for preventing or treating a disease or condition selected from the list consisting of inflammatory disease and disorders, autoimmune diseases and disorders, such as for example: Myocarditis, Postmyocardial infarction syndrome, Postpericardiotomy syndrome, Subacute bacterial endocarditis (SBE), Anti-Glomerular Basement Membrane nephritis, Interstitial cystitis, Primary sclerosing cholangitis, Antisynthetase syndrome, Alopecia Areata, Autoimmune Angioedema, Autoimmune progesterone dermatitis, Autoimmune urticarial, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease (LAD), Morphea, Pemphigus vulgaris, *Pityriasis lichenoides* et varioliformis acuta, Mucha-Habermann disease, Addison's disease, Autoimmune polyendocrine syndrome (APS) type 1, Autoimmune polyendocrine syndrome (APS) type 2, Autoimmune polyendocrine syndrome (APS) type 3 Autoimmune pancreatitis, Diabetes mellitus type 1, Autoimmune thyroiditis, Ord's thyroiditis, Graves' disease, Autoimmune Oophoritis, Endometriosis, Autoimmune enteropathy, Coeliac disease, Crohn's disease, Antiphospholipid syndrome (APS, APLS), Aplastic anemia, Autoimmune hemolytic anemia, Autoimmune lymphoproliferative syndrome, Cold agglutinin disease, Essential mixed cryoglobulinemia, Evans syndrome, Paroxysmal nocturnal hemoglobinuria, Pernicious anemia, Pure red cell aplasia, Thrombocytopenia, Adiposis dolorosa, Adult-onset Still's disease, Ankylosing Spondylitis, Eosinophilic fasciitis, Felty syndrome, IgG4-related disease, Juvenile Arthritis, Lyme disease (Chronic), Mixed connective tissue disease (MCTD), Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus (SLE), Undifferentiated connective tissue disease, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis (ADEM), Acute motor axonal neuropathy, Anti-N-Methyl-D-Aspartate (Anti-NMDA) Receptor Encephalitis, Balo concentric sclerosis, Bickerstaffs encephalitis, Chronic inflammatory demyelinating polyneuropathy, Guillain-Barré syndrome, Multiple sclerosis, Oshtoran Syndrome, Pediatric Autoimmune Neuropsychiatric Disorder Associated with Streptococcus (PANDAS), Progressive inflammatory neuropathy, Restless leg syndrome Stiff person syndrome, Sydenham chorea, Transverse myelitis, Autoimmune retinopathy, Autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, Autoimmune inner ear disease (AIED), Mdniere's disease, Behget's disease, Eosinophilic granulomatosis with polyangiitis (EGPA), Giant cell arteritis, Granulomatosis with polyangiitis (GPA), IgA vasculitis (IgAV), Kawasaki's disease, leukocytoclastic vasculitis, Lupus vasculitis, Rheumatoid vasculitis, Microscopic polyangiitis (MPA), Polyarteritis nodosa (PAN), Polymyalgia rheumatic, Urticarial vasculitis, Vasculitis, Primary Immune Deficiency, Hashimoto's encephalopathy, Idiopathic inflammatory demyelinating diseases, Lambert-Eaton myasthenic syndrome, CREST syndrome, Drug-induced lupus, Enthesitis-related arthritis, Autoimmune neutropenia, Autoimmune thrombocytopenic purpura, Microscopic colitis, Ulcerative colitis, Autoimmune orchitis, Sjogren's syndrome, Psoriasis, Systemic scleroderma, Vitiligo, Lupus nephritis, Autoimmune hepatitis, Primary biliary cirrhosis (PBC); B cell lymphomas and other types of cancers, in a subject in need thereof, comprising administering to the subject a therapeutically effective amount of a compound of general Formulae (I), (Ia), (Ib) or (Ic), such as, without being limited to, the compounds of structural Formulae 1, 2, 3, 4, 5, 6, 7, 8 and 9, or of a compound of Formula 10, as defined herein.

EXAMPLES

Materials and Methods

All chemical reagents, solvents, and acids were purchased from Sigma-Aldrich, Acros Organic, Alfa Aesar, Bio-Lab Ltd., Merck, or IU-CHEM Ltd., and were all used as received. Anhydrous THF was obtained by distillation from a boiled blue colored mix containing sodium (1% w/v) and benzophenone (0.2% w/v). Anhydrous DMF was obtained by distillation under vacuum and stored over 4 A° molecular sieves. Column chromatography was performed on silica gel 60 (230-400 mesh; Merck). Analytical and preparative HPLC (Young Lin Instruments, Anyang, Korea) were performed on LUNA Cis preparative (10 μm, 100×30 mm) or analytical (5 μm, 250×4.6 mm) columns, both from Phenomenex, Inc. (Torrance, CA, USA). HPLC purification was carried out with an increasing linear gradient of $CH_3CN$ in $H_2O$. The purity of the synthesized compounds was confirmed by HPLC analysis. Analytical TLC was carried out on pre-coated silica gel 60 $F_{254}$ (Merck) sheets using UV absorption and iodine physical adsorption for visualization. Mass spectra were recorded on a Finnigan Model 400 instrument using a QToF microspectrometer (Micromass, Milford, MA, USA), using electrospray ionization (ESI) in the positive ion mode. Data were processed using mass L-ynX ver. 4.1 calculation and de-convolution software (Waters Corp., Milford, MA, USA). High-resolution mass spectra (HRMS) were obtained using an LTQ Orbitrap XL (Thermo Scientific, Waltham, MA, USA). Melting points were measured with a Fisher-Johns melting point apparatus (Waltham, MA, USA). The $^1$H NMR, $^{13}$C NMR, F$^{19}$ NMR and 2D spectra were recorded at room temperature on a Bruker Avance NMR spectrometer (Vernon Hills, IL) operating at 300, 400, 600 and 700 MHz and were in accord with the assigned structures. Chemical shift values were reported relative to TMS that was used as an internal standard. Chemical shifts were expressed in δ (ppm) and coupling constants (J) in hertz. The splitting pattern abbreviations are as follows: s, singlet; d, doublet; t, triplet; q, quartet; quint, quintet; m, unresolved multiplet due to the field strength of the instrument; dd, doublet of doublet.

For endothelial cell preparation and culture, endothelial cell growth supplement (Upstate Biotechnology, Lake Placid, NY) was used. For monocyte purification a monocyte isolation kit (Miltenyi Biotec, Bergisch Gladbach, Germany) was utilised. HUVECs were cultured at $1\times10^5$ cells/slide on Ibidi 6-chamber slides (80606; Ibidi). Calibrated pump used (74 900; Cole Partner, Vernon Hills, IL). Observations made using phase-contrast microscopy (Model: Axiovert 100; Objective: 20×/0.3 NA air; Carl Zeiss) were recorded using a high-resolution camera (D70; Nikon, Zurich, Switzerland).

Mice

NOD.CB17-Prkdcscid/J (NOD/SCID), DBA/1, NOD mice and Inbred mouse strain: C57BL/6J (B6 #000664), female mice were obtained from The Jackson Laboratory (Bar Harbor, ME) at 6 weeks of age. All animal experiments were approved by the Institutional Animal Care and Research Advisory Committee at Geneva University and Veterinary Committee of Israeli Ministry of Health.

Preparation of Intermediates A and F

General procedure for the synthesis of methylated benzoates, such as intermediates methyl 4-(bromomethyl) benzoate (A) and methyl 3-(chloromethyl)benzoate (F) is described in Vassiliou, S., et al., (A synthetic method for diversification of the P1' substituent in phosphinic dipeptides as a tool for exploration of the specificity of the S1' binding pockets of leucine aminopeptidases. Bioorganic & Medicinal Chemistry, 2007. 15(9): p. 3187-3200).

To a solution of 4-bromomethylbenzoic acid or 3-chloromethylbenzoic acid (2.30 mmol) in MeOH (5.6 mL), concentrated sulfuric acid (0.14 mL) was added. The resulting mixture was refluxed for 5 hours. Then, the mixture was cooled to room temperature and evaporated in vacuo. H$_2$O (20 mL) was added to the reaction mixture in an ice-water bath, and the resulting solid was filtered and washed with cold water. The solid material was partitioned between Et$_2$O/AcOEt 1:1 and Na$_2$CO$_3$. The organic layer was dried over Na$_2$SO$_4$, and evaporated in vacuo to afford the products.

Methyl 4-(bromomethyl)benzoate (A): was obtained starting from 4-bromomethylbenzoic acid, (white powder, yield 48%): $^1$H NMR (400 MHz, CDCl$_3$): δ 7.96 (d, J=8.41 Hz, 2H), 7.40 (d, J=8.41 Hz, 2H), 4.45 (s, 2H), 3.87 (s, 3H) ppm. $^{13}$C NMR (100.6 MHz, CDCl$_3$): δ 166.28, 142.59, 129.95, 128.98, 52.10, 32.27 ppm. MS (ESI, SQ), m/z (%): (229 $^{79}$Br, 231 $^{81}$Br) [M+H]$^+$.

Methyl 3-(chloromethyl)benzoate (F): was obtained starting from 3-chloromethylbenzoic acid (colorless syrup, yield 75%): $^1$H NMR (400 MHz, CDCl$_3$): δ 8.06 (s, 1H), 7.99 (d, J=7.76 Hz, 1H), 7.58 (d, J=7.76 Hz, 1H) 7.429 (t, J=7.76 Hz, 1H), 4.61 (s, 2H), 3.92 (s, 3H) ppm. $^{13}$C NMR (100.6 MHz, CDCl$_3$): δ 166.54, 137.91, 132.99, 130.73, 129.67, 129.55, 128.28, 52.23, 45.52 ppm. GC-MS (EI), 70 ev, m/z (%): 184 [M]$^+$.

Preparation of Intermediates B, C, D, E, G, H and I

General procedure for the synthesis of intermediate compounds B, C, D, E, G, H and I is described in Zidar, N., et al., (New 5-benzylidenethiazolidin-4-one inhibitors of bacterial MurD ligase: Design, synthesis, crystal structures, and biological evaluation. European Journal of Medicinal Chemistry, 2011. 46(11): p. 5512-5523). A suspension of intermediate compound A or F (6.55 mmol) and a corresponding benzaldehyde (6.55 mmol), potassium carbonate (13.10 mmol), and potassium iodide (7.86 mmol) was heated at 70° C. for 5 hours. The solvent was evaporated, the residue dissolved in ethyl acetate (50 mL), washed with saturated aqueous NaHCO$_3$ solution (2×20 mL), water (2×20 mL), and brine (2×10 mL), dried over Na$_2$SO$_4$ and concentrated under reduced pressure. The crude product was purified by flash column chromatography using ethyl acetate/petroleum ether as an eluent.

Methyl 4-((2-formylphenoxy)methyl)benzoate, (B): (white powder, yield 60%)$^1$H NMR (300 MHz, CDCl$_3$): δ 10.57 (s, 1H), 8.07 (d, J=8.43 Hz, 2H), 7.86 (d, J=7.50 Hz, 1H), 7.53 (d, J=8.43 Hz, 2H), 7.76 (t, J=7.50 Hz, 1H), 7.06 (t, J=7.50 Hz, 1H), 7.01 (d, J=8.44 Hz, 1H), 5.25 (s, 2H), 3.92 (s, 3H) ppm. $^{13}$C NMR (75.49 MHz, CDCl$_3$): δ 189.48, 166.68, 160.64, 141.18, 135.94, 130.03, 128.73, 126.85, 125.19, 121.31, 112.90, 69.76, 52.20 ppm. MS (ESI, SQ), m/z (%): 293.1 [M+Na]$^+$.

Methyl 4-((3-formylphenoxy)methyl)benzoate, (C): (yellow powder, yield 54%)$^1$H NMR (300 MHz, CDCl$_3$): δ 9.96 (s, 1H), 8.06 (d, J=8.27 Hz, 2H), 7.54-7.44 (m, 5H), 7.29-7.22 (m, 1H), 5.17 (s, 2H), 3.91 (s, 3H) ppm. $^{13}$C NMR (75.49 MHz, CDCl$_3$) δ 191.95, 166.74, 159.01, 141.48, 137.87, 130.23, 129.96, 129.89, 127.02, 124.00, 122.11, 113.15, 69.49, 52.16 ppm. MS (ESI, SQ), m/z (%): 271.1 [M+H]$^+$, 293.2 [M+Na]$^+$.

Methyl 4-((2-(tert-butyl)-6-formylphenoxy) methyl)benzoate, (D): (off white powder, yield 43%, m.p 84° C.)$^1$H NMR (300 MHz, CDCl$_3$): δ 10.30 (s, 1H), 8.11 (d, J=8.04 Hz, 2H), 7.75 (dd, J=7.80 Hz, J=1.65 Hz, 1H), 7.64 (dd, J=7.81 Hz, J=1.62 Hz, 1H), 7.58 (d, J=8.04 Hz, 2H), 7.21 (t, J=7.81 Hz, 1H), 5.12 (s, 2H), 3.94 (s, 3H), 1.44 (s, 9H) ppm. $^{13}$C NMR (75.49 MHz, CDCl$_3$): δ 190.16, 166.78, 161.26, 143.93, 141.53, 133.72, 129.99, 129.91, 128.36, 126.53, 124.37, 79.35, 52.18, 35.26, 30.86 ppm. MS (ESI) found m/z 349.14102 (calcd for C$_{20}$H$_{22}$O$_4$: 349.14103 [M+Na]$^+$). Anal. Calcd for C$_{20}$H$_{22}$O$_4$: C, 73.60; H, 6.79. Found: C, 74.32; H, 7.03.

Methyl 4-((4-formyl-2,6-dimethylphenoxy)methyl)benzoate, (E): (yellow powder, yield 94%, m.p 82° C.)$^1$H NMR (400 MHz, CDCl$_3$): δ 9.87 (s, 1H), 8.07 (d, J=8.4 Hz, 2H), 7.57 (s, 2H), 7.54 (d, J=8.4 Hz, 2H), 4.92 (s, 2H), 3.92 (s, 3H), 2.33 (s, 6H) ppm. $^{13}$C-NMR (75.49 MHz, CDCl$_3$): δ 191.52, 166.69, 160.86, 141.99, 132.52, 132.07, 130.75, 129.66, 127.24, 73.25, 52.13, 16.46 ppm. MS (ESI) found m/z 299.12793 (calcd for C$_{18}$H$_{18}$O$_4$: 299.12779 [M+H]$^+$). Anal. Calcd for C$_{18}$H$_{18}$O$_4$: C, 72.47; H, 6.08. Found: C, 71.92; H, 5.87.

Methyl 3-((2-formylphenoxy)methyl)benzoate, (G): (white powder, yield 44%)$^1$H NMR (300 MHz, CDCl$_3$): δ 10.52 (s, 1H), 8.10 (s, 1H), 7.98 (d, J=7.63 Hz, 1H), 7.81 (d, J=7.63 Hz, 1H), 7.63 (d, J=7.63 Hz, 1H), 7.55-7.38 (m, 2H), 7.08-6.95 (m, 2H), 5.16 (s, 2H), 3.89 (s, 3H) ppm. $^{13}$C NMR (75.49 MHz, CDCl$_3$): δ 189.00, 166.27, 160.43, 136.37, 135.68, 131.43, 130.32, 129.08, 128.57, 128.15, 128.06, 124.81, 120.86, 112.71, 69.48, 51.87 ppm. MS (ESI, SQ), m/z (%): 271.2 [M+H]$^+$, 293.1 [M+Na]$^+$.

Methyl 3-((4-formylphenoxy)methyl)benzoate, (H): (white powder, yield 51%)$^1$H NMR (300 MHz, CDCl$_3$): δ 9.83 (s, 1H), 8.09 (s, 1H), 7.98 (d, J=7.56 Hz, 1H), 7.79 (d, J=8.32 Hz, 2H), 7.60 (d, J=7.56 Hz, 1H), 7.43 (t, J=7.56 Hz, 1H), 7.04 (d, J=8.32 Hz, 2H), 5.10 (s, 2H), 3.87 (s, 3H) ppm. $^{13}$C NMR (75.49 MHz, CDCl$_3$) δ 190.58, 166.50, 163.34, 136.53, 131.89, 131.81, 130.54, 130.23, 129.32, 128.76, 128.45, 115.05, 69.46, 52.10 ppm. MS (ESI, SQ), m/z (%): 271.2 [M+H]$^+$, 293 [M+Na]$^+$.

Methyl 3-(3-formylphenoxy)methyl)benzoate, (I): (white powder, yield 41%)$^1$H NMR (300 MHz, CDCl$_3$): δ 9.95 (s, 1H), 8.12 (s, 1H), 8.01 (d, J=7.12 Hz, 1H), 7.63 (d, J=7.12 Hz, 1H), 7.53-7.40 (m, 4H), 7.31-7.17 (m, 1H), 5.13 (s, 2H), 3.91 (s, 3H) ppm. $^{13}$C NMR (75.49 MHz, CDCl$_3$) δ 192.02, 166.76, 159.06, 137.83, 136.81, 131.86, 130.57, 130.19, 129.33, 128.77, 128.54, 123.86, 122.06, 113.25, 69.55, 52.21 ppm. MS (ESI, SQ), m/z (%): 271.2 [M+H]$^+$, 293 [M+Na]$^+$.

Example 1

Preparation of Compounds of Formulae 1-5, 7 and 9

General procedure for the coupling of barbituric acid and corresponding aldehydes is described in Ma, L., et al. (Synthesis and biological evaluation of 5-benzylidenepyrimidine-2,4,6(1H,3H,5H)-trione derivatives for the treatment of obesity-related nonalcoholic fatty liver disease. J Med Chem, 2012. 55(22): p. 9958-72).

Briefly, a corresponding aldehyde (prepared as described hereinabove) (3.5 mmol), ethanol (10 mL), distilled water (10 mL), and barbituric acid (3 mmol) were refluxed overnight. The formed solids were collected by sucking filtration and washed with boiling water (3×15 mL), ethanol (3×15 mL) and ether (3×15 mL). The solids obtained were dried in vacuum.

Methyl 4-((3-((2,4,6-trioxotetrahydropyrimidin-5(2H)-ylidene) methyl) phenoxy) methyl) benzoate, (compound of Formula 1): (yellow powder, yield 57%, m.p 256° C.) $^1$H NMR (300 MHz, DMSO-6D): δ 11.41 (s, 1H), 11.26 (s, 1H), 8.25 (s, 1H), 7.99 (d, J=7.84 Hz, 2H), 7.91 (s, 1H), 7.71-7.57 (m, 3H), 7.405 (t, J=8.10 Hz, 1H), 7.22 (d, J=8.10 Hz, 1H), 5.25 (s, 2H), 3.86 (s, 3H) ppm. $^{13}$C NMR (75.49 MHz, DMSO-6D): δ 165.93, 163.27, 161.49, 157.43, 154.19, 150.07, 142.26, 133.84, 129.27, 129.12, 128.95, 127.47, 126.29, 119.32, 118.93, 118.6468.62, 52.06 ppm. MS (ESI) found m/z 403.09000 (calcd for C$_{20}$H$_{16}$N$_2$O$_6$: 403.09006 [M+Na]$^+$). Anal. Calcd for C$_{20}$H$_{16}$N$_2$O$_6$: C, 63.16; H, 4.24; N, 7.37. Found: C, 63.23; H, 4.35; N, 7.56.

Methyl 4-((2-(tert-butyl)-6-((2,4,6-trioxotetrahydropyrimidin-5(2H)-ylidene) methyl) phenoxy) methyl) benzoate, (compound of Formula 2): (yellow powder, yield 14%, m.p 184° C.)$^1$H NMR (300 MHz, DMSO-6D): δ 11.33 (s, 1H), 11.19 (s, 1H), 8.34 (s, 1H), 7.99 (d, J=8.08 Hz, 2H), 7.70 (d, J=7.85 Hz, 1H), 7.61 (d, J=8.08 Hz, 2H), 7.48 (d, J=7.85 Hz, 1H), 7.12 (t, J=7.85 Hz, 1H), 4.94 (s, 2H), 3.94 (s, 3H), 1.38 (s, 9H) ppm. $^{13}$C NMR (100.6 MHz, DMSO-6D) δ 165.88, 162.95, 161.14, 157.91, 150.35, 150.20, 142.04, 141.62, 130.30, 130.27, 129.21, 129.05, 127.75, 127.37, 122.78, 119.60, 76.96, 52.07, 34.64, 30.50 ppm. MS (ESI) found m/z 437.17087 (calcd for C$_{24}$H$_{24}$N$_2$O$_6$: 437.17071 [M+H]$^+$). Anal. Calcd for C$_{24}$H$_{24}$N$_2$O$_6$: C, 66.05; H, 5.54; N, 6.42. Found: C, 66.12; H, 5.53; N, 6.81.

Methyl 4-((2-((2,4,6-trioxotetrahydropyrimidin-5(6H)-ylidene) methyl) phenoxy) methyl) benzoate, (compound of Formula 3): (yellow powder, yield 64%)$^1$H NMR (300 MHz, DMSO-6D): δ 11.35 (s, 1H), 11.17 (s, 1H), 8.58 (s, 1H), 8.06-7.93 (m, 3H), 7.60 (d, J=8.28 Hz, 2H), 7.50 (t, J=7.29 Hz, 1H), 7.16 (d, J=8.28 Hz, 1H), 7.01 (t, J=7.62 Hz, 1H), 5.34 (s, 2H), 3.86 (s, 3H) ppm. $^{13}$C NMR (150.9 MHz, DMSO-6D): δ 165.87, 163.22, 161.32, 157.64, 150.14, 149.65, 142.05, 133.71, 132.40, 129.28, 129.06, 127.32, 122.07, 119.93, 118.94, 112.39, 69.25, 52.06 ppm. MS (ESI, SQ), m/z (%): 381.3 [M+H]$^+$.

Methyl 4-((2,6-dimethyl-4-((2,4,6-trioxotetrahydropyrimidin-5(2H)-ylidene) methyl) phenoxy) methyl) benzoate, (compound of Formula 4): (yellow powder, yield 73%, m.p 281° C.)$^1$H NMR (400 MHz, DMSO-6D): δ 11.35 (s, 1H), 11.20 (s, 1H), 8.19 (s, 1H), 8.02 (d, J=8.26 Hz, 2H), 7.99 (s, 2H), 7.66 (d, J=8.26 Hz, 2H), 5.00 (s, 2H), 3.87 (s, 3H), 2.97 (s, 6H) ppm. $^{13}$C NMR (100.6 MHz, DMSO-6D): δ 165.94, 163.54, 161.69, 159.16, 154.52, 150.11, 142.49, 135.17, 130.44, 129.24, 129.09, 128.26, 127.80, 117.32, 72.68, 52.07, 16.14 ppm. MS (ESI) found m/z 409.13950 (calcd for C$_{22}$H$_{20}$N$_2$O$_6$: 409.13941 [M+H]$^+$). Anal. Calcd for C$_{22}$H$_{20}$N$_2$O$_6$: C, 64.70; H, 4.94; N, 6.86. Found: C, 65.03; H, 4.76; N, 6.77.

Methyl 3-((2-((2,4,6-trioxotetrahydropyrimidin-5(6H)-ylidene) methyl) phenoxy) methyl) benzoate, (compound of Formula 5): (orange powder, yield 56%, m.p 200° C.) $^1$H NMR (300 MHz, DMSO-6D): δ 11.46 (s, 1H), 11.27 (s, 1H), 8.68 (s, 1H), 8.17 (s, 1H), 8.10 (d, J=8.21 Hz, 1H), 8.04 (d, J=7.62 Hz, 1H), 7.85 (d, J=7.33 Hz, 1H), 7.68 (t, J=7.59 Hz, 1H), 7.61 (t, J=7.87 Hz, 1H), 7.31 (d, J=8.50 Hz, 1H), 7.116 (t, J=7.62 Hz, 1H) ppm. $^{13}$C NMR (75.49 MHz, DMSO-6D): δ 165.90, 163.18, 161.30, 157.66, 150.15, 149.72, 137.38, 133.70, 132.38, 132.04, 129.81, 128.96, 128.59, 127.88, 122.08, 119.87, 118.92, 112.41, 69.20, 52.12 ppm. MS (ESI) found m/z 381.10834 (calcd for C$_{20}$H$_{16}$N$_2$O$_6$: 381.10811 [M+H]$^+$). Anal. Calcd for C$_{20}$H$_{16}$N$_2$O$_6$: C, 63.16; H, 4.24; N, 7.37. Found: C, 63.16; H, 4.32; N, 7.12.

Methyl 3-((4-((2,4,6-trioxotetrahydropyrimidin-5(2H)-ylidene) methyl) phenoxy) methyl) benzoate, (compound of Formula 7): The title compound was obtained starting from 34 and 5 (yellow powder, yield 71%, m.p 227° C.) 1H NMR (300 MHz, DMSO-6D): δ 11.33 (s, 1H), 11.20 (s, 1H), 8.37 (d, J=8.34 Hz, 2H), 8.26 (s, 1H), 7.95 (d, J=7.47 Hz, 1H), 7.77 (d, J=7.60 Hz, 1H), 7.58 (t, J=7.60 Hz, 1H), 7.16 (d, J=8.34 Hz, 2H), 5.34 (s, 2H), 3.87 (s, 3H) ppm. 13C NMR (75.45 MHz, DMSO-6D): δ 165.93, 163.798, 162.18, 162.06, 154.74, 150.12, 137.31, 137.14, 132.46, 129.83, 128.99, 128.72, 128.22, 125.40, 115.71, 114.60, 68.88, 52.14 ppm. MS (ESI) found m/z 381.10818 (calcd for C20H16N2O6: 381.10811 [M+H]+). Anal. Calcd for C20H16N2O6: C, 63.16; H, 4.24; N, 7.37. Found: C, 62.39; H, 4.63; N, 7.24.

Methyl 3-((3-((2,4,6-trioxotetrahydropyrimidin-5(2H)-ylidene) methyl) phenoxy) methyl) benzoate, (compound of Formula 9): (yellow powder, yield 17%, m.p 158° C.)$^1$H NMR (300 MHz, DMSO-6D): δ 11.40 (s, 1H), 11.25 (s, 1H), 8.25 (s, 1H), 8.06 (s, 1H), 7.93-7.83 (m, 2H), 7.75 (d, J=7.54 Hz, 1H), 7.66 (d, J=7.95 Hz, 1H), 7.57 (t, J=7.54 Hz, 1H), 7.41 (t, J=7.95 Hz, 1H), 7.22 (d, J=8.37 Hz, 1H), 5.24 (s, 2H), 3.87 (s, 3H) ppm. $^{13}$C NMR (150.9 MHz, DMSO-6D):

δ 165.96, 163.26, 161.48, 157.49, 154.24, 150.05, 137.57, 133.85, 132.32, 129.79, 129.11, 128.94, 128.55, 128.06, 126.19, 119.32, 118.89, 118.73, 68.67, 52.11 ppm. MS (ESI) found m/z 381.10840 (calcd for $C_{20}H_{16}N_2O_6$: 381.10811 [M+H]$^+$). Anal. Calcd for $C_{20}H_{16}N_2O_6$: C, 63.16; H, 4.24; N, 7.37. Found: C, 63.19; H, 4.29; N, 7.14.

Example 2

Preparation of Compounds of Formulae 6 and 8

General procedure for the synthesis of benzoic acid derivatives is described in Zidar, N., et al., New 5-benzylidenethiazolidin-4-one inhibitors of bacterial MurD ligase: Design, synthesis, crystal structures, and biological evaluation. European Journal of Medicinal Chemistry, 2011. 46(11): p. 5512-5523.

Briefly, to a stirred solution of compounds of Formulae 5 or 7 (5.55 mmol) in 1,4-dioxane/methanol/water (1:1:1) (30 mL), 2 M NaOH (5.55 mL, 11.10 mmol) was added dropwise. After 5 hours the mixture was acidified to pH 3 with 1 M HCl, the organic phase was evaporated, the residue dissolved in ethyl acetate (50 mL), washed with 10% citric acid (2×20 mL) and brine (2×15 mL), dried over $Na_2SO_4$, and concentrated under reduced pressure.

3-((2-((2,4,6-trioxotetrahydropyrimidin-5(6H) ylidene) methyl) phenoxy) methyl) benzoic acid, (compound of Formula 6): (yellow powder, yield 49%, m.p 242° C.) $^1$H NMR (600 MHz, DMSO-6D): δ 11.31 (s, 1H), 11.13 (s, 1H), 8.55 (s, 1H), 8.2 (s, 1H), 7.99 (d, J=8.05 Hz, 1H), 7.91 (d, J=7.47 Hz, 1H), 7.71 (d, J=8.05 Hz, 1H), 7.54 (t, J=8.05 Hz, 1H), 7.50 (t, J=7.47 Hz, 1H), 7.19 (d, J=8.38 Hz, 1H), 7.00 (t, J=7.47 Hz, 1H) ppm. $^{13}$C NMR (150.9 MHz, DMSO-6D): δ 167.00, 163.25, 161.36, 157.81, 150.18, 149.75, 137.18, 133.80, 132.49, 131.76, 131.03, 128.84, 128.26, 122.06, 119.87, 118.90, 112.46, 69.44 ppm. MS (ESI) found m/z 367.09259. calcd for $C_{19}H_{14}N_2O_6$: 367.09246 [M+H]$^+$. Anal. Calcd for $C_{19}H_{14}N_2O_6$: C, 62.30; H, 3.85; N, 7.65. Found: C, 62.32; H, 3.90; N, 7.58.

3-((4-((2,4,6-trioxotetrahydropyrimidin-5(2H) ylidene) methyl)phenoxy) methyl) benzoic acid, (compound of Formula 8): (yellow powder, yield 61%, m.p 289° C.)$^1$H NMR (600 MHz, DMSO-6D): δ 11.30 (s, 1H), 11.17 (s, 1H), 8.37 (d, J=9 Hz, 2H), 8.26 (s, 1H), 7.93 (d, J=7.79 Hz, 1H), 7.73 (d, J=7.79 Hz, 1H), 7.55 (t, J=7.79 Hz, 1H), 7.16 (d, J=9 Hz, 2H), 5.33 (s, 2H), 2.09 (s, 3H) ppm. $^{13}$C NMR (150.9 MHz, DMSO-6D): δ 166.98, 163.77, 162.22, 162.03, 154.74, 150.08, 137.28, 136.90, 132.01, 130.99, 128.85, 128.79, 128.38, 125.38, 115.71, 114.61, 68.99 ppm. MS (ESI) found m/z 367.09265 (calcd for $C_{19}H_{14}N_2O_6$: 367.09246 [M+H]$^+$). Anal. Calcd for $C_{19}H_{14}N_2O_6$: C, 62.30; H, 3.85; N, 7.65.

Found: C, 62.12; H, 3.91; N, 7.43.

Example 3

Preparation of compounds of Formula 10 (5-(anthracen-9-ylmethylene)pyrimidine-2,4,6(1H,3H,5H)-trione)

Compound of Formula 10 was synthetized as shown in Scheme 3 following the procedure described in detail in Example 1 hereinabove.

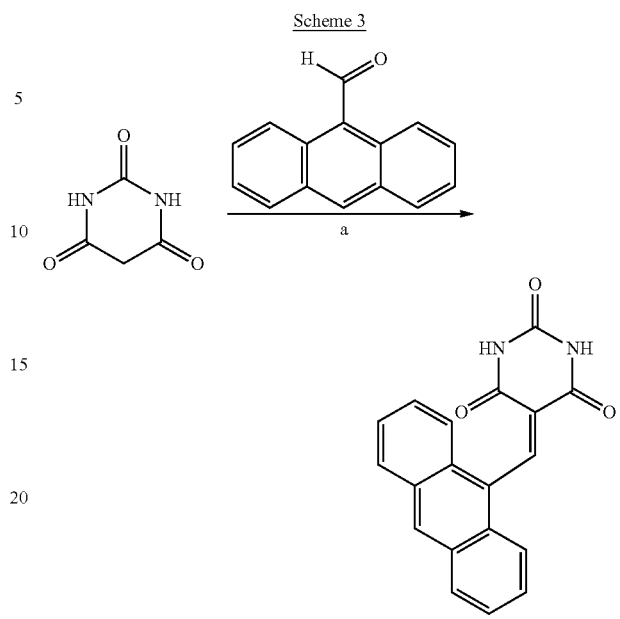

Scheme 3

In Scheme 3: a) EtOH:$H_2O$ 1:1, barbituric acid, reflux overnight.

5-(anthracen-9-ylmethylene)pyrimidine-2,4,6(1H,3H, 5H)-trione, (compound of Formula 10): (red powder, yield 54%, m.p >300° C.)$^1$H NMR (400 MHz, DMSO-6D): δ 11.57 (s, 1H), 11.17 (s, 1H), 9.01 (s, 1H), 8.63 (s, 1H), 8.12 (s, 2H), 7.97 (s, 2H), 7.52 (s, 4H) ppm. $^{13}$C NMR (75.46 MHz, DMSO-6D) δ 162.28, 160.41, 151.20, 150.42, 130.50, 129.38, 128.57, 127.69, 127.55, 126.12, 125.42 ppm. MS (ESI) found m/z 317.009259 (calcd for $C_{19}H_{12}N_2O_3$: 317.09207 [M+H]$^+$). Anal. Calcd for $C_{19}H_{12}N_2O_3$: C, 72.15; H, 3.82; N, 8.86. Found: C, 72.12; H, 3.79; N, 8.72.

Example 4

Biological Evaluation In Vitro—Leukocyte Flow

A flow assay that allows detailed analysis of individual leukocyte interactions with endothelial cells (ECs), described in Bradfield et al. (Bradfield et al., 2016, PloS One, July 21; 11(7); Bradfield et al., 2007, Blood. October 1; 110(7):2545-55) was used for evaluation of the biological effects of the compounds according to the invention. This method allows the determination of the possible effects of the compounds on three major phases in leukocyte migration: the capture of free non-bound leukocytes by endothelium, migration of leukocytes on the endothelium surface, and transendothelial migration (transmigration) of human leukocytes through the HUVECs layer. Post transmigrational events can also be monitored by tracking individual leukocytes. FIG. 1 shows the generic structure of a flow chamber. Human umbilical vein endothelial cells (HUVECs) were cultivated in the plastic channel of the flow chamber, and human leukocyte were flowed over them using a calibrated pump, allowing monocyte capture, adhesion and migration to be monitored.

Cell Preparation

Endothelial Cell Preparation and Culture

Human umbilical vein endothelial cells (HUVEC) were isolated by collagenase treatment of umbilical veins as previously described (Wall, R. T., et al., Factors influencing endothelial cell proliferation in vitro. J Cell Physiol, 1978. 96(2): p. 203-13) and maintained in M199 containing 20% fetal calf serum (FCS), 15 μg/mL endothelial cell growth supplement (Upstate Biotechnology, Lake Placid, NY), 100 μg/mL heparin, 50 μM hydrocortisone, and 10 μg/mL vitamin C. Cells were cultured up to a maximum of passage 5.

Monocyte Isolation

Peripheral blood mononuclear cells (PBMCs) were first isolated from blood of healthy donors followed by monocyte purification using a monocyte isolation kit (Miltenyi Biotec, Bergisch Gladbach, Germany). Purity and activity of monocytes were controlled by flow cytometry by labelling with anti-CD14 and anti-CD62L. Only populations of 90% or more double positive cells were used.

Experimental Set-Up

Shear Flow Assays

Flow assays were conducted as described in a previous study (Bradfield, P. F., et al., JAM-C regulates unidirectional monocyte transendothelial migration in inflammation. Blood, 2007. 110(7): p. 2545-55). HUVECs were cultured at $1 \times 10^5$ cells/slide on Ibidi 6-chamber slides (80606; Ibidi) before treatment with TNFα (500 U/mL) for 6-10 hours. An individual chamber outlet was then attached to a calibrated pump (74 900; Cole Partner, Vernon Hills, IL) and flow was generated by perfusing wash buffer (M199 with 0.15% BSA) or a monocyte suspension ($2.5 \times 106$ cells/mL) over the HUVEC monolayer. The flow rate was representative of shear rates in small venules (0.05 Pa). Observations made using phase-contrast microscopy (Model: Axiovert 100; Objective: 20×/0.3 NA air; Carl Zeiss) were recorded using a high-resolution camera (D70; Nikon, Zurich, Switzerland). Individual images were recorded every 30 seconds with Nikon capture software (v4.2) and compiled into movie sequences using Adobe Photoshop (CS6) and Image J (v1.5d), allowing analysis of individual monocytes over large areas. The tested compounds, e.g. compounds of the general Formula (I), were maintained at the specified concentration in all wash buffers throughout the course of the experiment. The compounds were preincubated separately on both HUVECs and monocytes 15 minutes prior to flow co-culture. HUVEC monolayers were washed for 10 minutes prior to a compound wash-in step to allow for this preincubation period. The monocyte suspension was then perfused over HUVECs for 4 minutes followed by 20 to 60 minutes with wash buffer. Time-lapse recording was started upon monocyte first-contact with the monolayer. Monocyte adhesion data are presented as the total number of monocytes per unit field. Transmigration events are presented as a percentage of total monocytes captured from flow per unit field. All experiments were carried out using quadruplicate fields and are presented as a mean value (±SEM).

Analysis

Figure 2:
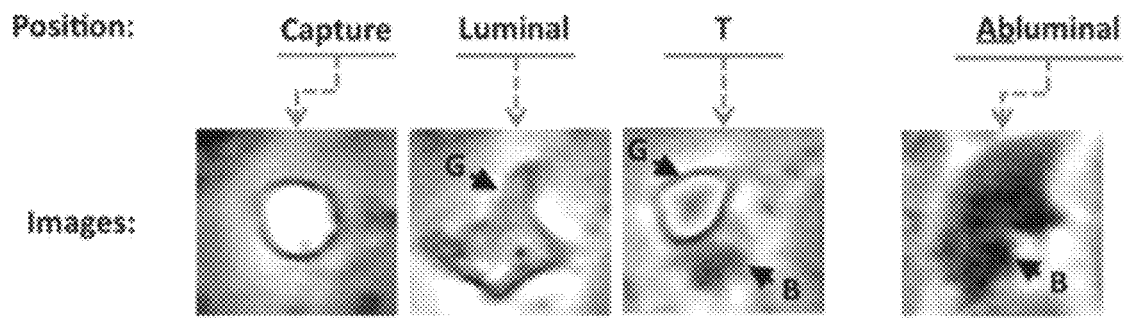
FIG. 2 shows a tracking profile of a human monocyte captured onto an activated HUVEC luminal surface (Timeline, position, and images).

Tracking Profile of a Human Monocyte Capture onto an Activated HUVEC Luminal Surface FIG. 2 shows the tracking profile of a human monocyte capture onto an activated HUVEC luminal surface (Timeline, position, and images).

A timeline is shown to represent the positioning and timing of an individual monocyte during movie analysis (marked 'Timeline'). Captured movie images (marked 'Images') represent the different phenotypes associated with monocyte capture and transmigration when using phase contrast microscopy. Monocyte position is determined by phase appearance and cell history (marked 'Position'). In this particular example, a single monocyte was captured 2 minutes after flow introduction of monocytes onto HUVEC luminal surface (Hashed box). This was rapidly followed by firm adhesion and luminal migration (3-7 minutes, gray boxes). This was consistent with the monocyte adopting an irregular shape and a phase-gray appearance (marked 'G'). Transmigration (Position 'T') occurred between 8 and 9 minutes (gray/black striped boxes) at an intercellular HUVEC junction where the monocyte adopted a composite phase-gray and black appearance (marked 'G' and 'T', respectively) as it moves into the abluminal compartment. Once transmigration was completed, the monocyte migrated within the abluminal compartment for the duration of the experiment (black boxes) and had a phase-black appearance (marked 'B').

Results

The monocytes were flowed over the TNF-activated HUVECs for the first 5 minutes of the experiment before switching to a wash buffer for 40 minutes. The adherent monocytes appeared as phase-white, which rapidly changes to phase-gray as the cells became firmly adherent. Monocytes that transmigrated through the HUVEC monolayer changed to a phase-black appearance, with reverse transmigration events marked by a return to the luminal compartment and a reversion to phase gray. This change in cell appearance and phases in migration allowed measuring every aspect of monocyte recruitment and retention. The control conditions indicated that the monocytes were in good shape. They adhered to the HUVECs and transmigrated in 15 minutes from the start of the experiment. The rank of the potency of the tested compounds is presented in Table 2.

TABLE 2

| Compound (30 μM) | Level of Transmigration Blockage (%) |
|---|---|
| DMSO | 0 |
| Formula 1 | 81 |
| Formula 2 | 100 |
| Formula 4 | 75 |
| Formula 6 | 78 |
| Formula 9 | 98 |
| Formula 10 | 92 |

Figure 3:
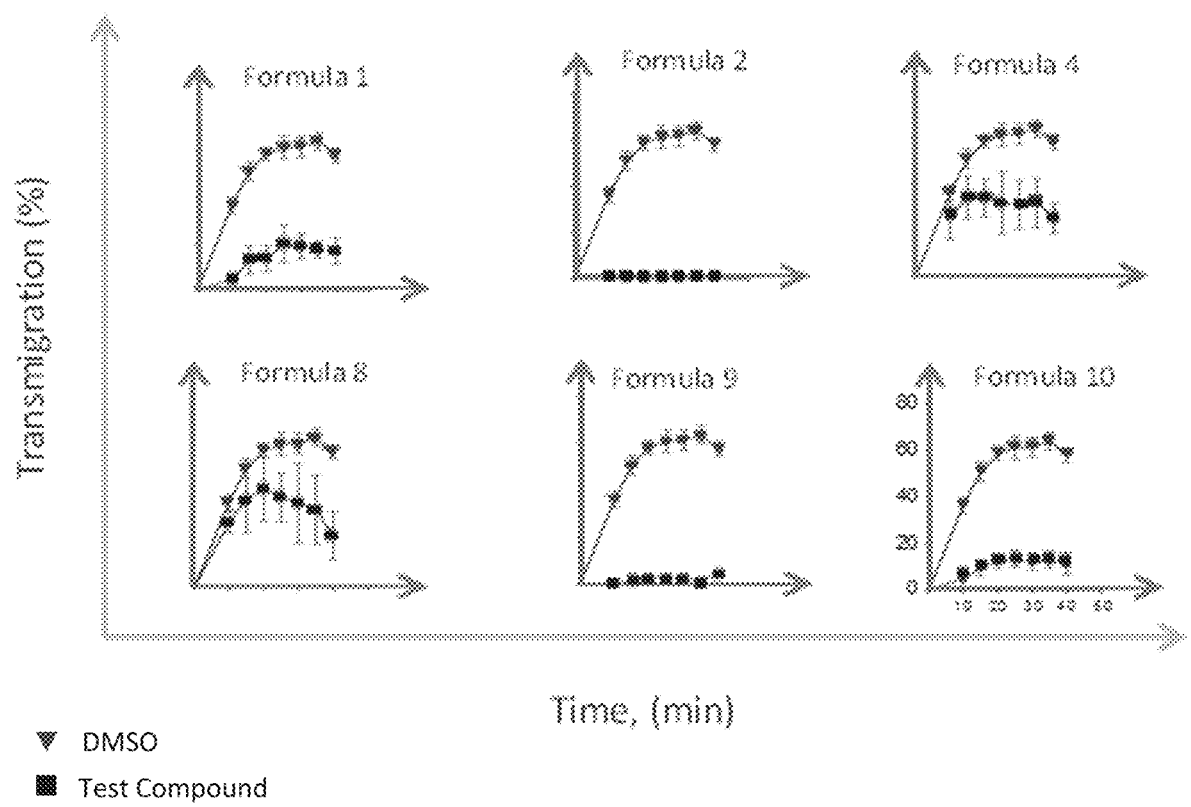
FIG. 3 provides the results of the biological study described in Example 4. Monocyte transmigration on the surface of activated HUVECs under flow. Primary human monocytes co-cultured on TNF-alpha-activated HUVECs. Compounds of general Formula (I) at 30 μM were added to cells for 45 minutes. Co-cultures were kept under flow at 0.05 Pa. The positive control is DMSO treated cells.

All of the tested compounds exhibited effective (75% or more) monocyte-rolling inhibition. Compounds of Formulae 9 and 10 exhibited above 90% monocyte-rolling inhibition; whereas compound of Formula 2 completely blocked monocyte transmigration. A summary of the results is presented in FIG. 3.

Figure 4A:
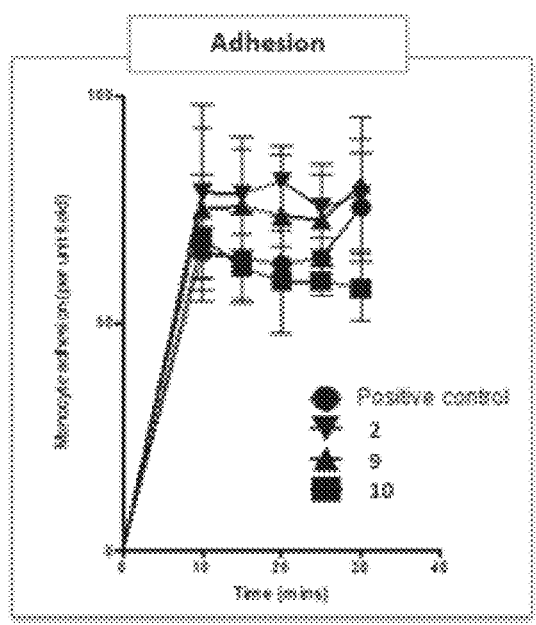
FIGS. 4A and 4B show adhesion (4A) and transmigration (4B) pattern of human monocytes co-cultured on TNF-alpha-activated HUVECs under flow in the presence of compounds of Formulae 2, 9 and 10. Co-culture was kept under flow (0.05 Pa) for 30 minutes. All compounds were introduced to cells in concentrations of 30 μM. n=3; the positive control received DMSO.
Figure 4B:
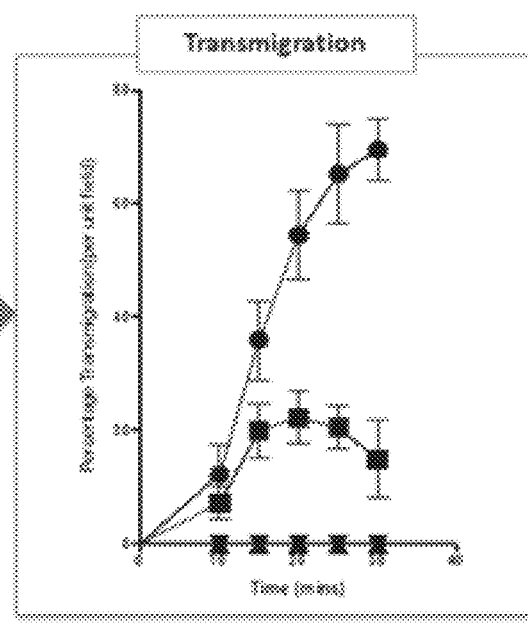

Another parameter that can be measured in the monocyte transmigration assay is the level of adhesion of monocytes to the endothelial cells. This parameter was used to determine whether the inhibitory effects of the compounds disclosed herein is related to their intervention with adhesion or to the transmigration pathway itself. The effect of compounds of Formulae 2, 9 and 10 was thus tested and the results are shown in FIGS. 4A and 4B. Monocyte adhesion was unaffected, as shown in FIG. 4A, by all of the three tested compounds. The only effect was observed on the transmigration process. Without being bound by any particular theory it may be hypothesized that the mechanism of action of the tested compounds may be via inhibition of the transmigration process and that the effect may be attributed to the adhesion of monocytes to the endothelial cells.

Figure 5A:
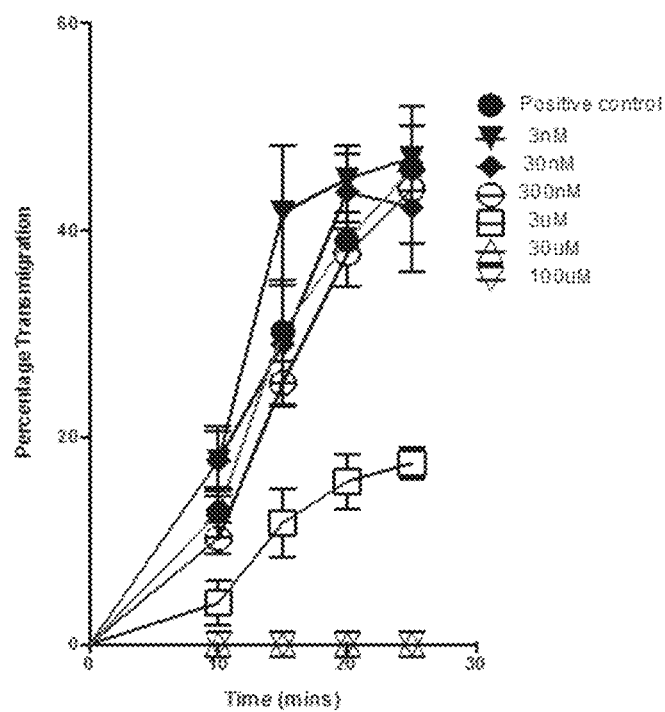
FIGS. 5A and 5B show the dose response effect of compound of Formula 2 (5A) and Formula 10 (5B) on monocyte transmigration on the surface of HUVECs under a flow of 0.05 Pa. Control cells received DMSO. n=3.
Figure 5B:
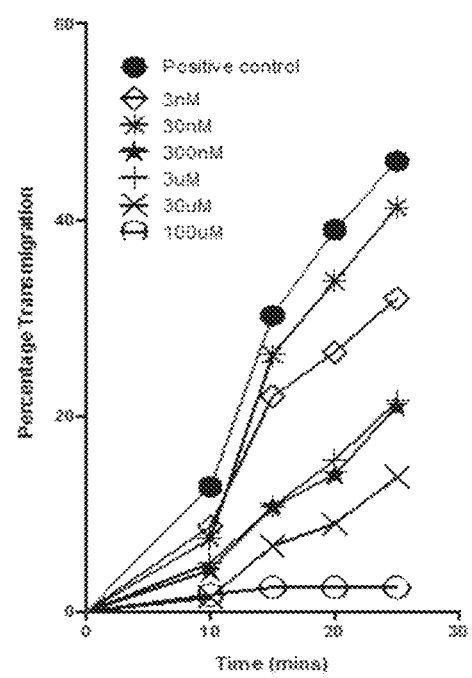
Figure 6A:
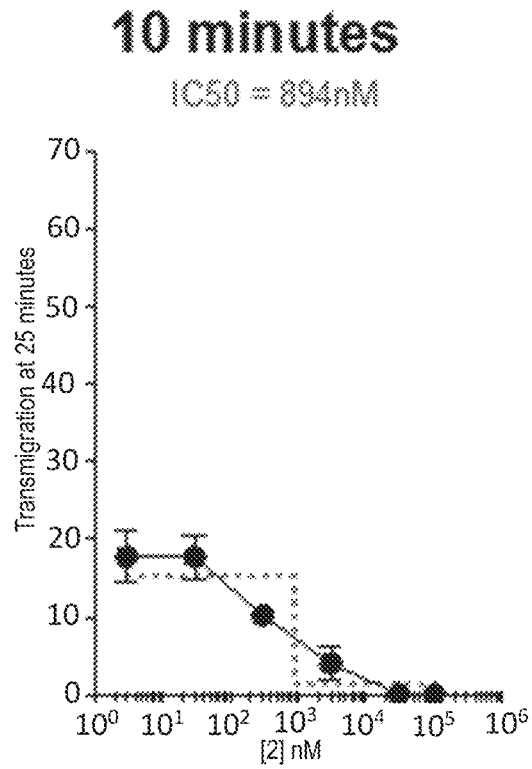
FIGS. 6A-6D show $IC_{50}$ and time dependent maximal inhibition effect of compound of Formula 2 at 10, 15, 20 and 25 minutes. Monocyte transmigration on the surface of HUVECs under a flow of 0.05 Pa was tested as described in Example 4 herein below. n=3.
Figure 6B:
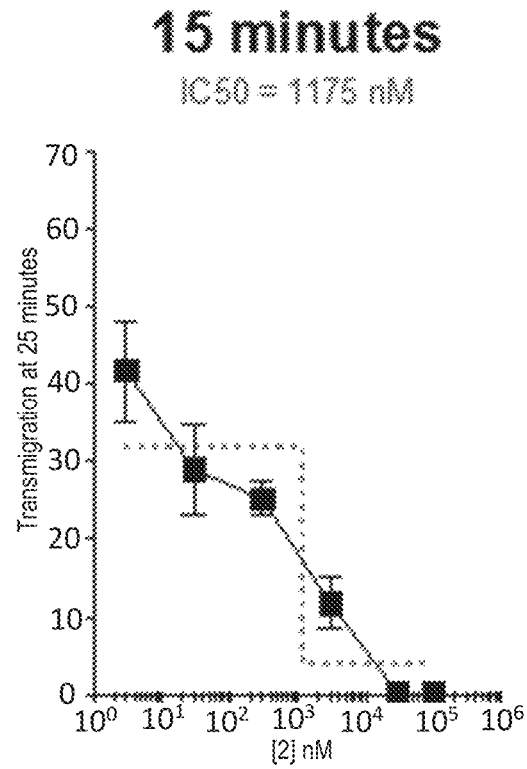
Figure 6C:
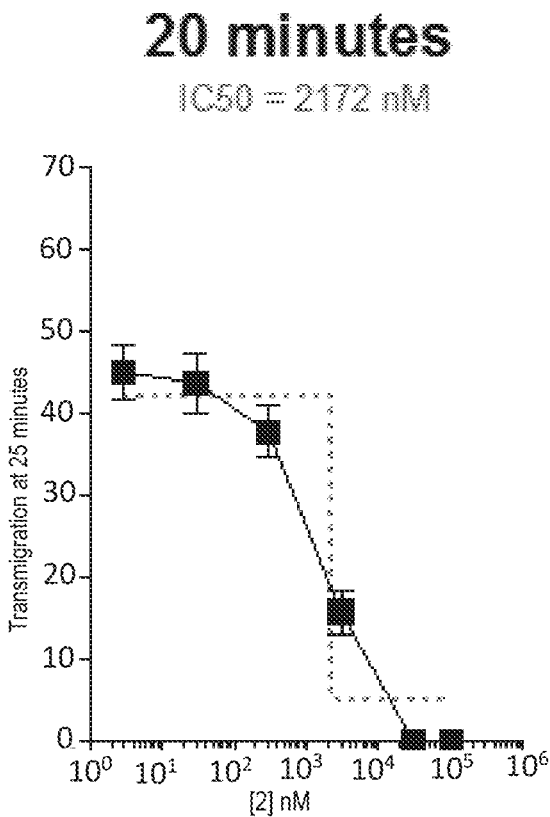
Figure 6D:
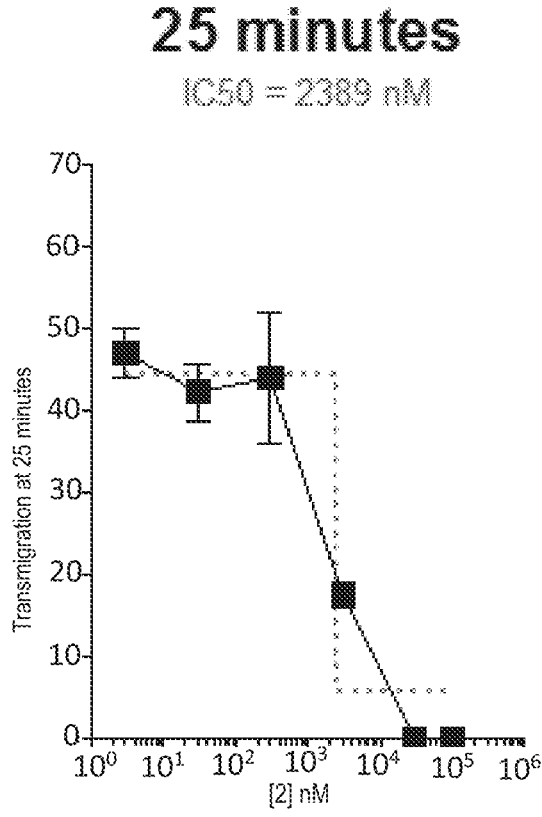
Figure 7A:
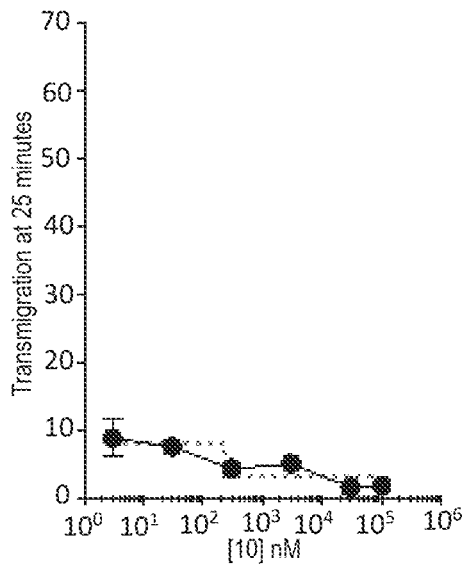
FIGS. 7A-7D show $IC_{50}$ and time dependent maximal inhibition effect of compound of Formula 10 at 10, 15, 20 and 25 minutes. Monocyte transmigration on the surface of HUVECs under a flow of 0.05 Pa was tested as described in Example 4 below. Control cells received DMSO. n=3.
Figure 7B:
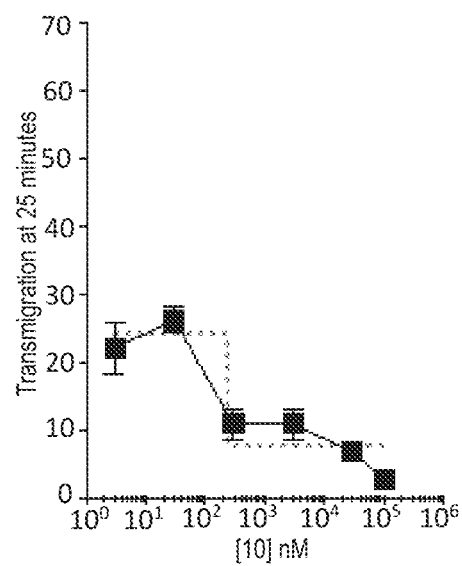
Figure 7C:
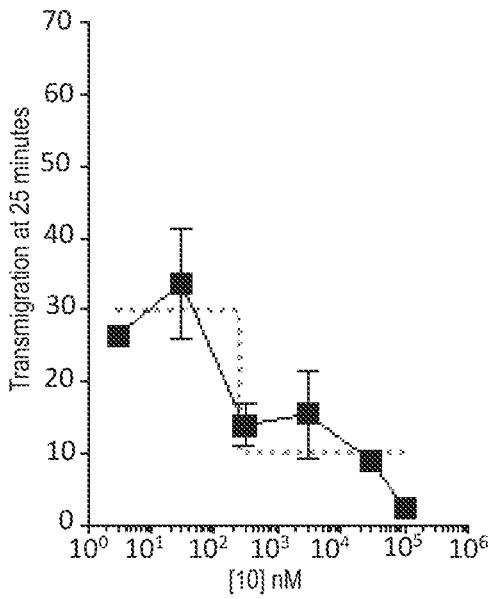
Figure 7D:
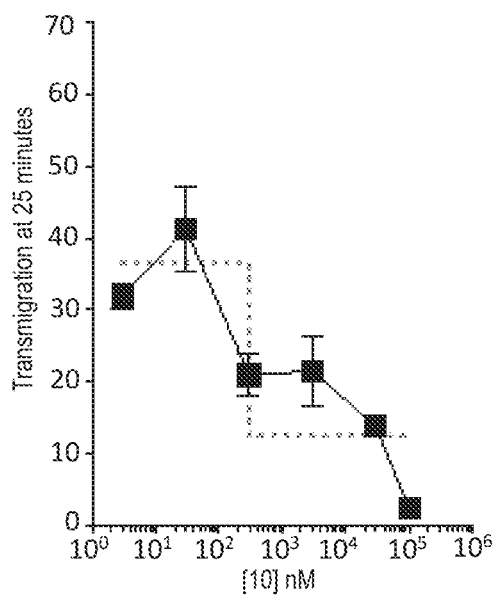

The dose response effect of compounds of Formulae 2 and 10 was investigated using the same monocyte/HUVEC system by identical flow assay which shows the dose response for compound of the compounds. Serial dilutions of both compounds starting from 100 µM to 3 nM were used. The results are provided in FIGS. 5A and 5B, with 5A showing the results for the compound of Formula 2 and 5B showing the results for the compound of Formula 10. FIG. 5A shows that compound of Formula 2 was not active in a concentration below 300 nM. However, in a 30-100 µM concentration the compound displayed full blocking of monocyte transmigration and in a concentration of 3 µM partial blocking was detected. Compound of Formula 10 was not active in concentrations below 30 nM, whereas at higher concentrations a partial effect was observed. Total blocking of transmigration was detected only at high concentrations (100 µM).

To summarize the data regarding the activity of compounds of Formulae 2 and 10, $IC_{50}$ values and the time of the maximal effect were determined, as shown in FIGS. 6A-6D and 7A-7D, respectively. The $IC_{50}$ value for compound of Formula 2 was 2.4 µM. The time of the maximal effect of compound of Formula 2 was 20 minutes. The maximal efficacy of compound of Formula 2 was detected as 48% of the inhibition. The maximal efficacy of compound of Formula 10 was detected as 40% of the incubation. The $IC_{50}$ value for compound of Formula 10 was 0.3 µM. The time of the maximal effect of compound of Formula 10 was 25 minutes.

Example 5

Evaluation of Compound of Formula 2 In Vivo, in an Intraperitoneal Inflammatory Mouse Model (Thioglycollate Peritonitis Model)

C57BL/6J (The Jackson Laboratory) female mice were chosen for this experiment. The acute inflammation was induced by thioglycollate injection into the abdominal cavity as described by Hoover-Plow J. L. et al. (Strain and model dependent differences in inflammatory cell recruitment in mice. Inflammation Research, 2008. 57(10): p. 457-463).

Mice were injected intraperitoneally with 0.5 mL of 4% thioglycollate (Becton Dickinson, Cockeysville, MD) and after 6 or 72 hours corresponding to peak neutrophil (6 hours) and macrophage (72 hours) recruitment, peritoneal lavage fluid, and cells were harvested as previously described by Ploplis, V. A. et al. (Plasminogen deficiency differentially affects recruitment of inflammatory cell populations in mice. Blood, 1998. 91(6): p. 2005-2009). The number of neutrophils and macrophages (Tang, L. P. and J. W. Eaton, Fibrin (Ogen) Mediates Acute Inflammatory Responses to Biomaterials. Journal of Experimental Medicine, 1993. 178(6): p. 2147-2156) accumulating in the lavage were determined from the enzyme activity of myeloperoxidase for neutrophils (Himmelhoch, S. R., et al., Purification of myeloperoxidases from the bone marrow of the guinea pig. Biochemistry, 1969. 8(3): p. 914-21) and non-specific esterase for macrophage/monocytes (Torres, J. L., R. S. Rush, and A. R. Main, Physical and chemical characterization of a horse serum carboxylesterase. Arch Biochem Biophys, 1988. 267(1): p. 271-9).

After inducing the inflammation (peritonitis), compound of Formula 2 was injected at a concentration of 12.5 mg/kg (DMSO, 01% in PBS, IP), twice (one day after the other). The next day, mice were sacrificed and the peritoneal liquid was collected from the control and treated mice (n=3 for each group). Two assays were conducted for the estimation of the possible anti-inflammatory effect of compound of Formula 2: leukocyte counting (the total amount and the calculation of the percentage of different leukocyte fractions) and a flow cytometry.

Leukocyte Counting

Figure 8:
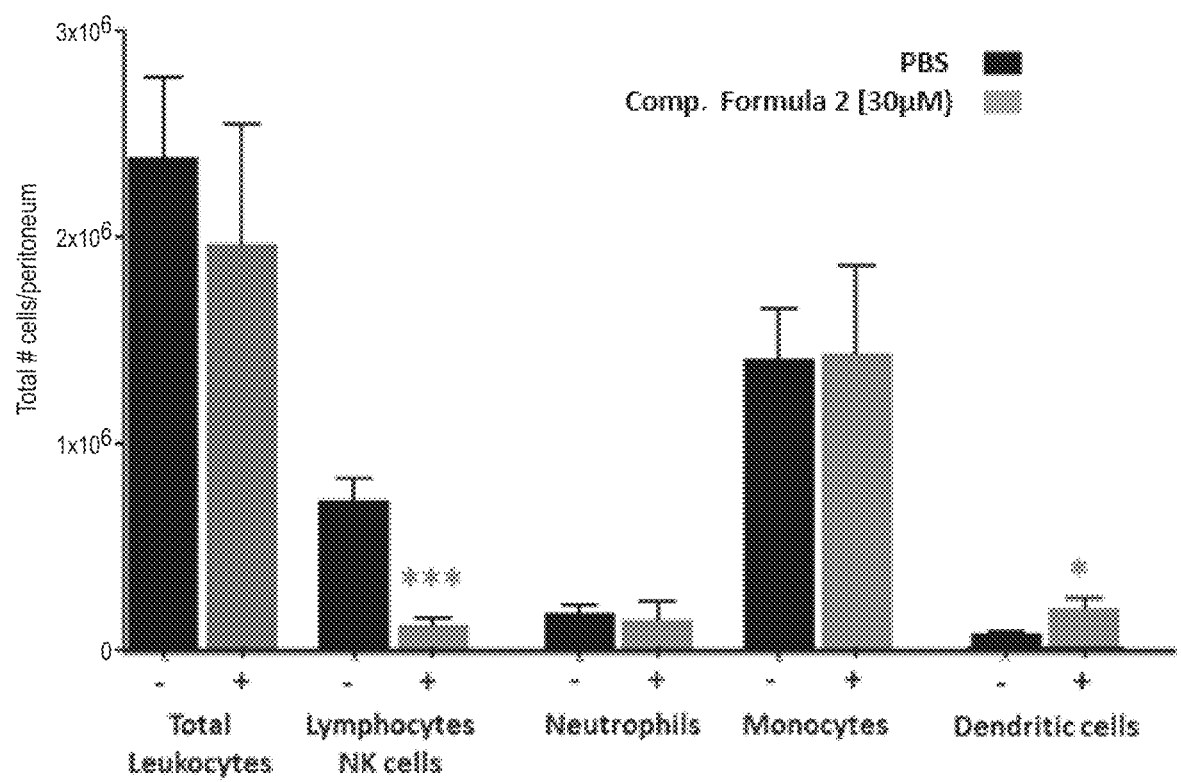
FIG. 8. White blood cell (WBC) counts of peritoneal fluids were reduced by application of compound of Formula 2, in a mouse model of aseptic peritonitis (Example 5 below). A 4% solution of thioglycollate in water (1 ml) was used to induce peritoneal inflammation by IP injection. The solution was injected twice during 48 hours. Compound of Formula 2 (30 μM) was injected on the third day, once. Mice were sacrificed, peritoneal fluids were collected and centrifuged. The cells pellet was resuspended and cells were counted and analyzed by the automated cell counter. n=6.

As shown in FIG. 8, compound of Formula 2 significantly (85%) reduced the amount of lymphocytes in the peritoneal liquid. In addition, the amount of dendritic cells that are antigen-presenting cells of the mammalian immune system was significantly increased (2.5-fold). Together with the predictable inhibitory effect of the compound on the transmigration of lymphocytes to the area of inflammation, this augmentation of the amount of dendritic cells is an unexpected result. However, without being bound by any theory, this phenomenon is believed to be in agreement with the fact that during non-successful recruitment of lymphocytes to the area of inflammation, dendritic cells undergo stimulation to produce a physiological immune reaction due to their main function, which is to process antigen material and present it on the cell surface for stimulating the T cells of the immune system. These results show that negative feedback was induced by compound of Formula 2 in the immune system to try overcoming the lack of a sufficient amount of lymphocytes in the inflammation area. Importantly, the total amount of leukocytes in the abdominal liquid was not affected by the compound of Formula 2. This may indicate that the effect of the compound is specific to several populations of leukocytes but not to all of them. In addition, the amount of neutrophils and monocytes was not affected in the presence of compound of Formula 2.

Ten-Color Flow Cytometry Assay

Flow cytometry based on a fluorescent protein marker (CD115) was selected for the analysis. It is generated by monocytes and localized to their plasma membrane as described by Yang, J. et al. (Monocyte and macrophage differentiation: circulation inflammatory monocyte as biomarker for inflammatory diseases. Biomark Res, 2014. 2(1): p. 1). This protein is able to specifically recognize and bind a F4/80 antibody that activates the immune system macrophages (Lin, H. H., et al., The macrophage F4/80 receptor is required for the induction of antigen-specific efferent regulatory T cells in peripheral tolerance. Journal of Experimental Medicine, 2005. 201(10): p. 1615-1625).

Cell viability before the FACS experiment was assessed by incubation in the amine-reactive dye Aqua (Invitrogen) (1:500) dilution in $Ca^{2+}$ and $Mg^{2+}$-free PBS) for 30 minutes in the dark at room temperature (RT), followed by a single wash in PBS. For all experiments, cells were incubated in 0.5 µg Fc Block (BD Biosciences) for 10 minutes at room temperature (RT). Surface staining was performed in the dark for 30 minutes at 4° C. in staining buffer. A surface marker (CD115, APC clone AFS98, in dilution 1:100, from eBioscience) was used. In addition, the following antibodies against CD115 were applied: F4/80 clone CI:A3-1 Alexa Fluor 647 (various dilutions, optimized at 1:200, AbD Serotec, Raleigh, NC, USA), F4/80 clone BM8 Alexa Fluor 700 (various dilutions, AbD Serotec), F4/80 clone BM8 APC (various dilutions, optimized at 1:100, eBioscience), F4/80 clone BM8 FITC (various dilutions, eBioscience), F4/80 clone BM8 PE (various dilutions, eBioscience), F4/80 clone BM8 PE-Cy7 (various dilutions, eBioscience), F4/80 clone BM8 PE-Texas Red (various dilutions, eBioscience), F4/80 clone BM8 PerCP-Cy5.5 (various dilutions, eBioscience). Flow cytometry experiments were acquired on an LSR II cytometer (BD Immunocytometry Systems, San Jose, CA, USA) equipped with 405 nm, 488 nm, 561 nm, and 640 nm excitation lasers. All data collection and sorting were performed using BD FACS Diva software (BD Biosciences) and data analyses were performed using FlowJo software (Tree Star, Ashland, OR, USA). Fluorescence minus one (FMO) controls were used for gating analyses to distinguish positively from negatively staining cell populations. Compensation was performed using single color controls prepared from BD Comp Beads (BD Biosciences) for cell surface staining or Arc Beads (Invitrogen) for Aqua live/dead discrimination. Compensation matrices were calculated and applied using FlowJo software (Tree Star). Bi-exponential transformation was adjusted manually when necessary.

Figure 9:
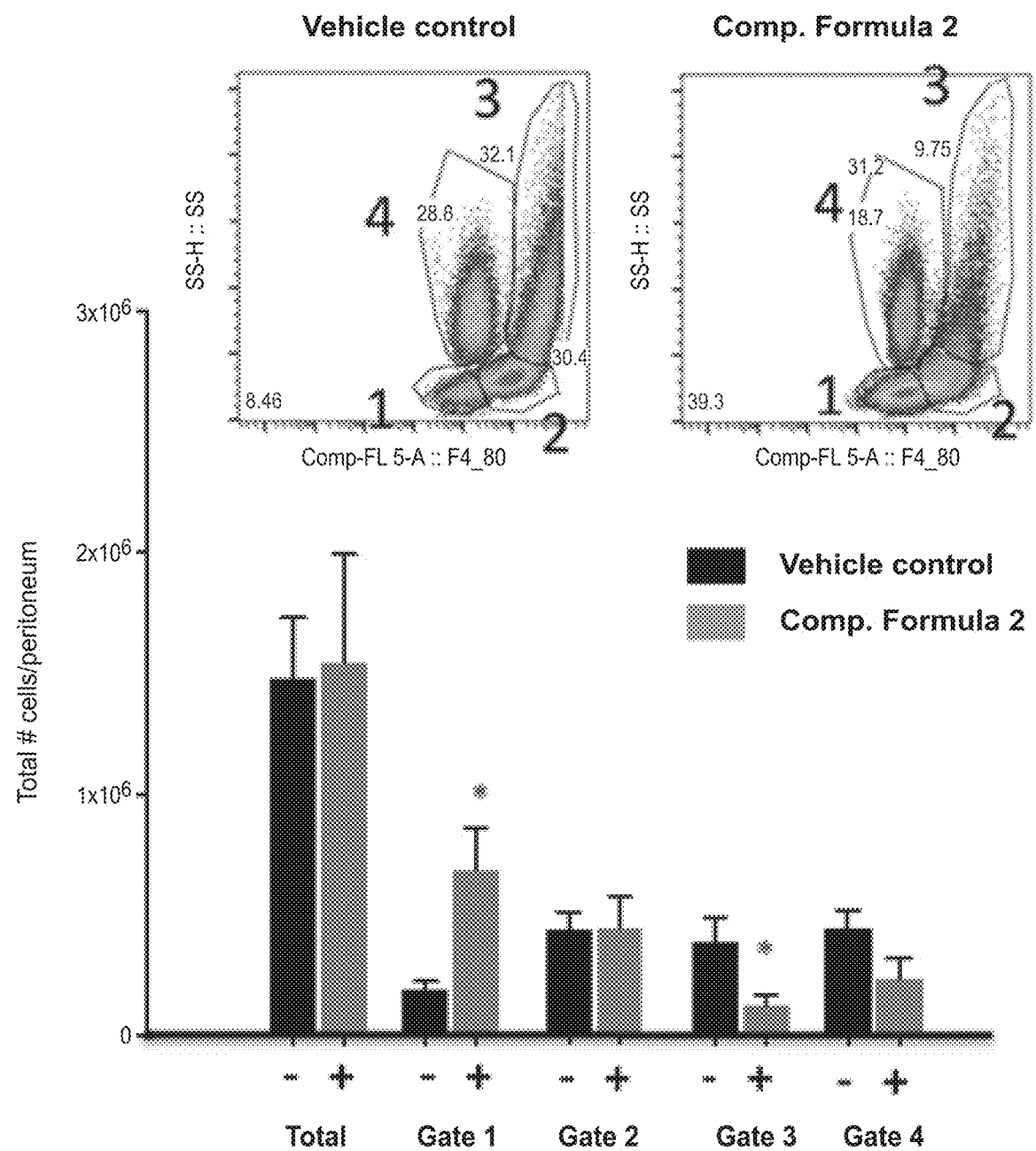
FIG. 9 shows ten-color flow cytometric analysis of CD115 expression on mouse monocytes followed by compound of Formula 2 treatment. C57BL/6 mouse monocytes were stained with PE Rat Anti-Mouse CD115 antibody reacted with ten-color F4/80 fluorescent antibodies against CD115. Separate fractions of cells were analyzed according to side-light scattering characteristics. Monocytes treated with compound of Formula 2 showed a distinct phenotype associated with reduced differentiation, exhibited by a shift in pattern of gates 1-4.
Figure 10A:
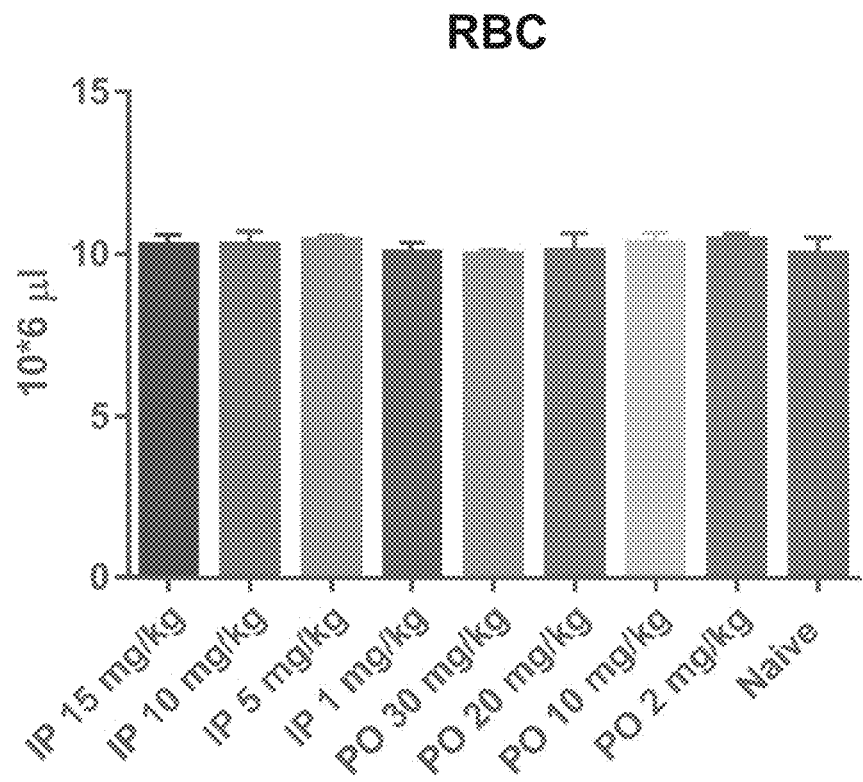
FIGS. 10A-10G show no effect of the compound of Formula 2 administered with 3 doses by oral gavage (PO) or with 3 doses by intraperitoneal injection (IP) on different subtypes of red blood cells, platelets and hematocrit. Data shown mean±SEM, n=5.
Figure 10B:
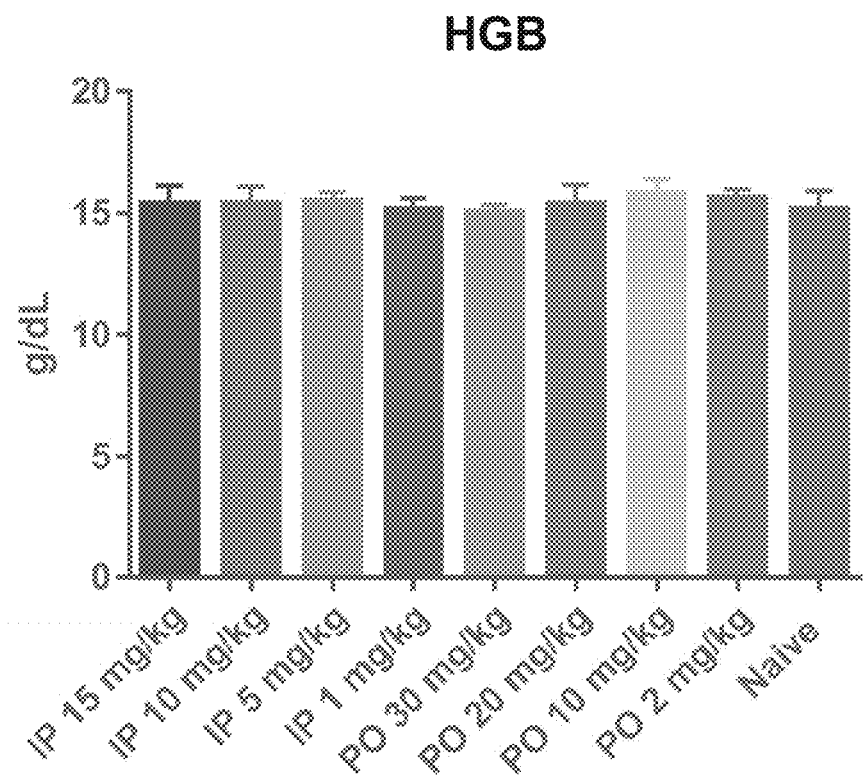
Figure 10C:
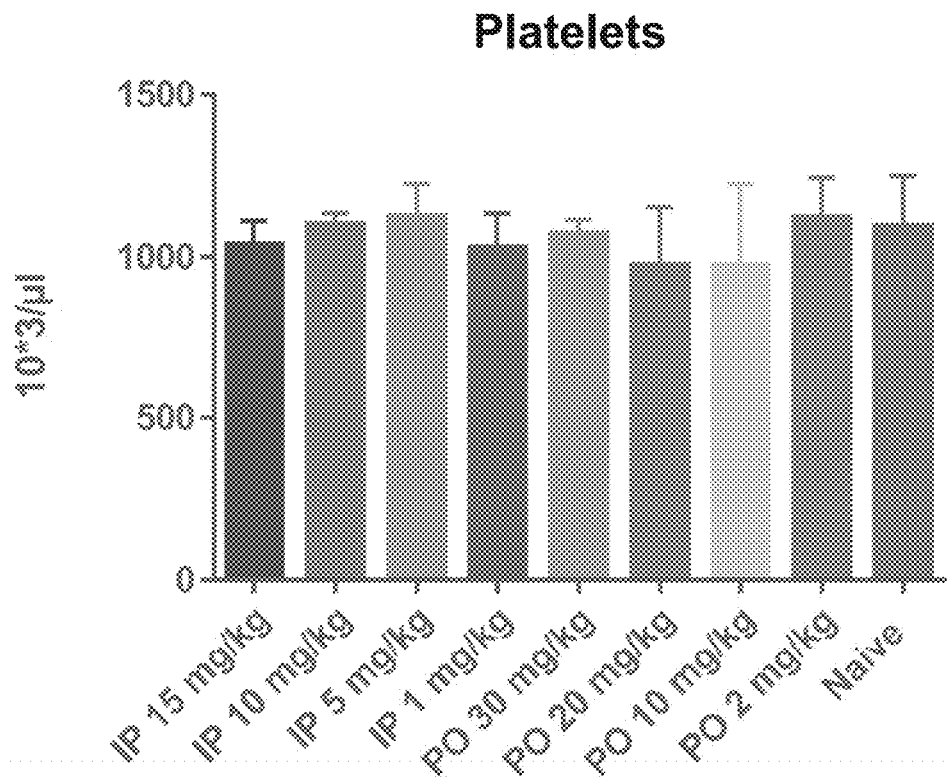
Figure 10D:
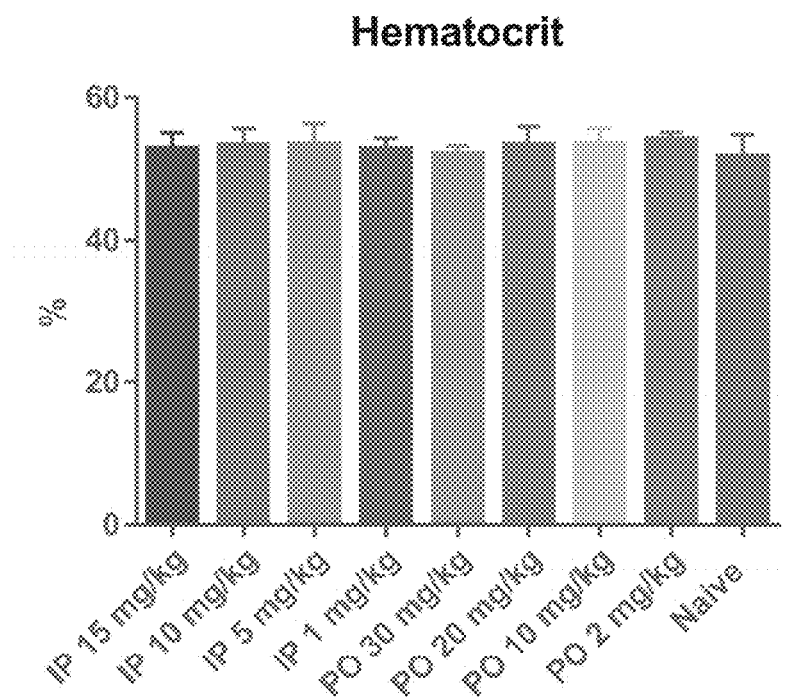
Figure 10E:
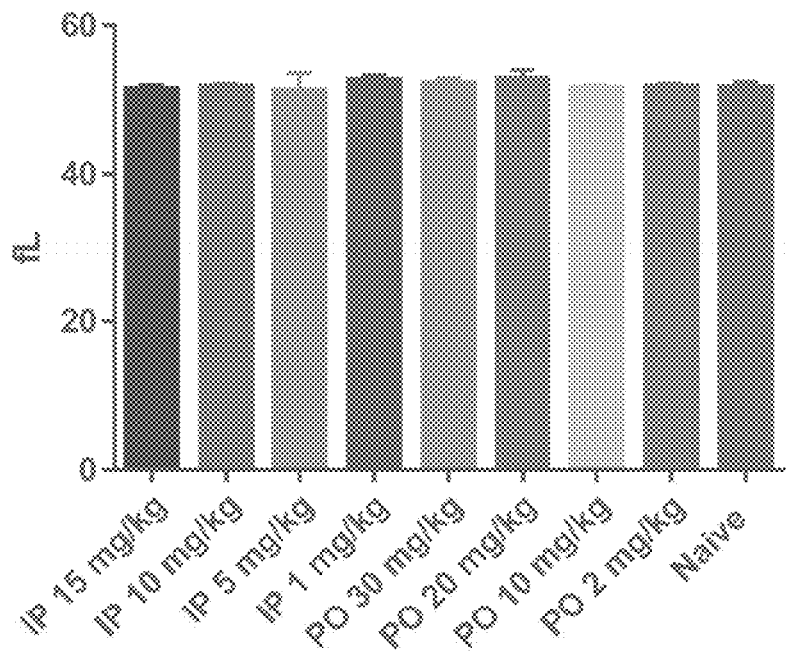
Figure 10F:
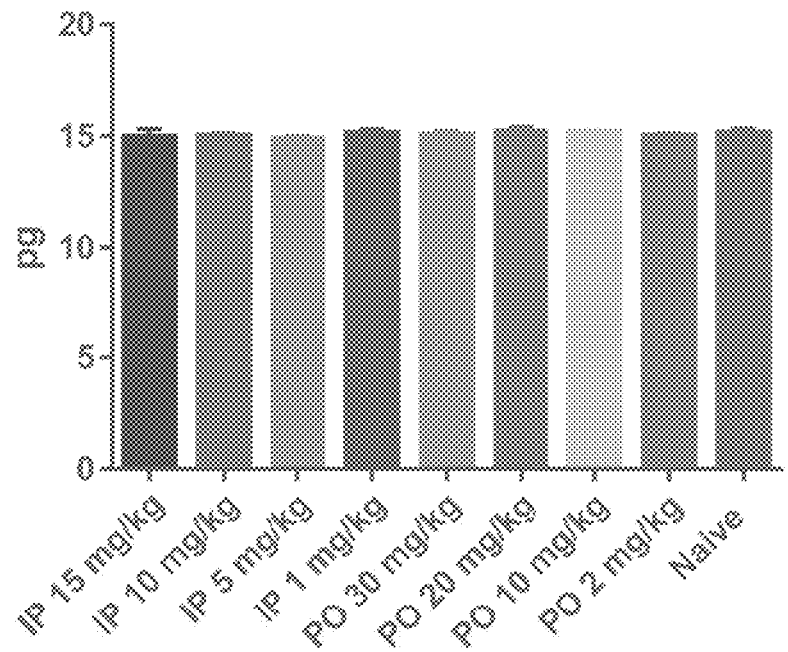
Figure 10G:
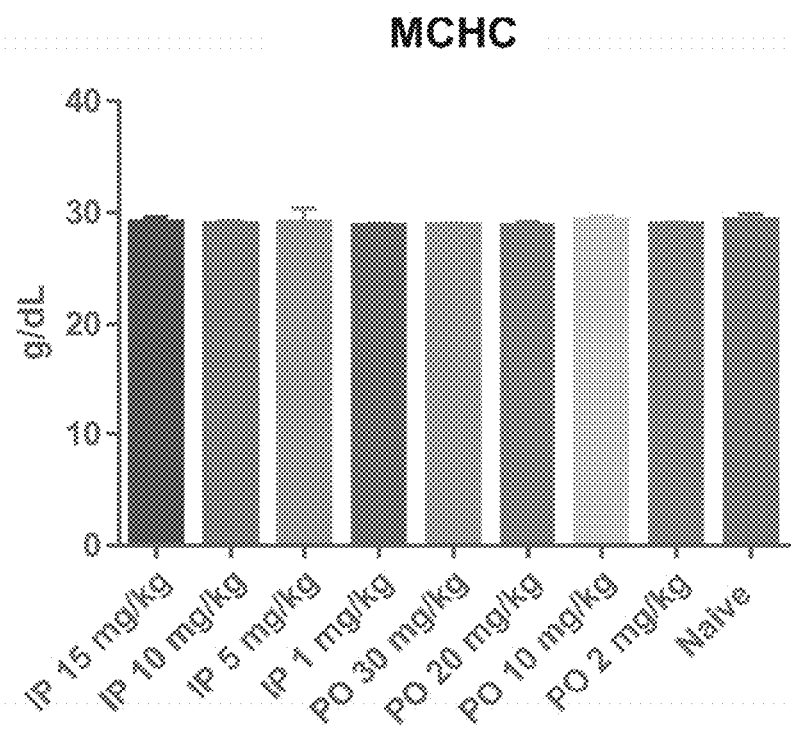

Using this interaction, only fluorescent positive macrophages from the abdominal cavity, which were treated by compound of Formula 2 and non-treated mice, were detected by FACS. The obtained results are presented in FIG. 9. Compound of Formula 2 considerably decreased the amount of activated (high macrophages) and elevated the level of non-activated (low macrophage). This could be seen by the shift in the intensity of the fluorescent signal in FIG. 9 from gate 2+3 to gate 1.

Example 6

Safety Profile of Compound of Formula 2 in Naive Mice In Vivo

Preparation of Methylcellulose Based Suspension for In Vivo Administration of Compound of Formula 2

1% methyl cellulose in DDW solution was prepared by adding 0.5 g methyl cellulose into 50 ml of DDW and stirring the solution at the lowest possible speed (without making bubbles) overnight at room temperature. Formula 2 stock solution was prepared in concertation of 20 mg/ml at room temperature following shown below order of actions:
1. 30 mg of the compound of Formula 2 was placed in the glass vial together with small magnet.
2. 1.5 ml of 1% methylcellulose was added by circular (swirled) movement very slow. The entire surface of the vial was gently covered by the solvent and powder was not allowed to float above the liquid.
3. The resulting suspension was stirred at the lowest possible speed up to 48 hours at room temperature.
4. Intermediate Formula 2 stock solution at 10 mg/ml concentration was prepared by diluting 20 mg/ml stock solution 1:1 (v/v) with equal amount of DDW. DDW was added to the Formula 2 stock solution. The obtained suspension was stirred at the lowest possible speed for another hour at room temperature.
5. Formula 2 working solution at 3 mg/ml was prepared by diluting intermediate stock solution (v/v) with DDW accordingly. The working suspension of Formula 2 was stirred at the low speed (~80-100 rpm) for 30 minutes to 1 hour prior to use in animal experiments.

Acute Toxicology (Biochemical Tests and Histology)

Eight experimental groups with 5 female 6-7 weeks old C57BL/6J mice each and one control group non treated (naïve) mice were used for the experiment. Mice were administered with daily application of the working suspension of the compound of Formula 2, prepared as described hereinabove, at 5, 10 and 15 mg/kg by intraperitoneal injection (IP) or at 10, 20 and 30 mg/kg by oral gavage (PO). Mice from all experimental groups were observed for sign of toxicity immediately post dosing and following 2 hours post each administration daily. Mice from all groups were euthanized with isoflurane 24 hours post last dose administration. Sampling for whole blood counts (WBC) and white blood differentiation: 200 µl of whole blood were collected into EDTA tubes (Greiner MiniCollect K3EDTA tubes). For comprehensive metabolic panel the rest of the whole blood (300-400 µl) was collected for the serum preparation. All blood tests were conducted in American Medical Labs, Herzeliah, Israel. Liver, spleen, lungs, heart and kidneys were collected from each mouse placed to vials with 4% buffered formalin following paraffin embedding and sectioning. Sections from each organ of each animal were stained with H&E and histological evaluation of the tissue was performed.

Results

Figure 15:
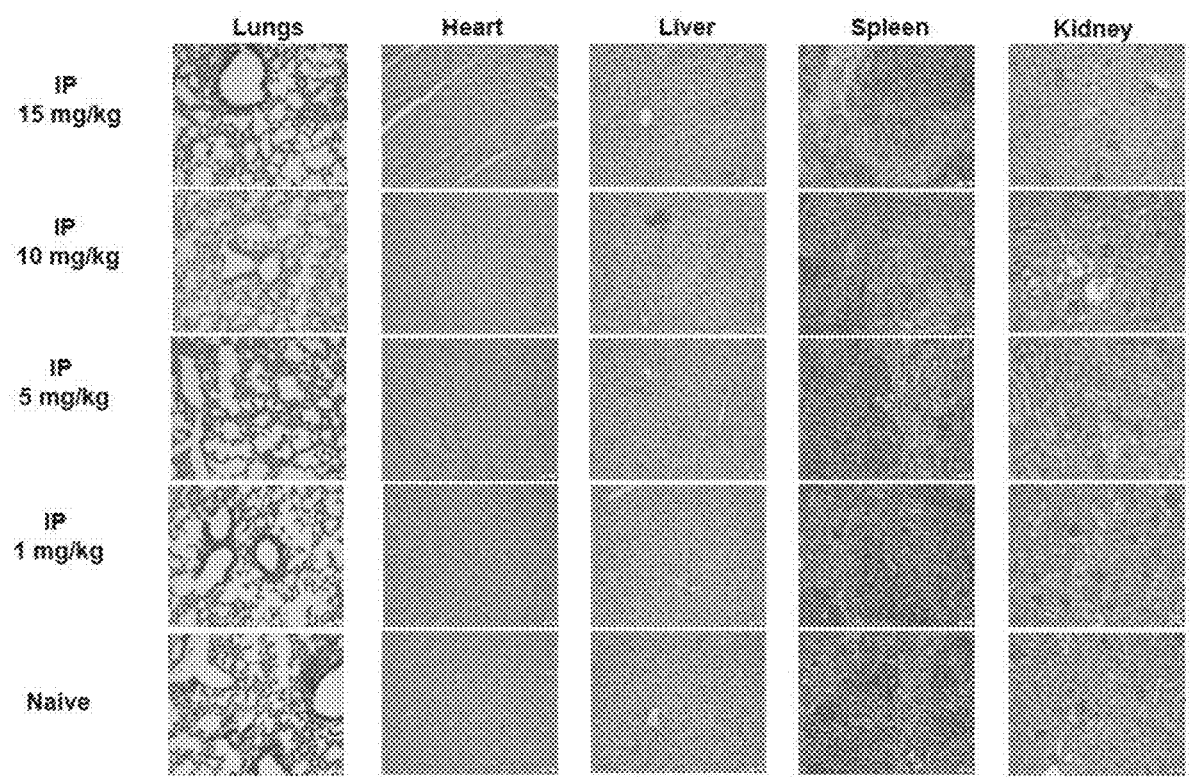
FIG. 15 shows no effect of the compound of Formula 2 administered with 3 doses by intraperitoneal injection (IP) on microstructure of lungs, heart, liver, spleen and kidney tissues. Data shown mean±SEM, n=5.
Figure 16:
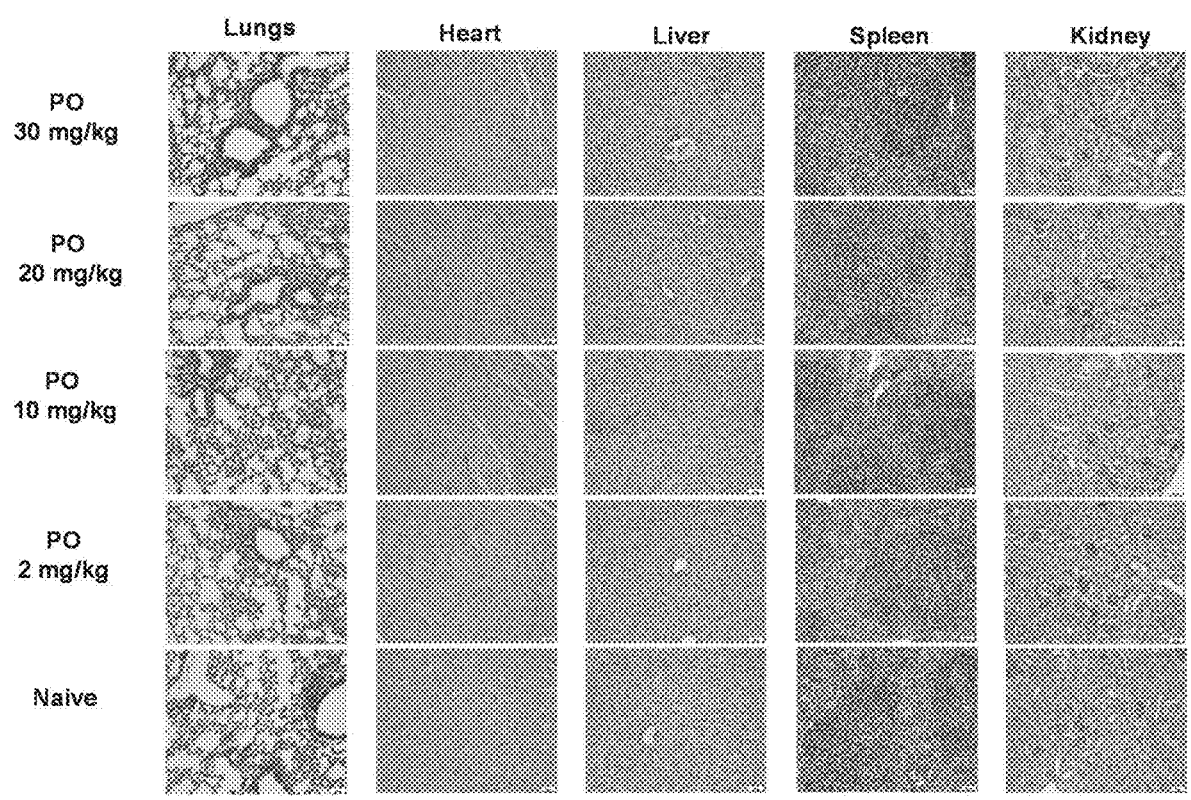
FIG. 16 shows no effect of the compound of Formula 2 administered with 3 doses by oral gavage (PO) on microstructure of lungs, heart, liver, spleen and kidney tissues. Data shown mean±SEM, n=5.

The results of these tests are provided in FIGS. 10 to 16. As can be seen from these figures, no significant changes in whole blood counts and white cells differentiation were observed in all mice treated with the compound of Formula 2, at all concentrations and routes of administration used (FIGS. 10A-10G and 11A-11F). All tested metabolic values were in normal range in mice treated with the compound of Formula 2 as shown in FIGS. 12A-12F, 13A-13E and 14A-14F. Microscopic evaluation of all mice tissues showed no changes in the tissues morphology in mice treated with the compound of Formula 2 as shown in FIGS. 15 and 16.

Example 7

Evaluation of Compound of Formula 2 In Vivo in a Model of B-Cell Lymphoma in NOD.CB17-Prkdcscid/J Mice B-Lymphoma Homing Assay Effect on the homing of the B-lymphocytes was tested in a model of B-cell lymphoma. Compound of Formula 2 (7.5 µM) was injected IV, together with $10 \times 10^6$ human B-lymphoma cells. After one and a half hours the amount of B-lymphocytes was tested in different organs.

Results

Figure 17:
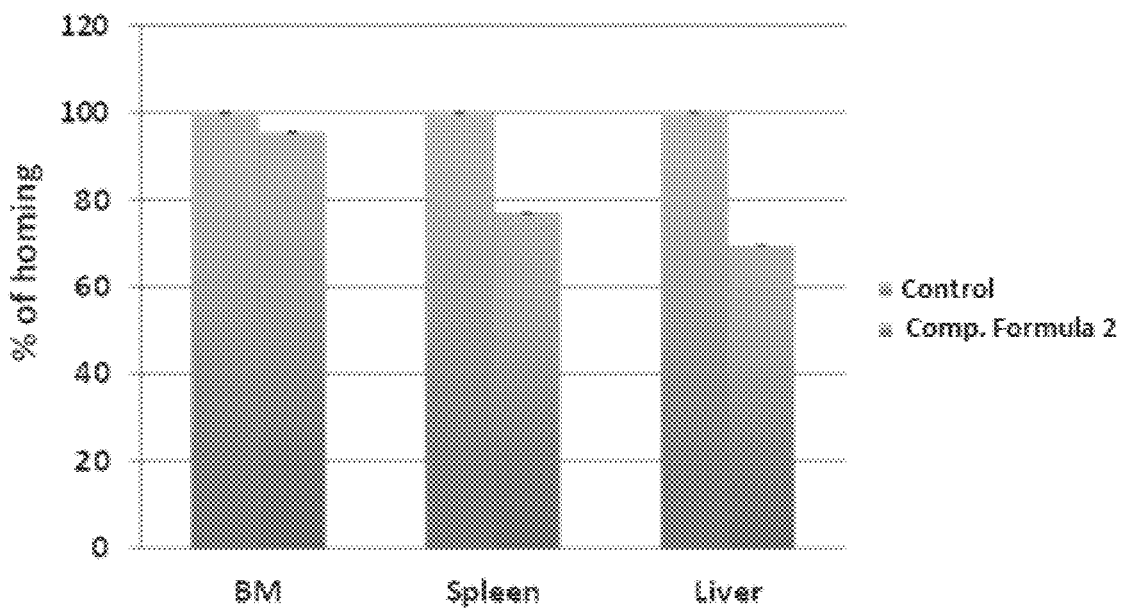
FIG. 17 shows that the compound of Formula 2 significantly blocked the homing of the leukemic cancer cells to the spleen and liver (Example 7 below).
Figure 18:
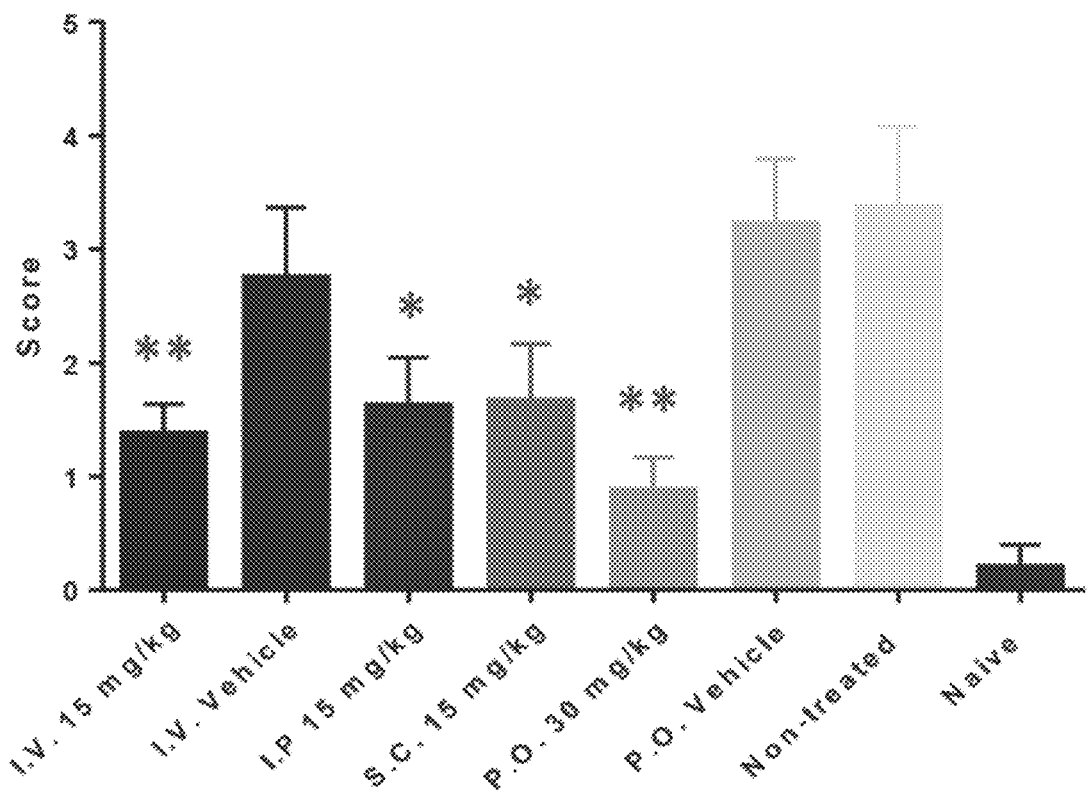
FIG. 18 shows the therapeutic effect of the compound of Formula 2 in acute dextran sodium sulfate (DSS) induced colitis model in C57BL/6 mice on Disease Activity Index (DAI) score administered at 2 doses by intravenous injection (IV), oral gavage (PO), intraperitoneal injection (IP) or subcutaneous injection (SC) (Example 8 below). Data shown mean±SEM, n=10

Significant difference in B-lymphocyte homing was detected between mice that were treated with compound of Formula 2 and untreated mice. In spleen the reduction of homing was around 22% and in liver around 33%. The results are shown in FIG. 17 and it is evident that the compound of Formula 2 significantly blocked homing of the cancer cells to the spleen and liver.

Example 8

Evaluation of Compound of Formula 2 In Vivo in an Acute Dextran Sodium Sulfate (DSS) Induced Colitis Model in C57BL/6 Mice (DAI Score and Colon Length)

The colitis was inducted by adding 1.5% DSS to the drinking water of female C57BL/6J (7-8 weeks old) mice for 5 consecutive days (days 0-4) for all animals in the experimental groups. On day 5, DSS containing water was changed for regular drinking water and treatment was initiated. The working suspension of the compound of Formula 2 was administrated at 15 mg/kg by IV, IP or SC injections at q3w regimen (administered 3 times per week) and at 30 mg/kg by PO at qd regimen (once daily). Treatment continued for 10 days and thereafter mice were euthanized.

Determination of individual body weight of animals was made prior to each dosing and the administered volume was adjusted accordingly. Additional body weights throughout the entire experimental period were taken on a daily bases. The severity of colitis Disease Activity Index (DAI) score was monitored daily according to the criteria shown in Table 3 and calculated as a sum of the weight loss score, the diarrheal score and the hematochezia score. Disease activity index (DAI) based on the methods reported by Friedman et al. (PNAS, 2009) was used.

TABLE 3

Scoring criteria for disease activity index.

| Score | Weight loss (%) | Stool consistency | Hematochezia |
|---|---|---|---|
| 0 | None | Normal | Absence |
| 1 | 0-10 | Normal | Absence |
| 2 | 11-15 | Loose stool | Absence |
| 3 | 16-20 | Loose stool | Absence |
| 4 | >20 | Diarrhea | Presence |

Mice from all groups were euthanized with isoflurane 24 hours post last dose administration. Colon was collected from each mouse, filled with 4% buffered formalin and colon length was measured. Large intestines were fixed, embedded in paraffin, sections and H&E stained using modified Swiss roll technique. Histological Score evaluation was performed based on: inflammatory cells infiltration and tissue damage, in four compartments of the large intestine graded from 0 to 3. Focally increased numbers of inflammatory cells in the lamina propria were scored as 1, confluence of inflammatory cells extending into the submucosa as 2 and transmural extension of the infiltrate as 3.

For tissue damage, discrete lymphoepithelial lesions were scored as 1, mucosal erosions as 2, and extensive mucosal damage and/or extension through deeper structures of the bowel wall as 3. The length of ulceration was measured in mm. The two equally weighted subscores (cell infiltration and tissue damage) at each compartment of the intestine were added as a colitis severity score. Ordinary one-way ANOVA statistical analysis was performed.

Results

Figure 19A:
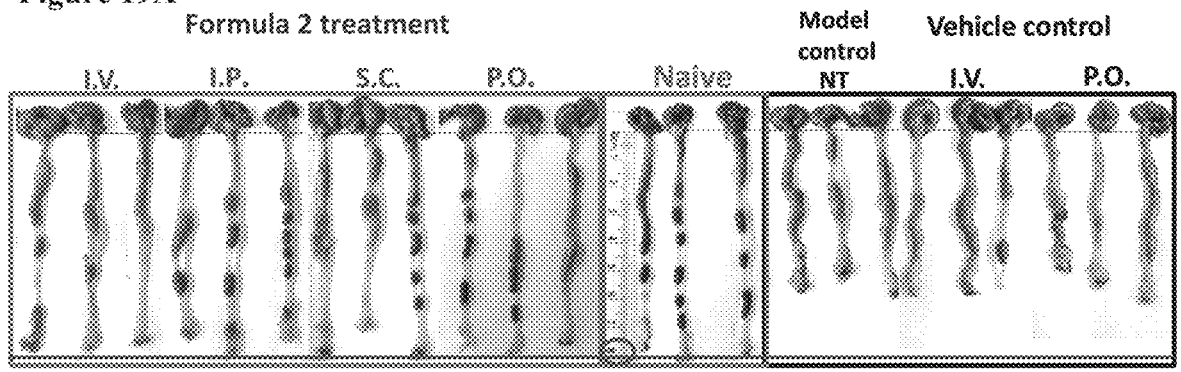
FIGS. 19A-19C show the therapeutic effect of the compound of Formula 2 in acute dextran sodium sulfate (DSS) induced colitis model in C57BL/6 mice on colon length (19A and 19B) and histological score of mice large intestine (19C). Data shown mean±SEM, n=10
Figure 19B:
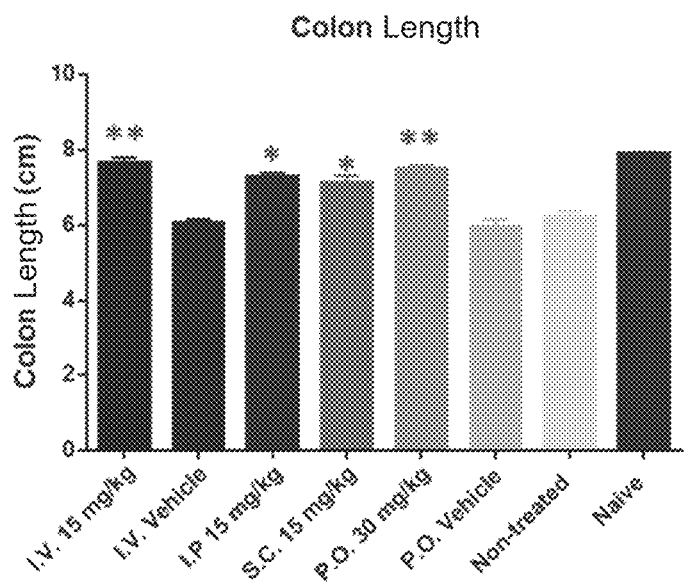
Figure 19C:
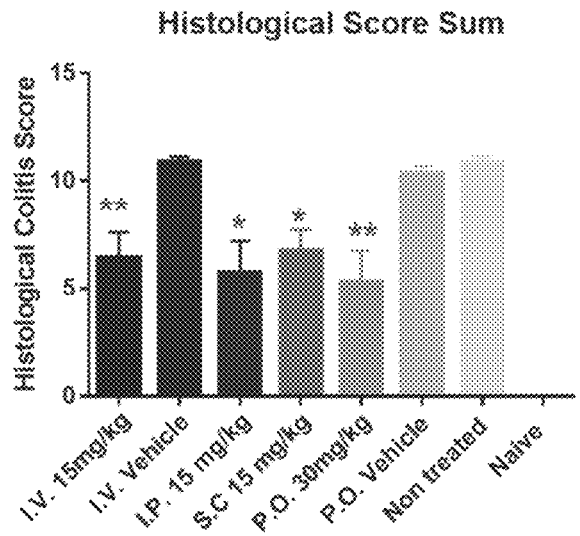

The obtained results are summarized in FIGS. 18 and 19A-19C. Formula 2 significantly decreased the DAI score in all treated groups, maximal effect was observed in PO treated mice. Colon length was similar to that of the naïve (no colitis) mice in all treated groups compared to control groups where colon length was shorter by approximately 2 cm (FIGS. 19A and 19B). In addition, stool formation that readily becomes paste on the anus was not detected in treated groups compared to control mice. Weight loss score in treated groups was significantly lower compared to the control groups. Histological score was obtained based on Park et. al. (2005, J. of Cancer Prevention) parameters were significantly lower in Formula 2 treated mice compared to control mice as shown in FIG. 19C.

Example 9

Evaluation of Compound of Formula 2 In Vivo, in a $MOG_{35-55}$/CFA-Induced Direct Experimental Autoimmune Encephalomyelitis (EAE) in Mice Female 7-8 weeks old C57BL/6J mice were immunized with an emulsion of $MOG_{35-55}$ in CFA according to standard protocol, followed by administration of pertussis toxin (PTX) in PBS. After the onset of EAE (9 days), mice were assigned by rolling enrollment to the groups one at a time as they show the first signs of EAE (paralysis score 0.5-1). Treatment group was administered with Formula 2 at 15 mg/kg dose at q3w regiment by SC injections, mock treated (vehicle) control group was administered with similar volume as a treated group. Body weight of animals was determined prior to the experiment and the administered volume of Formula 2 formulation was adjusted according to the body weight. During the experiment, mice body weight and paralysis clinical score was monitored daily. EAE score was calculated based on criteria shown in Table 4.

TABLE 4

| Score | Clinical manifestation |
|---|---|
| 1 | Limp tail |
| 2 | Partial hind leg paralysis |
| 3 | Complete hind leg paralysis |
| 4 | Complete hind and partial front leg paralysis |
| 5 | Moribund |

Mice from all groups were euthanized with isoflurane 24 hours post last dose administration. Two-way ANOVA statistical analysis was performed. Body weight was measured as an additional parameter for estimation of therapeutic effect of the compound of Formula 2.

Results

Figure 20A:
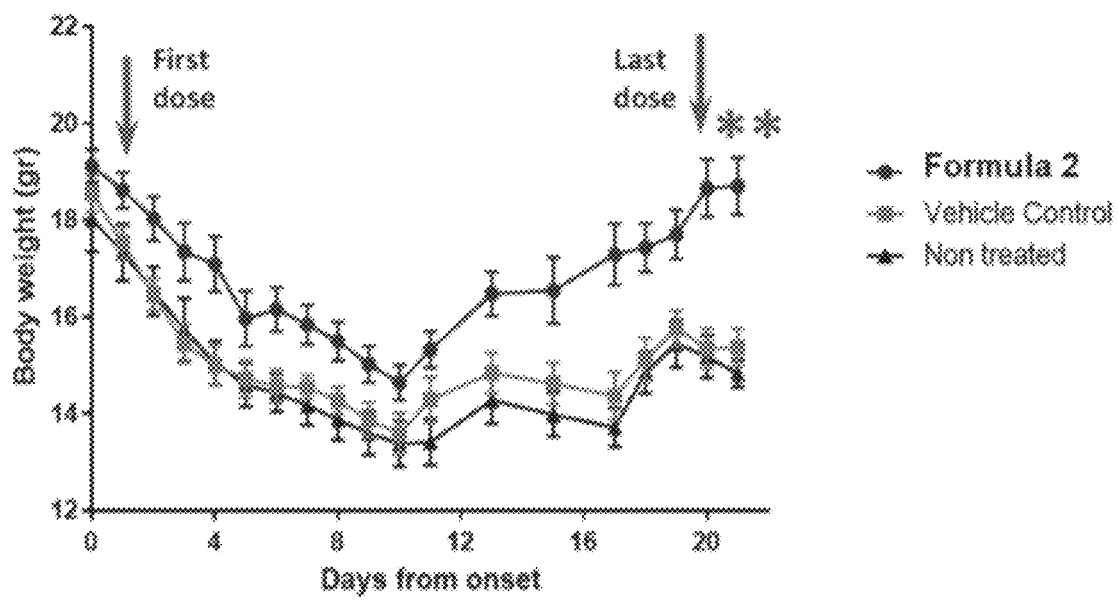
FIGS. 20A and 20B show the therapeutic effect of the compound of Formula 2 on mice body weight (20A) and paralysis clinical score (20B) in treatment mode in $MOG_{35-55}$/CFA-Induced direct Experimental Autoimmune Encephalomyelitis (EAE) in C57BL/6 mice administered at 15 mg/kg dose by subcutaneous injections (SC) (Example 9 below). Data shown mean±SEM, n=8
Figure 20B:
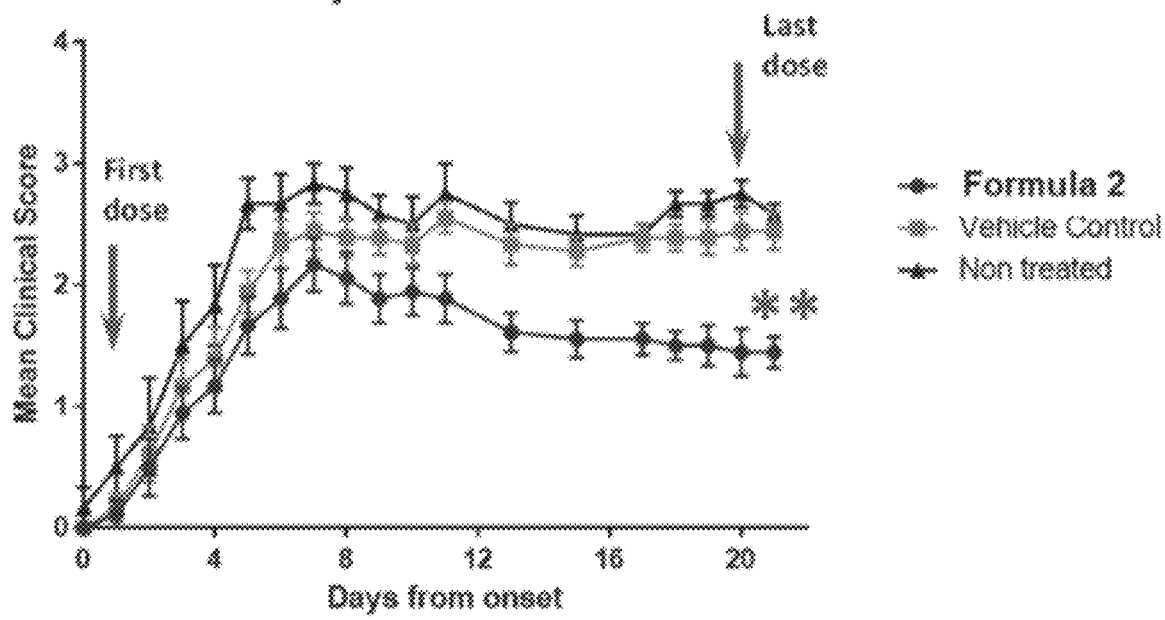

As can be seen from FIG. 20A, animals treated with the compound of Formula 2, showed by day 20 body weight recovery to that recorded on the onset of the disease. Non-treated and control mice were losing body weight during the entire period of the experiment and in average the difference between treated and no-treated group at the end of the experiment was approximately 4 g. Clinical score correlated with the dynamic of the body weight changes. Starting from day 10, treated by Formula 2 mice showed stable paralysis score and by day 20 the score started to decrease from 2 to 1.5 (FIG. 20B).

Example 10

Evaluation of Compound of Formula 2 In Vivo, in a High—Fat—Diet Induced Non-Alcoholic Fatty Liver Disease (NAFLD) Model in Mice, Histological Evaluation and NAFLD Activity Score, Liver and Mesenteric Fat Weight Evaluation Male C57BL/6J (Envigo, Israel) mice (3-4 weeks of age) were fed ad libitum a high fat, no high carbohydrate diet (modified Western diet, WD) with 42% kcal from fat and containing 0.1% cholesterol (Harlan TD.88137) with normal water (without high fructose-glucose solution) for 14 weeks prior to treatment initiation. Control mice were fed a standard chow diet (CD, Harlan TD.7012) with normal water (NW). Compound of Formula 2 was administrated on the $85^{th}$ day of the high fat diet (15 mg/kg, for S.C and IP at q3w regiment; 30 mg/kg for PO at qd regiment) for 65 days. Mock treated (vehicle) control group was administrated with IP injections at the same volume and regiment as a corresponding treated group for 65 days. Body weight of animals was determined prior to the treatment initiation and the administered volume of the compound of Formula 2 was adjusted according to the body weight. All animals were euthanized 24 hours post last dose administration. At necropsy liver and mesenteric fat wet weights were determined. Liver and mesenteric fat were fixed with 4% buffered formalin, embedded in paraffin, sections and H&E stained. Steatohepatitis was defined by the presence of steatosis, inflammation and hepatocellular ballooning, as per the FLIP algorithm. The severity of steatosis, lobular inflammation and hepatocellular ballooning were scored using the NASH-Clinical Research Network (CRN) criteria. NAFLD activity score (NAS) was calculated by adding the scores of: steatosis (maximal score 3) is defined by more than 66% of hepatocytes containing fat droplets; lobular inflammation (maximal score 3) is defined by >4 foci/200 field; hepatocyte ballooning (maximal score 2) is defined by many cells/prominent ballooning. Ordinary one-way ANOVA statistical analysis was performed.

Results

Figure 22:
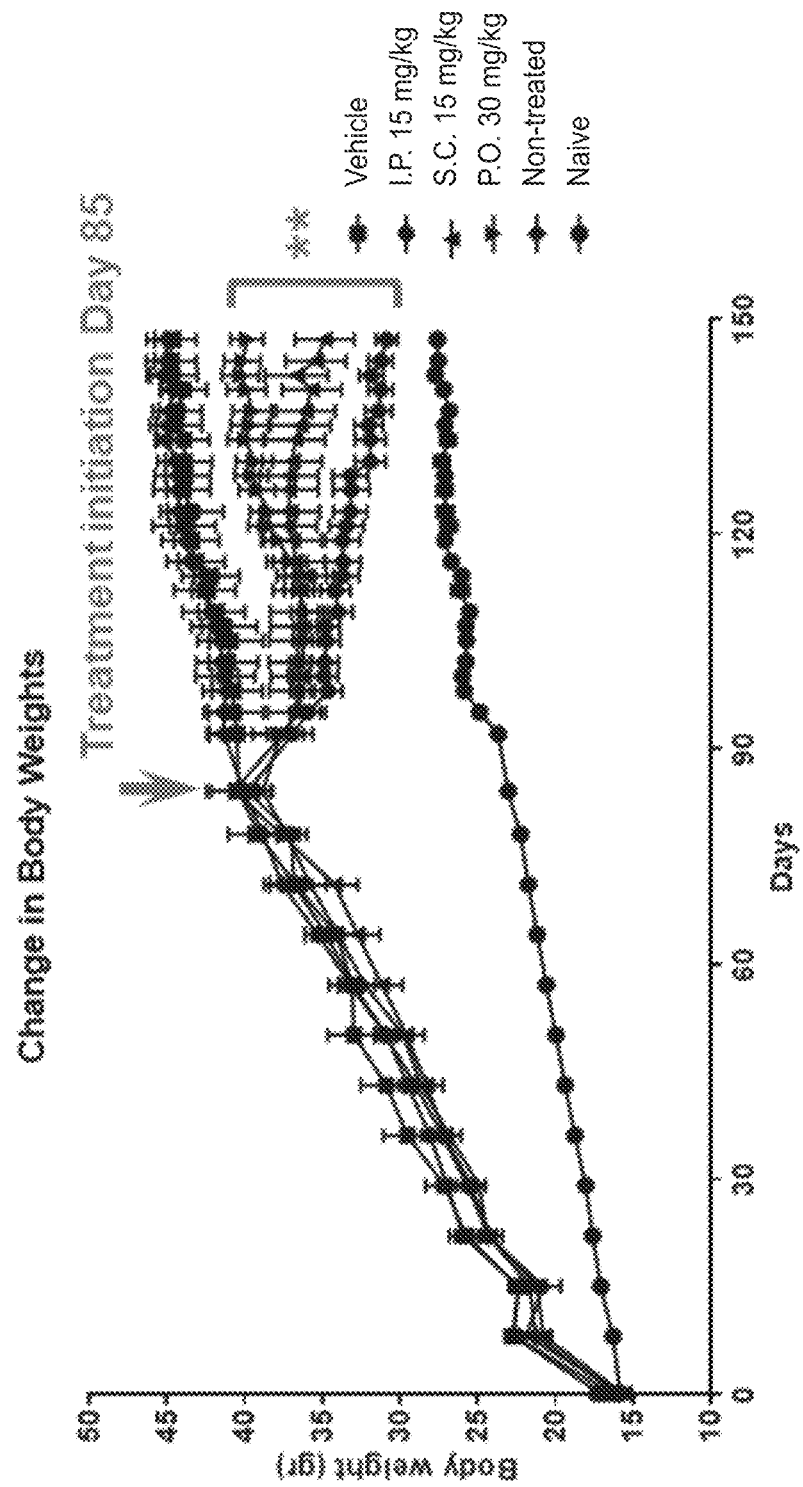
FIG. 22 shows the therapeutic effect of the compound of Formula 2 on mice body weight in High—Fat—Diet induced Fatty Liver Disease in C57BL/6 model administered at 2 doses by oral gavage (PO), intraperitoneal injection (IP) or subcutaneous injection (SC). Data shown mean±SEM, n=8.

Histology results are shown in FIGS. 21A-21B: liver (21A) and mesenteric fat (21B). Mice treated with the compound of Formula 2 showed significant reduction in the NAFLD activity score (FIG. 21C), wet liver weight (FIG. 21D), mesenteric fat weight (FIG. 21E) and mice body weight (FIG. 22).

Example 11

Evaluation of Compound of Formula 2 In Vivo, in a Collagen Induced Arthritis (CIA) Model in DBA/1 Mice: Clinical Score, Histological Score and Limb Thickness Evaluation Male DBA/lOlaHsd mice (7-8 weeks of age) were injected with CII (Type II collagen)+CFA (complete Frennd's adjuvant) emulsion on Day 0 (S.C.) to persuade collagen induced arthritis (CIA). On Day 21 the animals receive the same amount of the emulsion as a booster. Twice between Days 0 and 18 after immunization (before enrollment begins), both hind paws of all mice were measured using calipers to establish baseline values for paw thickness. On Day 22 mice were enrolled into groups when they first shown paw swelling and treatment was initiated. A working formulation of compound of Formula 2 was administered by IP injections at 15 mg/kg dose at q3w regiment. Mock treated (vehicle) control group was administered IP with the same volume and regiment as a treatment group. Administration was performed at a constant volume dosage based on individual body weight. The severity of CIA was monitored daily. The CIA scoring is on the scale of 0 to 16 (0 to 4 for each paw, adding the scores for all 4 paws). On day 43 (24 hours post last dose administration) all paws thickness was measured and mice were euthanized. All limbs from each mouse were placed in individual labeled tubes, fixed in 4% buffered formalin, paraffin embedded and sectioned. Histological score was assessed using hematoxylin and eosin (H&E) stained sections. Joints were scored for inflammation, cartilage damage, pannus formation, and bone resorption on a scale of 0 to 3 for each readout. Two-way ANOVA statistical analysis was performed.

Results

Figure 23:
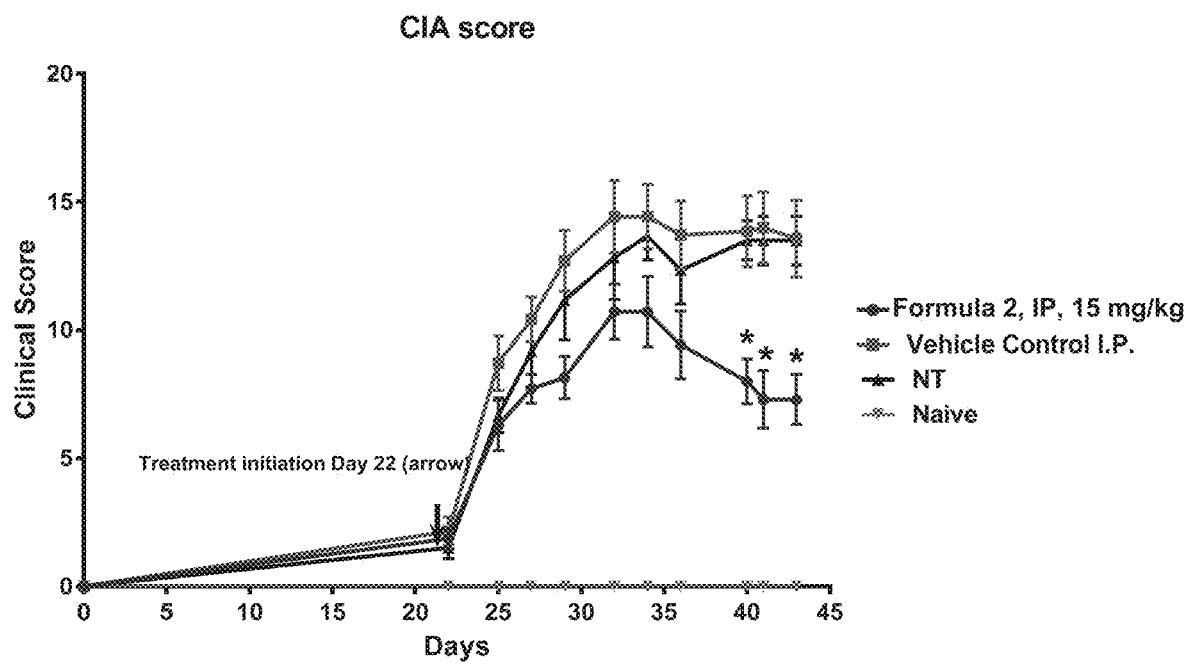
FIG. 23 shows the therapeutic effect of the compound of Formula 2 in Collagen Induced Arthritis (CIA) model in DBA/1 mice (CIA score) administered at 15 mg/kg by subcutaneous injection (SC) (Example 11 below). Data shown mean±SEM, n=8.

The CIA scoring is shown in FIG. 23.

Figures 24A, 24B, 24C:
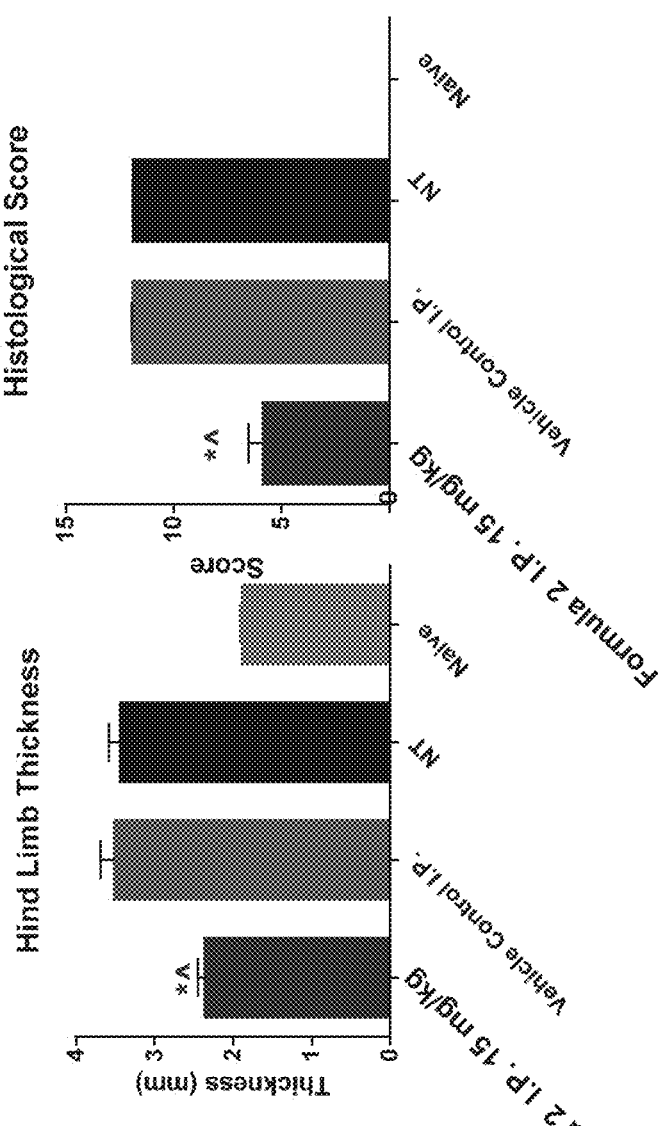
FIGS. 24A-24C show the therapeutic effect of the compound of Formula 2 in Collagen Induced Arthritis (CIA) model in DBA/1 mice (limb thickness and histological score). Data shown mean±SEM, n=8.

As can be seen from FIGS. 24A and 24B, fore and hind limb thickness was significantly reduced in mice treated with the compound of Formula 2. Histological score in mice treated with the compound of Formula 2 was also significantly reduced (FIG. 24C).

FIGS. 25A-25B show representative sections through the talus and calcaneum joint of naïve (25A) and Formula 2 treated (25B) mouse. Soft tissues surrounding the joints of the control mice appeared normal. Surfaces of the bones are covered with smooth hyaline cartilage of the uniform thickness. No cartilage and bone and erosion and profuse infiltration of inflammatory cells are present. FIGS. 25C-25J show bone (25C) and cartilage erosion (25D), pannus formation (25E and 25F), and soft tissue infiltration (25G and 25H, 25I and 25J) in non-treated and vehicle treated mice respectively.

Example 12

Investigation of Modes of Action of Compound of Formula 2 and Tysabri® in B-Lymphocyte Transmigration Assays The effect of the compound of Formula 2 was tested on B cells in a MesenFlow assay, as described in Example 4 herein above. Model that uses a chronic inflammatory stimuli (Acute+lymphoid chemokines). To identify any potential differences in mode-of-action, Tysabri® (Natalizumab), an antibody against alpha 4 integrin, which has been postulated to block lymphocyte transmigration, was used as a positive control.

Results

Figure 26:
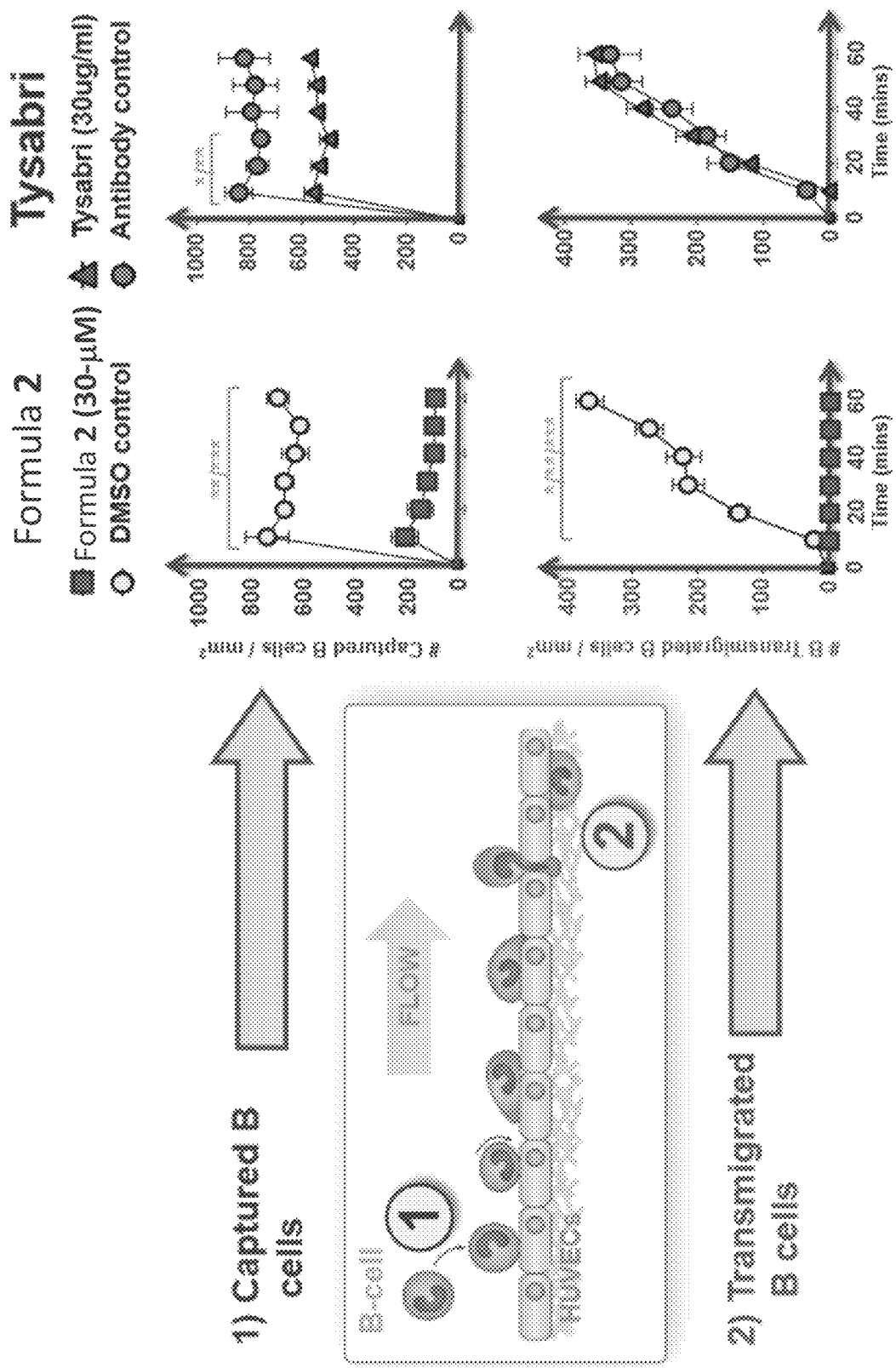
FIG. 26 shows different mode of effect of the compound of Formula 2 and Tysabri® on B cell adhesion and transmigration (Example 12 below). n=3.

Compound of Formula 2 (at 30 µM) had a significant effect on B lymphocyte transmigration blocking both adhesion and transmigration (FIG. 26). These results indicate that the compound of Formula 2 is a potent blocker of B cell trafficking far superior to Tysabri® (at 30 µg/ml), which had no net effect on the number of transmigrated B cells. The compound of Formula 2 had a dramatic blocking effect on B cell adhesion and transmigration, differentiating it from Tysabri®.

Example 13

Phenotypic Changes at Endothelial Junctions with the Compound of Formula 2

Figure 27:
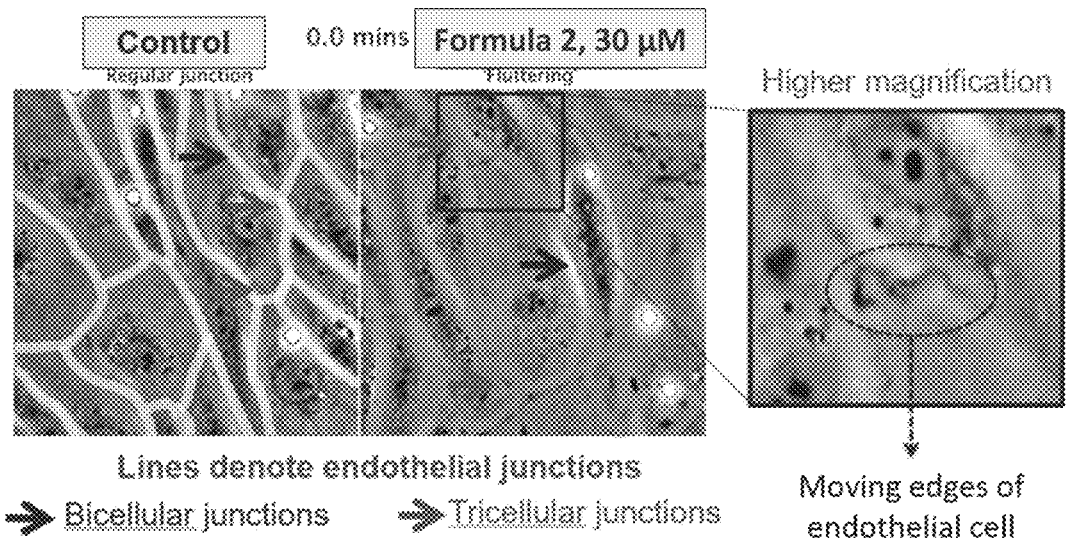
FIG. 27 shows phenotypic manifestations, termed "Fluttering", of a distinctive movement within the HUVECs intercellular junctions observed after treatment with compound of Formula 2 (Example 13 below).

Additional in-vitro results using the MesenFlow system showed phenotypic manifestations of a distinctive movement within the HUVECs intercellular junctions observed after treatment with compound of Formula 2. This manifestation was termed "Fluttering". Fluttering was characterized by a rapid fluctuating movement at the intercellular junctions of adjacent HUVECs, and predominantly within tricellular corners. This was characterized by a rapid change in phase at the cellular edges consistent with a physical movement that was associated with no leukocytes adhesion or migration within these regions (FIG. 27). Fluttering was observed in all HUVECs co-culture experiments that were treated with the compound of Formula 2. In all cases, junctional integrity was maintained, and no physical breakdown was observed at endothelial intercellular contacts. This observation is therefore representative of a phenotype that is indicative of a disruption in leukocyte transmigration.

Example 14

In Silico PECAM1 Model and Binding Mode of Compound of Formula 2

Figure 28:
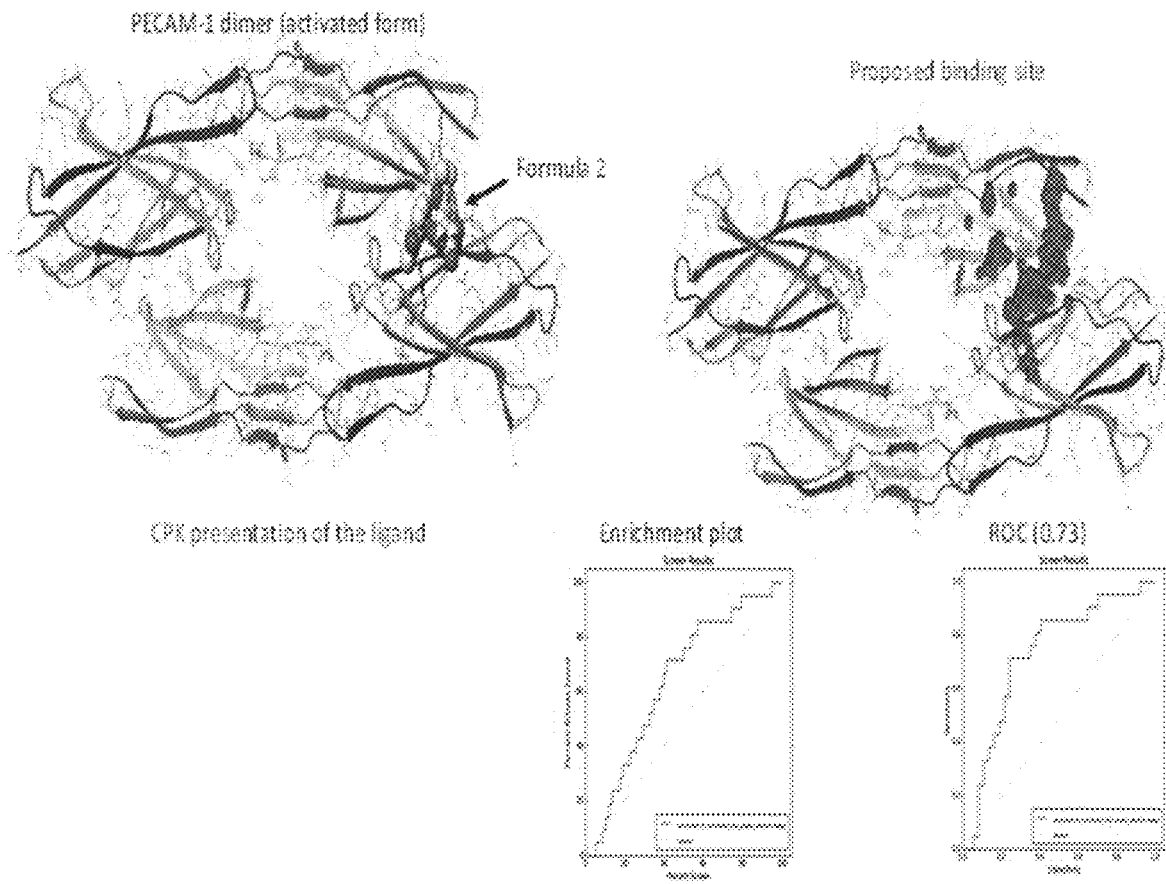
FIG. 28 shows possible binding mode between the compound of Formula 2 to PECAM-1 dimer interface. In silico obtained results (Example 14 below).

FIG. 28 shows a possible binding mode between the compound of Formula 2 and PECAM-1 dimer interface. The model was developed based on in silico calculations, and predicts that the compound of Formula 2 binds to the active PECAM1 dimer form and not to the non-active PECAM1 monomer (Chistiakov D A, Exp Mol Pathol. 2016, 100:409-415). Such difference may bring very important advantage in the clinic, because it suggests that treatment with the compounds of general Formula (I) selectively blocks PECAM-1 in the area of a disease only.

The invention claimed is:

1. A compound selected from the compounds of Formula 1, Formula 5, Formula 6, Formula 7 and Formula 9:

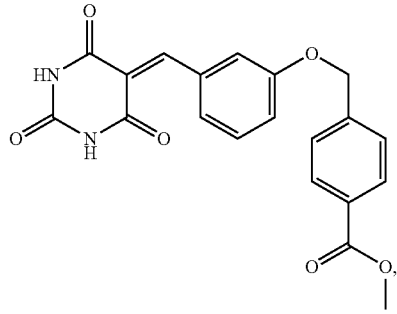

Formula 1

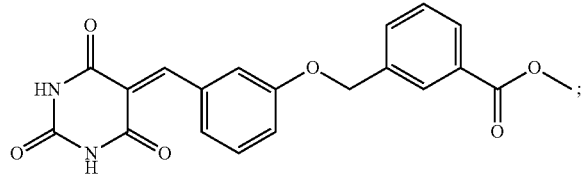

Formula 5

Formula 6

Formula 7

Formula 9 or pharmaceutically acceptable salts thereof.

2. A pharmaceutical composition comprising one or more of compounds of claim 1, or a pharmaceutically acceptable salt thereof, and a pharmaceutically acceptable carrier and/or diluent.

3. A method of inhibiting leukocyte transmigration in a subject in need thereof, comprising administering to the subject a therapeutically effective amount of a compound of general Formula (Ib)

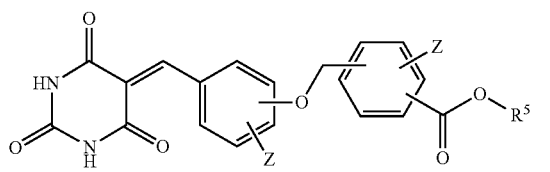

Formula (Ib)

wherein
- Z is for each phenyl ring independently one or two functional groups; each Z is attached to any available carbon atom of the ring in which it is present; at least one Z is present, and each Z is independently selected from linear alkyl or branched alkyl, wherein each of the linear alkyl or the branched alkyl may be unsubstituted or substituted with one or more of halo, haloalkyl, cyano, nitro, hydroxyl, alkenyl, aryl, alkoxy, aryloxy, aralkoxy, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, carboxylic ester, alkoxycarbonyl, aryloxycarbonyl, sulfo, alkylsulfonylamido, alkylsulfonyl, arylsulfonyl, alkylsulfinyl, arylsulfinyl;
- $R^5$ is alkyl, selected from linear alkyl or branched alkyl, wherein the alkyl may be unsubstituted or substituted with one, two, or three substituents selected from the group consisting of halo, nitro, cyano and amino; and
stereoisomers, enantiomers, and tautomers thereof, pharmaceutically acceptable salts thereof and mixtures thereof.

4. The method of claim 3, wherein in the compound of general Formula (Ib) one or two Z are present on one ring and are absent on the other ring.

5. The method of claim 3, wherein in the compound of general Formula (Ib) one or two Z are present on both rings.

6. The method of claim 3, wherein in the compound of general Formula (Ib) one or two Z are present on the phenyl ring connected to the barbituric moiety and Z is absent on the other ring.

7. The method of claim 3, wherein in the compound of general Formula (Ib) two Z are present.

8. The method of claim 3, wherein in the compound of general Formula (Ib) two Z are present on the same phenyl ring.

9. The method of claim 3, wherein in the compound of general Formula (Ib) each Z is independently selected from unsubstituted linear alkyl or unsubstituted branched alkyl.

10. The method of claim 9, wherein in the compound of general Formula (Ib) each Z is independently selected from unsubstituted linear alkyl or unsubstituted branched alkyl, having 1 to 6 carbon atoms ($C_{1-6}$alkyl).

11. The method of claim 10, wherein in the compound of general Formula (Ib) each Z is independently selected from methyl, ethyl, n-propyl, iso-propyl, butyl, iso-butyl, sec-butyl, tert-butyl, n-pentyl, iso-pentyl, neo-pentyl, tert-pentyl, n-hexyl, and iso-hexyl, preferably from methyl, ethyl, n-propyl, iso-propyl, butyl, iso-butyl, sec-butyl, or tert-butyl.

12. The method of claim 3, wherein in the compound of general Formula (Ib) $R^5$ is substituted with one, two, or three substituents selected from the group consisting of halo, nitro, cyano and amino.

13. The method of claim 3, wherein in the compound of general Formula (Ib) $R^5$ is unsubstituted.

14. The method of claim 3, wherein in the compound of general Formula (Ib) the carboxylic group —CO(=O)$R^5$ is present at the para position to the linking group —O—CH$_2$—.

15. The method of claim 3, wherein in the compound of general Formula (Ib) the carboxylic group —CO(=O)$R^5$ is present at the meta position to the linking group —O—CH$_2$—.

16. The method of claim 3, wherein in the compound of general Formula (Ib) wherein the carboxylic group —CO(=O)$R^5$ is present at the ortho position to the linking group —O—CH$_2$—.

17. The method of claim 3, wherein in the compound of general Formula (Ib) the bonds to the barbituric acid moiety and to the linking group —O—CH$_2$— are located para to each other.

18. The method of claim 3, wherein in the compound of general Formula (Ib) the bonds to the barbituric acid moiety and to the linking group —O—CH$_2$— are located meta to each other.

19. The method of claim 3, wherein in the compound of general Formula (Ib) the bonds to the barbituric acid moiety and to the linking group —O—CH$_2$— are located ortho to each other.

20. The method of claim 3, wherein the compound of general Formula (Ib) is a compound of Formula 2:

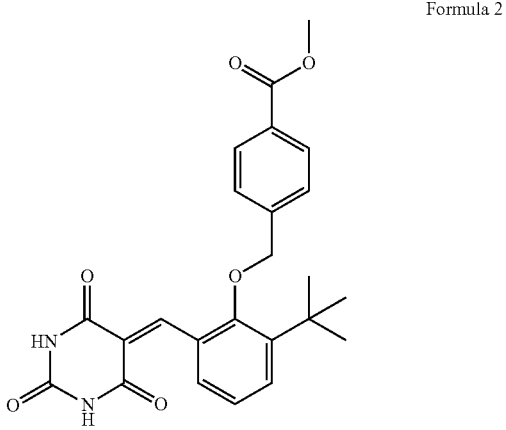

Formula 2 or pharmaceutically acceptable salt thereof.

21. The method of claim 3, wherein the compound of general Formula (Ib) is a compound of Formula 4:

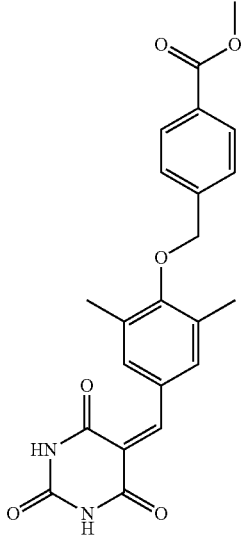

Formula 4 or pharmaceutically acceptable salt thereof.

22. The method of claim 3, for treating a disease or condition associated with leukocyte transmigration.

23. The method of claim 22, wherein the disease or condition is selected from inflammatory diseases and disorders, autoimmune diseases and disorders, and cancers.

24. A method of inhibiting leukocyte transmigration in a subject in need thereof, comprising administering to the subject a therapeutically effective amount of a compound as defined in claim 1.

25. The method of claim 24, for treating a disease or condition associated with leukocyte transmigration.

26. The method of claim 25, wherein the disease or condition is selected from inflammatory diseases and disorders, autoimmune diseases and disorders, and cancers.

27. A method of inhibiting leukocyte transmigration in a subject in need thereof, comprising administering to the subject a therapeutically effective amount of a compound of Formula 10:

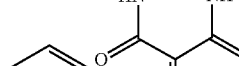

Formula 10 or pharmaceutically acceptable salt thereof.

28. The method of claim 27, for treating a disease or condition associated with leukocyte transmigration, wherein the disease or condition is selected from inflammatory diseases and disorders, autoimmune diseases and disorders, and cancers.

* * * * *